(12) United States Patent
Gogos et al.

(10) Patent No.: US 9,701,727 B2
(45) Date of Patent: Jul. 11, 2017

(54) INHIBITOR OF NEURONAL CONNECTIVITY LINKED TO SCHIZOPHRENIA SUSCEPTIBILITY AND COGNITIVE DYSFUNCTION

(71) Applicant: The Trustees of Columbia University in the City of New York, New York, NY (US)

(72) Inventors: Joseph A. Gogos, Riverdale, NY (US); Bin Xu, Fort Lee, NJ (US); Maria Karayiorgou, Riverdale, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 0 days.

(21) Appl. No.: 14/136,345

(22) Filed: Dec. 20, 2013

(65) Prior Publication Data
US 2014/0187608 A1    Jul. 3, 2014

Related U.S. Application Data

(63) Continuation of application No. PCT/US2012/045093, filed on Jun. 29, 2012.

(60) Provisional application No. 61/502,661, filed on Jun. 29, 2011.

(51) Int. Cl.
| | |
|---|---|
| C12N 15/11 | (2006.01) |
| C07K 14/435 | (2006.01) |
| A61K 38/17 | (2006.01) |
| G01N 33/68 | (2006.01) |
| C12N 15/113 | (2010.01) |
| C07K 14/47 | (2006.01) |

(52) U.S. Cl.
CPC ........ *C07K 14/435* (2013.01); *A61K 38/1709* (2013.01); *C07K 14/4703* (2013.01); *C12N 15/113* (2013.01); *G01N 33/6896* (2013.01); *C12N 2310/11* (2013.01); *C12N 2310/14* (2013.01); *C12N 2310/141* (2013.01)

(58) Field of Classification Search
None
See application file for complete search history.

(56) References Cited

U.S. PATENT DOCUMENTS

| | | | |
|---|---|---|---|
| 5,476,874 | A | 12/1995 | Hungate et al. |
| 8,101,602 | B2 | 1/2012 | Menear et al. |
| 2001/0053519 | A1 | 12/2001 | Fodor et al. |
| 2006/0165679 | A1 | 7/2006 | Golz et al. |
| 2007/0160985 | A1 | 7/2007 | Gallaher et al. |
| 2008/0113351 | A1* | 5/2008 | Naito et al. ............ 435/6 |
| 2008/0207697 | A1 | 8/2008 | Andrieux et al. |
| 2008/0254462 | A1 | 10/2008 | Gogos et al. |
| 2009/0042973 | A1 | 2/2009 | Hale et al. |
| 2010/0119626 | A1 | 5/2010 | Ramsey et al. |
| 2010/0197772 | A1 | 8/2010 | Califano et al. |
| 2010/0227908 | A1 | 9/2010 | Cairns |
| 2010/0297070 | A1 | 11/2010 | Dugan et al. |
| 2011/0071049 | A1 | 3/2011 | Heintz et al. |
| 2011/0136738 | A1* | 6/2011 | Murphy et al. ............ 514/8.3 |
| 2012/0190676 | A1 | 7/2012 | Moorman et al. |
| 2014/0171371 | A1 | 6/2014 | Vacic et al. |
| 2015/0239831 | A1 | 8/2015 | Landry et al. |
| 2015/0241410 | A1 | 8/2015 | Karayiorgou et al. |
| 2016/0089377 | A1 | 3/2016 | Karayiorgou et al. |

FOREIGN PATENT DOCUMENTS

| | | |
|---|---|---|
| CN | 102 488 687 A | 6/2012 |
| EP | 0 766 674 | 10/2003 |
| WO | WO 95/24385 | 9/1995 |
| WO | WO 95/35286 | 12/1995 |
| WO | WO 97/27180 | 7/1997 |
| WO | WO 97/40825 | 11/1997 |
| WO | WO 03/070743 | 8/2003 |
| WO | WO 03/080867 | 10/2003 |
| WO | WO 2004/094589 | 11/2004 |
| WO | WO 2011/017089 | 2/2011 |
| WO | WO 2012/094681 | 7/2012 |
| WO | WO 2012/094703 | 7/2012 |
| WO | WO 2012/106404 | 8/2012 |

(Continued)

OTHER PUBLICATIONS

Ross et al., Neurobiology of schizophrenia, 2006, Neuron, vol. 52, pp. 139-153.*
Green et al., First episode schizophrenia-related psychosis and substance use disorders: acute response to olanzapine and haloperidol, 2004, Schizophrenia Research, vol. 66, pp. 125-135.*
Hill et al., Impairment of verbal memory and learning in antipsychotic-naïve patients with first-episode schizophrenia, 2004, Schizophrenia Research, vol. 68, pp. 127-136.*
Kelley et al., The effect of chronic haloperidol treatment on dendritic spines in the rat striatum, 1997, Experimental Neurology, vol. 146, pp. 471-478.*
Glausier et al., Dendritic spine pathology in schizophrenia, 2013, Neuroscience, vol. 251, pp. 90-107.*
Rattus norvegicus similar to 2310044H10Rik protein, mRNA (cDNA clone MGC:93975 IMAGE:7114835), complete cds, GenBank BC079041, Jul. 15, 2006, accessed and retrieved from www.ncbi.nlm,gov on Oct. 14, 2014.*
Deng et al., New neurons and new memories: how does hippocampal neurogenesis affect learning and memory?, 2010, Nature Reviews Neuroscience, vol. 11, pp. 339-350.*

(Continued)

*Primary Examiner* — Dana Shin
(74) *Attorney, Agent, or Firm* — Baker Botts L.L.P.

(57) ABSTRACT

The present invention relates to methods and compositions for enhancing neuronal connectivity. It is based, at least in part, on the discovery of a protein, termed "Mirta22," that inhibits the formation of structures which create connections between neurons. It is further based, in part, on the discovery that inhibiting Mirta22 activity by short hairpin RNA was able to restore these structures. Mirta22 was discovered in experiments relating to 22q11 microdeletions, which have been linked to schizophrenia. Accordingly, the present invention provides for methods of treating schizophrenia comprising administering an agent that inhibits Mirta22 activity. It may also be used in the treatment of other disorders that would benefit from enhanced neural connectivity, including learning and memory disorders.

3 Claims, 65 Drawing Sheets

(56) References Cited

FOREIGN PATENT DOCUMENTS

Figures 1C, 1D:
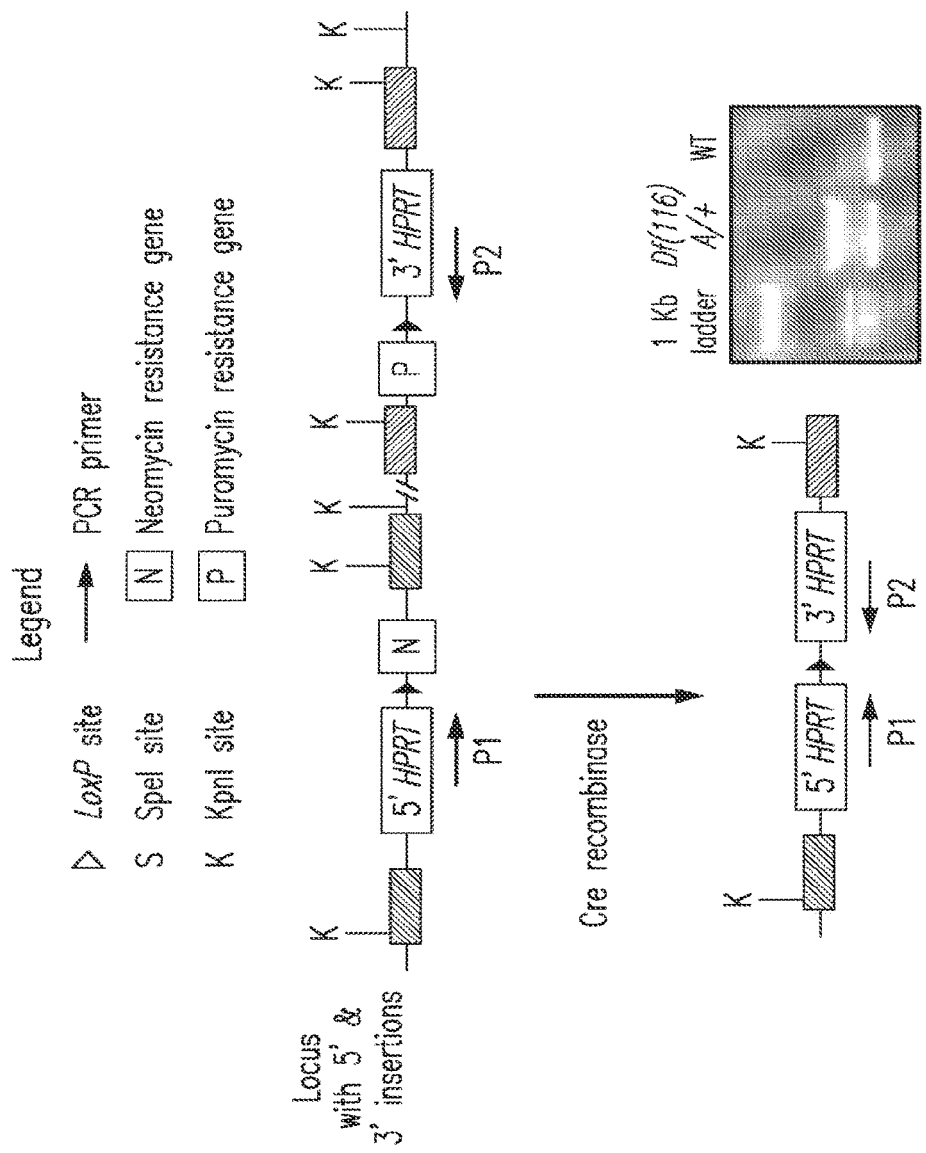
Figure 2A:
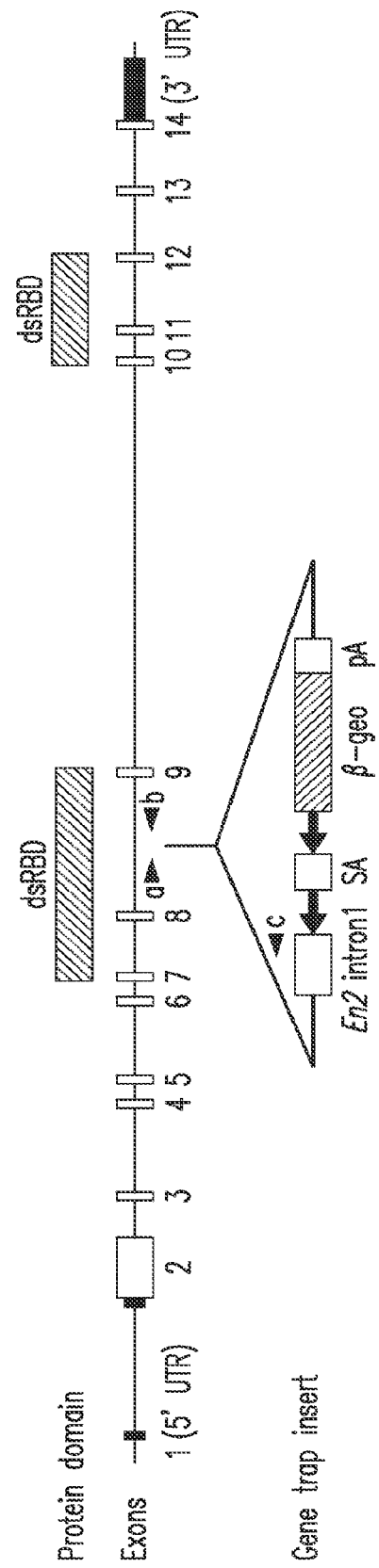
Figure 2B:
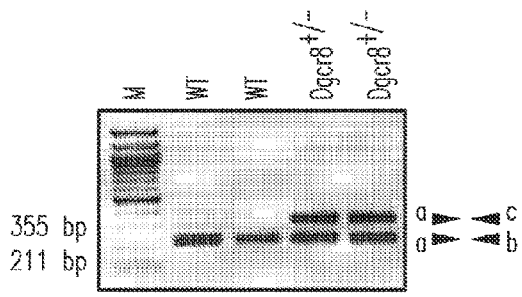
Figure 2C:
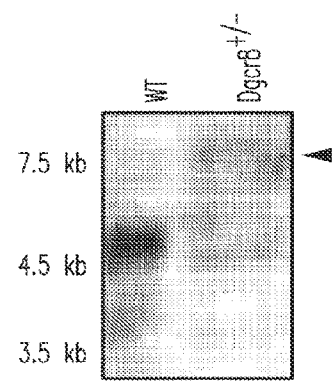
Figure 2D:
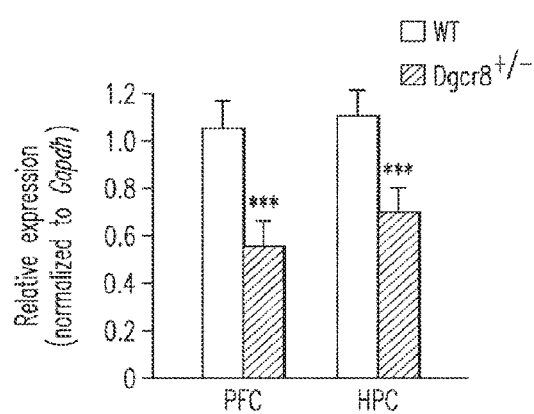
Figure 2E:
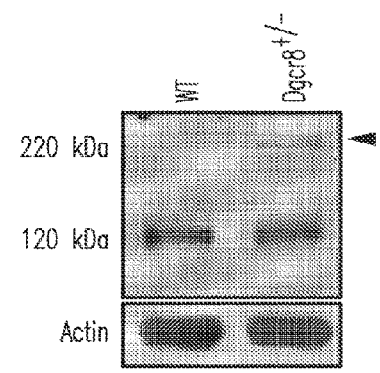

| WO | WO 2013/116589 | 8/2013 |
|----|----------------|--------|
| WO | WO 2014/145857 A1 | 9/2014 |

OTHER PUBLICATIONS

Harrison et al., Neuropathological studies of synaptic connectivity in the hippocampal formation in schizophrenia, 2001, Hippocampus, vol. 11, pp. 508-519.*
Eroglu et al., Regulation of synaptic connectivity by glia, 2010, Nature, vol. 468, pp. 223-231.*
Junes-Gill et al., hHSS1: a novel secreted factor and suppressor of glioma growth located at chromosome 19q13.33, 2011, Journal of Neurooncology, vol. 102, pp. 197-211.*
Homo sapiens ER membrane protein complex subunit 10 (EMC10), GenBank accession No. NM_206538.3, Mar. 15, 2015, accessed and retrieved from www.ncbi.nim.gov on Mar. 26, 2015.*
Junes-Gill et al., Human hematopoietic signal peptide-containing secreted 1 (hHSS1) modulates genes and pathways in glioma: implications for the regulation of tumorigenicity and angiogenesis, 2014, BMC Cancer, vol. 14:920, pp. 1-17.*
Wen et al., PNAS, 2010, 107:13906-13911.*
Ashhab et al., FEBS Letters, 2001, 495:56-60.*
Van Itallie et al., American Journal of Physiology—Renal Physiology, 2006, 291:F1288-F1299.*
Péterfy et al., The Journal of Biological Chemistry, 2005, 280:32883-32889.*
Xu et al., Derepression of a neuronal inhibitor due to miRNA dysregulation in a schizophrenia-related microdeletion, 2013, Cell, vol. 152, pp. 262-275.*
Dlamantopoulou et al., Contribution of a novel neuronal inhibitor to the behavioral, synaptic and plasticity deficits observed in a mouse model of 22q11.2 microdeletion-related schizophrenia, May 1, 2016, Biological Psychiatry, vol. 79, No. 9, Supplement 1, p. 342S, Abstract No. 1005.*
U.S. Appl. No. 11/947,361, Jun. 21, 2013 Notice of Abandonment.
U.S. Appl. No. 11/947,361, Dec. 13, 2012 Final Office Action.
U.S. Appl. No. 11/947,361, Sep. 19, 2012 Response to Non-Final Office Action.
U.S. Appl. No. 11/947,361, Mar. 26, 2012 Non-Final Office Action.
U.S. Appl. No. 11/947,361, Sep. 6, 2011 Amendment and Request for Continued Examination (RCE).
U.S. Appl. No. 11/947,361, Mar. 4, 2011 Final Office Action.
U.S. Appl. No. 11/947,361, Dec. 3, 2010 Response to Non-Final Office Action.
U.S. Appl. No. 11/947,361, Sep. 3, 2010 Non-Final Office Action.
U.S. Appl. No. 11/947,361, Jun. 17, 2010 Response to Restriction Requirement.
U.S. Appl. No. 11/947,361, Mar. 25, 2010 Restriction Requirement.
Aleman, et al., "Sex differences in the risk of schizophrenia", Arch. Gen. Psychiatric, 60:565-571 (2003).
American Psychiatric Association, DSM-IV Casebook "A learning companion to the diagnostic and statistical manual of mental disorders" Fourth Edition, Am Psychiatric Press, Washington, DC, (4 pages) (1994), cover and contents pages only.
Bassett, et al., "The schizophrenia phenotype in 22q11 deletion syndrome", Am. J. Psychiatric, 160:1580-1586 (2003).
Bateman, et al., "Tissue-specific RNA surveillance? Nonsense-mediated mRNA decay causes collagen X haploinsufficiency in Schmid metaphyseal chondrodysplasia cartilage", Human Molecular Genetics, 12(3):217-225 (2003).
Bearden, et al., "The neurocognitive phenotype of the 22a11.2 deletion syndrome: selective deficit in visual-spatial memory", Journal of Clinical and Experimental Neuropsychology, 23(4):447-464 (2001).
Blouin, et al., "Schizophrenia susceptibility loci on chromosomes 13q32 and 8p21", Nature Genetics, 20:70-73 (1998).
Boudreau, et al., "Minimizing variables among hairpin-based RNAi vectors reveals the potency of shRNAs", RNA, 14:1834-1844 (2008).
Brummelkamp, et al., "A system for stable expression of short interfering RNAs in mammalian cells", Science, 296:550-553 (2002).
Bunting, et al., "Targeting genes for self-excision in the germ line", Gene & development, 12:1524-1528 (1999).
Burmistrova, et al., "MicroRNA in schizophrenia: genetic and expression analysis of miR-130b (22q11)", Biochemistry (Moscow), 72(5):578-582 (2007).
Carlin, et al., "Isolation and characterization of postsynaptic densities from various brain regions: Enrichment of different types of postsynaptic densities", The Journal of Cell Biology, 86:831-843 (1980).
Carthew, et al., "Origins and mechanisms of miRNAs and siRNAs", Cell, 136(4):642-655 (2009).
Chow, et al., "Structural brain abnormalities in patients with schizophrenia and 22q11 deletion syndrome", Society of Biological Psychiatric, 51:208-215 (2002).
Chow, et al., "Qualitive MRI findings in adults with 22q11 deletion syndrome and schizophrenia", Society of Biological Psychiatric, 46:1436-1442 (1999).
Chu, et al., "Identification and characterization of a small molecule antagonist of human VPAC2 receptor", Molecular Pharmacology, 77(1):95-101 (2010).
Collier, et al., "The genetics of schizophrenia: glutamate not dopamine?", European Journal of Pharmacology, 480:177-184 (2003).
Dirksen, et al., "Multiple splicing signals control alternative intron retention of bovine growth hormone pre-mRNA", The Journal of Biological Chemistry, 270(10):5346-5352 (1995).
Drew, et al., "Evidence for altered hippocampal function in a mouse model of the human 22q11.2 microdeletion", Molecular and Cellular Neuroscience, 47(4):293-305 (2011).
Drysdale, et al., "Complex promoter and coding region β2-adrenergic receptor haplotypes alter receptor expression and predict in vivo responsiveness", PNAS, 97(19):10483-10488 (2000).
D'Souza, et al., "Sexual dimorphism in the response to N-Methyl-D-Aspartate receptor antagonists and morphine on behavior and C-FOS induction in the rat brain", Neuroscience, 93(4):1539-1547 (1999).
DuMontcel, et al., "Prevalence of 22q11 microdeletion", J. Med Genet., 33:719 (1996).
Edelmann, et al., "A common molecular basis for rearrangement disorders on chromosome 22q11", Human Molecular Genetics, 8(&):1157-1167 (1999).
Egan, et al., "Effect of COMT Val$^{108/158}$ met genotype on frontal lobe function and risk for schizophrenia", PNAS, 98(12):6917-6922 (2001).
El-Husseini, et al., "Protein palmitoylation: A regulator of neuronal development and function", Nature Review, Neuroscience, 3:791-802 (2002).
El-Husseini, et al., "Synaptic strength regulated by palmitate cycling on PSD-95", Cell, 108:849-863 (2002).
Fenelon, et al., "Deficiency of Dgcr8, a gene disrupted by the 22q11.2 microdeletion, results in altered short-term plasticity in the prefrontal cortex", PNAS, 108(11):4447-4452 (2011).
Glaser, et al., "No association between the putative functional ZDHHC8 single nucleotide polymorphism rs175174 and schizophrenia in large European samples", Biol. Psychiatric, 58:78-80 (2005).
Gogos, et al., "The gene encoding proline dehydrogenase modulates sensorimotor gating in mice", Nature Genetics, 21:434-439 (1999).
Gogos, et al., "Genetic ablation and restoration of the olfactory topographic map", Cell, 103:609-620 (2000).
Grady, et al., "Altered brain functional connectivity and impaired short-term memory in Alzheimer's disease", Brain, 124:739-756 (2001).
Hennah, et al., "Haplotype transmission analysis provides evidence of association for DISC1 to schizophrenia and suggests sex-dependent effects", Human Molecular Genetics, 12(3):3151-3159 (2003).
Hegel, "SNP judgements and freedom of association", Arterioscler. Throm. Vase. Biol., 22:1058-1061 (2002).

(56) References Cited

OTHER PUBLICATIONS

Hoffman, et al., "A short hairpin DNA analogous to miR-125b inhibits C-Raf expression, proliferation, and survival of breast cancer cells", *Mol Cancer Res*, 7(10):1635-1644 (2009).
Huang, et al., "A suboptimal 5' splice site is a *cis*-acting determinant of nuclear export of polymavirus late mRNAs", *Molecular and Cellular Biology*, 16(11):6046-6054 (1996).
Jacquet, et al., "PRODH mutations and hyperprolinemia in a subset of schizophrenic patients", *Human Molecular Genetics*, 11(19):2243-2249 (2002).
Jiang, et al., "Use of cAMP BRET sensor to characterize a novel regulation of cAMP by the sphingosine 1-phosphate/g13 pathway", *J. Biol. Chem.*, 282(14):10576-10584 (2007).
Jongsma, et al., "BML-241 fails to display selective antagonism at the sphingosine-1-phosphate receptro, S1P(3)", *British Journal of Pharmacology*, 149(3):277-282 (2006).
Juppner, "Functional properties of the PTH/PTHrP receptor", *Bone*, 17(2):39S-42S (1995).
Kalus, et al., "The dendritic architecture of prefrontal pyramidal neurons in schizophrenic patients", *Clinical Neuroscience and Neuropathology*, 11(16):3621-6325 (2000).
Kanaani, et al., "A combination of three distinct trafficking signals mediates axonal targeting and presynaptic clustering of GAD65", *JCB*, 158(7):1229-1238 (2002).
Karayiorgou, et al., "2q11.2 microdeletions: linking DNA structural variation to brain dysfunction and schizophrenia", *Nat Rev Neurosci.*, 11(6):402-416 (2010).
Karayiorgou, et al., "Schizophrenia susceptibility associated with intestitial deletions of chromosome 22q11", *PNAS*, 92:7612-7616 (1995).
Kazmierski, et al., "Discovery of Potent pyrrolidone-based HIV-1 protease inhibitors with enhanced drug-like properties", *Bioorg. Med Chem. Lett.*, 14(22):5689-5692 (2004).
Kazmierski, et al., "Potent inhibitors of the HIV-1 protease incorporating cyclic urea P1-P2 scaffold", *Bioorg. Med. Chem. Lett.*, 14(22):5685-5687 (2004).
Kazmierski, et al., "Novel spirocyclic pyrrolidones as P2/P1 mimetics in potent inhibitors of HIV-1 protease", *Bioorg. Med. Chem. Lett.*, 12(23):3431-3433 (2002).
Kienzel, et al., "Intron retention may regulate expression of Epstein-Barr virus nuclear antigen 3 family genes", *Journal of Virology*, 73(2):1195-1204 (1999).
Kristiansen, et al., "Changes in NMDA receptor subunits and interacting PSD proteins in dorsolateral prefrontal and anterior cingulate cortex indicate abnormal regional expression in schizophrenia", *Molecular Psychiatry*, 11:737-747 (2006).
Li, et al., "Aph2, a protein with a *zf*-DHHC motif, interacts with c-Abl and has pro-apoptotic activity", *The Journal of Biological Chemistry*, 277(32):28870-28876 (2002).
Li, et al., "Evidence for association between novel polymorphisms in the PRODH gene and schizophrenia in a Chinese population", *American Journal of Medical Genetics Part B (Neuropsychiatric Genetics)*, 129B:13-15 (2004).
Linder, et al., "New insights into the mechanisms of protein palmitoylation", *Biochemistry*, 42(15):4311-4320 (2003).
Liu, et al., "Genetic variation at the 22q11 PRODH2/DGCR6 locus presents an unusual pattern and increases susceptibility to schizophrenia", *PNAS*, 99(6):3717-3722 (2002).
Liu, et al., "Genetic variation in the 22a11 locus and susceptibility to schizophrenia", *PNAS*, 99(26):16859-16864 (2002).
Lobo, et al., "Identification of a Ras Palmitoyltransferase in *Saccharomyces cerevisiae*", *The Journal of Biological Chemistry*, 277(43):41268-41273 (2002).
Lucentini, "Gene association studies typically wrong", *The Scientist*, 24:20 (2004).
Lutz, et al., "Structure of the human VIPR2 gene for vasoactive intestinal peptide receptor type 2", *FEBS Lett.*, 458(2):197-203 (1999).
NCBI NM_197991.2 "Mus musculus ER membrane protein complex subunit 10 (Emc10)", Mar. 10, 2011 [online]. [Retrieved on Aug. 29, 2012]. http://www.ncbi.nlm.nih.gov/nuccore/226342950?sat=14&satkey=9208675> Definition and Sequences.
Mackay, et al., "Chromosomal localiztion in mouse and human of the vasoactive intestinal peptide receptor type 2 gene: a possible contributor to the holoprosencephaly 3 phenotype", *Genomics*, 37(3):345-345 (1996).
Moghaddam, et al., "Reversal of phencyclidine effects by a group II metabotropic glutamate receptor agonist in rats", *Science*, 281:1349-1352 (1998).
Mukai, et al., "Evidence that the gene encoding ZDHHC8 contributes to the risk of schizophrenia", *Nature Genetics*, 36(7):725-731 (2004).
Murphy, et al., "High rates of schizophrenia in adults with veldcardio-facial syndrome", *Arch Gen Psychiatric*, 56(10):940-945 (1999).
Peltekova, et al., "Functional variants of OCTN cation transporter genes are associated with Crohn disease", *Nature Genetics*, 36(5):471-475 (2004).
Prange, et al., "A balance between excitatory and inhibitory synapses is controlled by PSD-95 and neuroligin", *PNAS*, 101(38):13915-13920 (2004).
Pulver, et al., "Psychotic illness in patients diagnosed with velocardio-facial syndrome and their relatives", *The Journal of Nervous and Mental Disease*, 182(8):476-478 (1994).
Renick, et al., "The mammalian brain high-affinity L-Proline transporter is enriched preferentially in synaptic vesicles in a subpopulation of excitatory nerve terminals in rat forebrain", *The Journal of Neuroscience*, 19(1):21-33 (1999).
Rosoklija, et al., "Structural abnormalities of subicular dendrites in subjects with schizophrenia and mood disorders", *Arch Gen Psychiatric*, 57:349-356 (2000).
Roth, et al., "The yeast DHHC cysteine-rich domain protein Akrlp is a palmitoyl transferase", *JCB*, 159(1):23-28 (2002).
Scambler, "The 22q11 deletion syndromes", *Human Molecular Genetics*, 9(6):2421-2426 (2000).
Shaikh, et al., "Chromosome 22-specific low copy repeats and the 22q11.2 deletion syndrome: genomic organization and deletion endpoint analysis", *Human Molecular Genetics*, 9(4):489-501 (2000).
Shaw, et al., "A genome-wide search for schizophrenia susceptibility genes", *American Journal of Medical Genetics (Neuropsychiatirc Genetics)*, 81:364-376 (1998).
Shifman, et al., "A highly significant association between a COMT haplotype and schizophrenia", *Am. J. Hum. Genet.*, 71:1296-1302 (2002).
Singaraja, et al., "HIP14, a novel ankyrin domain-containing protein, links huntington to intracellular trafficking and endocytosis", *Human Molecular Genetics*, 11(23):2815-2828 (2002).
Spaltenstein, et aL, "Novel inhibitors of HIV protease: design, synthesis and biological evaluation of picomolar inhibitors containing cyclic P1/P2 scaffolds", *Bioorg Med. Chem. Lett.*, 10(11):1159-1162 (2000).
Stark, et al., "Altered brain microRNA biogenesis contributes to phenotypic deficits in a 22q11-deletion mouse model", *Nat. Genet.*, 40(6):751-760 (2008).
Stephens, et al., "A VGF-derived peptide attenuates development of type 2 diabetes via enhancement of islet β-cell survival and function", *Cell Metabolism*, 16(1):33-43 (2012).
Swerdlow, et al., "Using an animal model of deficient sensorimotor gating to study the pathophysiology and new treatments of schizophrenia", *Schizophrenia Bulletin*, 24(2):285-301 (1998).
Uemura, et al., "Isolation and characterization of Golgi apparatus-specific GODZ with the DHHC zinc finger domain", *Biochemical and Biophysical Research Communications*, 296:492-496 (2002).
Usiskin, et al., "Velocardiofacial syndrome in childhood-onset schizophrenia", *J. Am. Acad. Child Adolesc. Psychiatric*, 38:1536-1543 (1999).
Vacic, et al., "Duplications of the neuropeptide receptor gene VIPR2 confer significant risk for schizophrenia", *Nature*, 471(7339):499-503 (2011).
International Search Report and Written Opinion for PCT/US2012/45093, dated Feb. 4, 2013.

(56) References Cited

OTHER PUBLICATIONS

International Search Report and Written Opinion for PCT/US2012/20683, dated May 8, 2012.
International Search Report and Written Opinion for PCT/US2013/69735, dated Mar. 6, 2014.
U.S. Appl. No. 13/935,248, Sep. 4, 2015 Non-Final Office Action.
U.S. Appl. No. 13/935,248, Dec. 4, 2015 Response to Non-Final Office Action.
"Running TaqMan Low Density Arrays on 7900HT Real-Time PCR Systems", User Bulletin for Applied Biosystems TaqMan Low Density Array (pp. 1-24 (Sep. 5, 2010)).
Busto, et al., "VIP and PACAP receptors coupled to adenylyl cyclase in human lung cancer: A study in biopsy specimens", Peptides, vol. 24, pp. 429-436 (2003).
U.S. Appl. No. 13/935,248, Aug. 16, 2016 Amendment and Request for Continued Examination (RCE).
U.S. Appl. No. 13/935,248, Feb. 16, 2016 Final Office Action.
U.S. Appl. No. 13/935,248, Aug. 18, 2015 Response to Restriction Requirement.
U.S. Appl. No. 13/935,248, Feb. 18, 2015 Restriction Requirement.
U.S. Appl. No. 14/707,918, Jan. 20, 2017 Final Office Action.
U.S. Appl. No. 14/707,918, Oct. 26, 2016 Response to Non-Final Office Action.
U.S. Appl. No. 14/707,918, Jul. 26, 2016 Non-Final Office Action.
U.S. Appl. No. 14/707,918, Jul. 12, 2016 Response to Restriction Requirement.
U.S. Appl. No. 14/707,918, Feb. 12, 2016 Restriction Requirement.
U.S. Appl. No. 14/850,471, Oct. 19, 2016 Response to Restriction Requirement.
U.S. Appl. No. 14/850,471, May 19, 2016 Restriction Requirement.
Curatolo et al., "mTOR Inhibitors m Tuberous Sclerosis Complex," Current Neuropharmacology, 10:404-415 (2012).
Ehninger et al., "From mTOR to Cognition: Molecular and Cellular Mechanisms of Cognitive Impairments in Tuberous Sclerosis," Journal of Intellectual Disability Research, 53(10):838-851 (Oct. 2009).
García-Echeverría, "Allosteric and ATP-competitive kinase inhibitors of mTOR for cancer treatment," Bioorganic & Medicinal Chemistry Letters, 20(15):4308-4312 (2010).
International Search Report mailed Jul. 24, 2014 in International Application No. PCT/US 14/30693.
Liu et al., "Characterization of Torin2, an ATP-Competitive Inhibitor of mTOR, ATM, and ATR," Cancer Research, 73(8):2574-2586 (2013).
Meffre et al., "5-HT 6 Receptor Recruitment of mTOR as a Mechanism for Perturbed Cognition in Schizophrenia," Embo Molecular Medicine, 4(10):1043-1056 (2012).
Moreno et al., "Development of selective agonists and antagonists for the human vasoactive intestinal polypeptide VPAC2 receptor," Peptides 21:1543-1549 (2000).
Partial Supplementary European search report dated Aug. 2, 2016 in EP Application No. 14762460.
Yu et al., "Beyond Rapalog Therapy: Preclinical Pharmacology and Antitumor Activity of WYE-125132, an ATP-Competitive and Specific Inhibitor of mTORC1 and mTORC2," Cancer Research, vol. 70(2):621-631. (Jan. 15, 2010).
Yu et al., "mTOR, a novel target in breast cancer: the effect of CCI-779, an mTOR inhibitor, in preclinical models of breast cancer," Endocrine-Related Cancer, 8:249-258 (2001).
Zhou et al., "mTOR Inhibition Ameliorates Cognitive and Affective Deficits Caused By Disc1 Knockdown in Adult-Born Dentate Granule Neurons," Neuron, 77(4):647-654 (2013).
Nieratschker, et al., "Geonome-wide investigation of rare structural variants identifies VIPR2 as a new candidate gene for schizophrenia", Expert Rev. Neurother, 11(7), 937-941 (2011).
Gong, et al.,, "Rattus norvegicus ER membrane protein complex subunit 10 (Emc10) mRNA", GenBank accession No. NM_001004221.2, Jun. 18, 2015, accessed and retrieved from www.ncbi.nlm.nih.gov on Sep. 14, 2015.
International Search Report dated Feb. 20 2014 in PCT/US13/69741.

\* cited by examiner

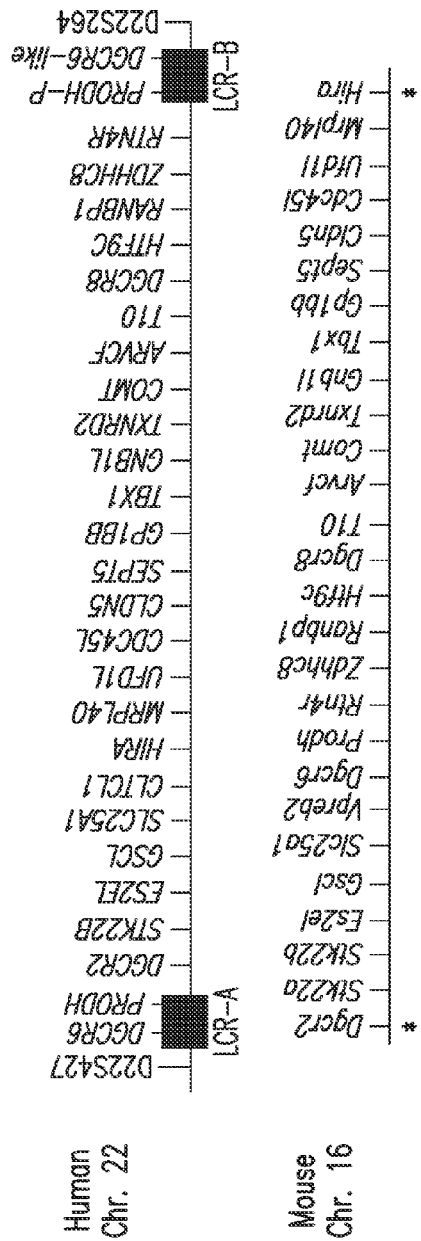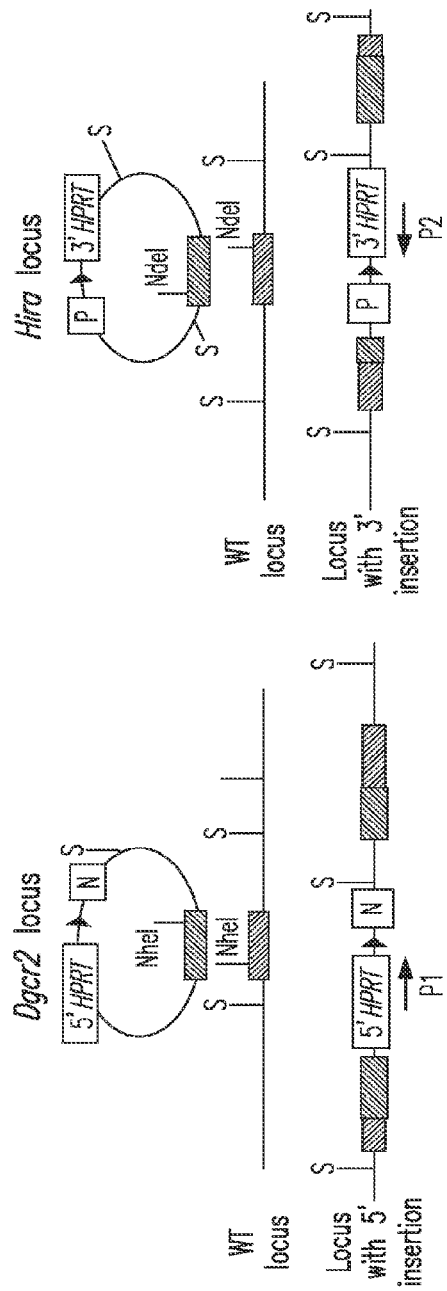
FIG. 1A
FIG. 1B

| | E17 PFC | | | P6 PFC | | | Adult PFC | |
|---|---|---|---|---|---|---|---|---|
| AffyID | Symbols | P.Value | AffyID | Symbols | P.Value | AffyID | Symbols | P.Value |
| 1450625_at | Col5a2 | 1.15E-04 | 1424038_a_at | 2310044H10Rik | 9.08E-10 | 1455326_at | Clec16a | 1.38E-09 |
| 1430644_at | Wbscr25 | 1.92E-04 | 1428021_at | Mccc2 | 5.82E-05 | 1424038_a_at | 2310044H10Rik | 3.40E-09 |
| 1419147_at | Rec8 | 4.30E-04 | 1430976_a_at | Mrpl9 | 6.26E-05 | 1456488_at | Wdr33 | 4.36E-09 |
| 1419028_at | Arpp21 | 4.49E-04 | 1438967_x_at | Amhr2 | 9.71E-05 | 1428208_at | Bcl7a | 1.06E-08 |
| 1427083_a_at | Map4k5 | 4.79E-04 | 1427962_at | Ccdc102a | 1.03E-04 | 1437125_at | Camk2a | 3.73E-08 |
| 1440240_at | Npb | 6.16E-04 | 1437236_a_at | Zfp110 | 1.49E-04 | 1439661_at | Slc16a14 | 3.76E-08 |
| 1421648_at | Nlgn1 | 6.30E-04 | 1451688_s_at | Cant1 | 1.76E-04 | 1426446_at | 6430548M08Rik | 6.03E-08 |
| 1424659_at | Slit2 | 8.03E-04 | 1453380_a_at | Xrcc6bp1 | 1.77E-04 | 1458870_x_at | Mycbp2 | 1.04E-07 |
| 1458119_at | Slc25a27 | 8.84E-04 | 1420117_at | Golph3 | 2.04E-04 | 1452322_a_at | Brwd1 | 1.32E-07 |
| 1449914_at | Ribc1 | 9.42E-04 | 1431678_at | 4930556N08Rik | 2.32E-04 | 1450661_x_at | Nfic | 1.61E-07 |

| | E17 HPC | | | P6 HPC | | | Adult HPC | |
|---|---|---|---|---|---|---|---|---|
| AffyID | Symbols | P.Value | AffyID | Symbols | P.Value | AffyID | Symbols | P.Value |
| 1450625_at | Col5a2 | 4.40E-05 | 1460613_x_at | Gh | 8.98E-05 | 1455326_at | Clec16a | 8.58E-10 |
| 1460245_at | Klrd1 | 2.84E-04 | 1424038_a_at | 2310044H10Rik | 1.68E-04 | 1423125_at | Dclk1 | 2.98E-09 |
| 1460451_at | Tmem52 | 2.96E-04 | 1418547_at | Tpi2 | 2.42E-04 | 1425690_at | B3gat1 | 3.94E-09 |
| 1453816_at | Nsa2 | 4.81E-04 | 1460471_at | Ooep | 3.33E-04 | 1424038_a_at | 2310044H10Rik | 1.81E-08 |
| 1420170_at | Myh9 | 5.38E-04 | 1418541_at | Cenpo | 3.44E-04 | 1441312_at | Cnnm1 | 4.33E-08 |
| 1434423_at | Gulp1 | 5.72E-04 | 1427202_at | 4833442J19Rik | 4.12E-04 | 1449931_at | Cpeb4 | 4.44E-08 |
| 1442160_at | Fam19a3 | 5.73E-04 | 1438624_x_at | Hs3st2 | 4.66E-04 | 1421200_at | Dlg2 | 9.01E-08 |
| 1422263_at | Bdkrb2 | 8.09E-04 | 1421298_a_at | Hipk1 | 4.75E-04 | 1421339_at | Extl3 | 1.10E-07 |
| 1416529_at | Emp1 | 8.99E-04 | 1449191_at | Wfdc12 | 4.87E-04 | 1431254_at | Kbtbd11 | 1.40E-07 |
| 1418710_at | Cd59a | 9.23E-04 | 1454576_at | A230102O21Rik | 5.02E-04 | 1452742_at | Trak1 | 1.45E-07 |

FIG. 4B (SEQ ID NO:3)

```
ttcctcccgg cgtgctccgc ggctcttggc tcacagccgt cccttcgctg gtgggaagaa 61
gccgagatgg cggcagccag cgctggggca acccggctgc tcctgctctt gctgatggcg 121
gtagcagcgc ccagtcgagc ccggggcagc ggctgccggg cggggactgg tgcgcgaggg 181
gctggggcgg aaggtcgaga gggcgaggcc tgtggcacgg tggggctgct gctggagcac 241
tcatttgaga tcgatgacag tgccaacttc cggaagcggg gctcactgct ctggaaccag 301
caggatggta ccttgtccct gtcacagcgg cagctcagcg aggaggagcg gggccgactc 361
cgggatgtgg cagccctgaa tggcctgtac cgggtccgga tcccaaggcg acccggggcc 421
ctggatggcc tggaagctgg tggctatgtc tcctcctttg tccctgcgtg ctccctggtg 481
gagtcgcacc tgtcggacca gctgaccctg cacgtggatg tggccggcaa cgtggtgggc 541
gtgtcggtgg tgacgcaccc cggggctgc cggggccatg aggtggagga cgtggacctg 601
gagctgttca acacctcggt gcagctgcag ccgcccacca cagccccagg ccctgagacg 661
gcggccttca ttgagcgcct ggagatggaa caggcccaga aggccaagaa ccccaggag 721
cagaagtcct tcttcgccaa atactggatg tacatcattc ccgtcgtcct gttcctcatg 781
atgtcaggag cgccagacac cggggccag ggtgggggtg gggtggggg tggtggtggg 841
ggtagtggcc ggtgagggcc caggctggtc agcgtcccgt cttcacacc caggggcctc 901
cctttctgct ggagtcccct gtgtcctcag ccatcccaag aagggtttgc tggtccctcc 961
tttccccccg tcccacgagg ccacctgggc cagccccttg tcctctgcct tctgctggca 1021
gaggagcagc tggactgggg cctttggcac agcagccggt gtctcctgcg cccgcctccc 1081
ccatggcccc atgcagcccc aggggcttcc cccctgccca tggagtagag cccgagatcc 1141
tggccactat gccagttctg acctcgcatc ccctaccc gagcccatgc agtctgggaa 1201
catgccgcct tctctccagc ctctgtgcct tgttccagg tggtctcacc ctcctgtccc 1261
tggctgggct aggtggtcct gtccaggctc ctgcagcgcc cccctcactt gacactgga 1321
ctaggatgca gcctcccttc tgtgtcccct tgagggtacc ctgggtcccc tcatcagggg 1381
cagaggcatg aaagagtcgg ggctggatgg ccgggggctt ctgggcccga cgcctagtgc 1441
agccctggg gtcgtggttt gacatttgtc tgcctggtgc aaacaaggaa tccttgcctt 1501
taaggtgaca ggccctccac aggcttccag acttgaagga aaaggtttaa gaaagaaaac 1561
aaaaccaaca gttagtggag tcaaagccca gacactgtaa atagaaccc ctccaccacc 1621
ccccgccgcc cagcatccta cctggactgc ggtgctacga gggcctgcgg gcctttgctg 1681
tgtgccaccc tccctgtaag tctatttaaa aacatcgacg atacattgaa atgtgtgaac 1741
gtttttgaaaa gctacagctt ccagcagcca aaagcaactg ttgttttggc aagacggtcc 1801
tgatgtacaa gcttgattga aattcactgc tcacttgata cgttattcag aaacccaagg 1861
aatggctgtc cccatcctca tgtggctgtg tggagctcag ctgtgttgtg tggcagttta 1921
ttaaactgtc ccccagatcg acacgcaaaa aaaaaaaaa a
```

FIG. 16A (SEQ ID NO:5)

```
   1 ttcctcccgg cgtgctccgc ggctcttggc tcacagccgt cccttcgctg gtgggaagaa
  61 gccgagatgg cggcagccag cgctggggca acccggctgc tcctgctctt gctgatggcg
 121 gtagcagcgc ccagtcgagc ccggggcagc ggctgccggg ccgggactgg tgcgcgaggg
 181 gctggggcgg aaggtcgaga gggcgaggcc tgtggcacgg tggggctgct gctggagcac
 241 tcatttgaga tcgatgacag tgccaacttc cggaagcggg gctcactgct ctggaaccag
 301 caggatggta ccttgtccct gtcacagcgg cagctcagcg aggaggagcg gggccgactc
 361 cgggatgtgg cagccctgaa tggcctgtac cgggtccgga tccaaggcg acccggggcc
 421 ctggatggcc tggaagctgg tgctatgtc tcctcctttg tcctgcgtg ctccctggtg
 481 gagtcgcacc tgtcggacca gctgaccctg cacgtggatg tggccggcaa cgtggtgggc
 541 gtgtcggtgg tgacgcaccc cggggctgc cggggccatg aggtggagga cgtggacctg
 601 gagctgttca cacctcggt gcagctgcag ccgcccacca cagccccagg ccctgagacg
 661 gcggccttca ttgagcgcct ggagatggaa caggcccaga aggccaagaa ccccaggag
 721 cagaagtcct tcttcgccaa atactggcac atcatcctgg gggggccgt gttgctcaca
 781 gccctgcgtc ctgctgcgcc agggcccgcg ccaccgccac aggaggcctg atggatgtac
 841 atcattcccg tcgtcctgtt cctcatgatg tcaggagcgc cagacaccgg ggccagggt
 901 ggggtgggg gtggggtgg tggtggggt agtggccggt gagggcccag gctggtcagc
 961 gtccgtctt gcacacccag gggcctccct ttctgctgga gtccctgtg tcctcagcca
1021 tcccaagaag ggtttgctgg tccctccttt cccccgtcc cacgaggcca cctgggccag
1081 cccttgtcc tctgccttct gctggcagag gagcagctgg actggggcct ttggcacagc
1141 agccggtgtc tcctgcgccc gcctccccca tggccccatg cagccccagg ggcttccccc
1201 ctgcccatgg agtagagccc gagatcctgg ccactatgcc agtctgacc tcgcatcccc
1261 ctaccccgag cccatgcagt ctgggaacat gccgccttct ctccagcctc tgtgcctttg
1321 ttccaggtgg tctcaccctc ctgtccctgg ctgggctagg tggtcctgtc caggctcctg
1381 cagcgccccc ctcactttga cactggacta ggatgcagcc tcccttctgt gtcccttga
1441 gggtaccctg ggtcccctca tcaggggcag aggcatgaaa gagtcggggc tggatggccg
1501 ggggcttctg ggcccgacgc ctagtgcagc cctggggtc gtggtttgac atttgtctgc
1561 ctggtgcaaa caaggaatcc ttgcctttaa ggtgacaggc cctccacagg cttccagact
1621 tgaaggaaaa ggtttaagaa agaaaacaaa accaacagtt agtggagtca aagcccagac
1681 actgtaaata gaacccctc caccacccc cgccgcccag catcctacct ggactgcggt
1741 gctacgaggg cctgcgggcc tttgctgtgt gccaccctcc ctgtaagtct atttaaaaac
1801 atcgacgata cattgaaatg tgtgaacgtt ttgaaaagct acagcttcca gcagccaaaa
1861 gcaactgttg ttttggcaag acggtcctga tgtacaagct tgattgaaat tcactgctca
1921 cttgatacgt tattcagaaa cccaaggaat ggctgtcccc atcctcatgt ggctgtgtgg
1981 agctcagctg tgttgtgtgg cagtttatta aactgtcccc cagatcgaca cgcaaaaaaa
2041 aaaaaaaa
```

FIG. 16B (SEQ ID NO:19)

```
   1 gagaaatggc cgccctgact gcgggagcag cggacgggc gctagtgcgc aggcgcggcg
  61 tgcggcgcag gcgcgtgagc ctcaggatga accctgtgtt tcctagcggg ctgtatggct
 121 ctcggttttt ctcaacgctc ccgtatggtg gccgcgggtg ccggggtgac ccggctgcta
 181 gtgctcttgc tgatggtagc cgcggctcct agcagagccc gaggcagcgg ctgccgggtc
 241 ggggcctccg cgcgtgggac cggggccgat ggccgtgaag ctgagggctg tggcaccgtg
 301 gctttgctgc tgagcattc atttgagctc ggtgatggag ccaacttcca gaagcgaggc
 361 ttgctgctct ggaaccagca ggatggcacc ctgtcggcaa cacagcgaca gctcagtgag
 421 gaggagcgtg gccgactccg ggatgtggct gctgtcaatg gcctctacag ggtccgggtc
 481 ccgaggcggc ctggacact tgatggttca gaagctggcg gccatgtgtc ttccttcgtc
 541 ccagcgtgct ccctggtgga gtcgcacctt tcggaccagc tgaccttgca cgtggatgtg
 601 gctggcaacg tggtgggcct gtctgtggtg gtgtaccctg ggggctgccg gggctccgag
 661 gtggaagatg aggacctgga gctgttcaat acatctgtgc agctgcggcc tcccagcact
 721 gctccaggcc ccgagactgc agccttcatt gagcgcctgg agatggagca ggcccagaag
 781 gccaagaacc cacaggagca gaagtctttc tttgccaaat actggatgta catcattcca
 841 gttgtgctgt tcctcatgat gtcgggagcg ccggacgctg ggggccaggg cggcggtggg
 901 ggcgggggca gcagccggtg agcagctgtg ccacctagag ccccccccag agccagccca
 961 agaaggagtt cctgtcccca catttcccta ttgcatgaat atggaaggct gtcccttcag
1021 tgagccctct ggccttcctg taagcccctc tttctgtccc tgagcctctc tctcatcctg
1081 ttgactgaga gcttgggtgg acctccctgt agccagctca ctgcaactgt gtcccaccat
1141 gtggcactgt gctcctctgt ctctaaaca cccaccagcc tgccccaccc caccccacca
1201 tacactttgg gaacttgcca agctctctcc agcctctgtg cctttgccct gcaggccccg
1261 tgcgcccctc actgtcactc tccagccctt gccaaggat ctgtggccca gaggcctctg
1321 ctcttagtgg ctaggtcagc ctccagccca ctgtccaggt ggcatgctgt cttctttgcc
1381 cccctctctg gtgccccaga ataccatggt gacctaccac tatcctttct gcctttggat
1441 gtcatagcct ggatctgtca ccaggagagg attgtgggcc tccacgttag tctgtgaatg
1501 cacacttcga gtgacttgtg tgcaggtttt gagagccggt tttgcactag ctgctcgaca
1561 gctgctggca tggccgtgct cttgcacatg cgccgctgtg ggcatgggga ttgctgtgca
1621 gcctcagctg tgttgtgtgg ctgctgatta aactgtcccc taaacagcca ctcttcagct
1681 cacttcctgc cttctgtgct tgtgaatagt cctgagttgc cgctgtggtt tgcctggttt
1741 atgtttgaat ggctttctta gggtatgtta cagaggggtg cctgagcaga ttaaagttgc
1801 tgtgagcaag gacgccttcc gaactctggg aggaggctgg ttcctgaccc tccta
```

FIG. 16C

List of transcripts outside the 22q11.2 syntenic region significantly misregulated in a reciprocal manner in both PFC and HPC

| | | | | PFC | | | | HPC | | | |
|---|---|---|---|---|---|---|---|---|---|---|---|
| AffyID | Chr | Chr_start | Chr_end | Fold change (Del/Bal)* | Fold change (Dup/Bal)* | F | P Value | Fold change (Del/Bal)* | Fold change (Dup/Bal)* | F | P Value | Symbols |
| 1424038_a_at | 7 | 51745308 | 51751883 | 1.43 | 0.86 | 73.00 | 2.6E-11 | 1.29 | 0.88 | 68.49 | 1.1E-10 | 2310044H10Rik |
| 1435179_at | 13 | 83867710 | 83875274 | 1.46 | 0.89 | 52.60 | 8.5E-10 | 1.42 | 0.95 | 45.42 | 6.4E-09 | C130071C03Rik (mir-9-2) |
| 1460033_at | 1 | 196850302 | 196864096 | 1.76 | 0.85 | 44.49 | 4.6E-09 | 1.71 | 0.86 | 42.71 | 1.1E-08 | A330023F24Rik (mir-29c) |
| 1435089_at | 13 | 63116293 | 63400964 | 1.77 | 0.78 | 43.72 | 5.5E-09 | 1.41 | 0.82 | 43.86 | 8.9E-09 | 2010111O1Rik (mir-23b) |
| 1428562_at | 11 | 75275040 | 75280192 | 1.33 | 0.85 | 42.88 | 6.7E-09 | 1.33 | 0.92 | 30.51 | 2.4E-07 | 2210403K04Rik (mir-22) |
| 1440357_at | 15 | 85537748 | 85537832 | 2.07 | 0.87 | 32.51 | 9.4E-08 | 1.68 | 0.81 | 46.73 | 3.3E-09 | (let-7b) |
| 1438838_at | X | 100764843 | 100819093 | 1.30 | 0.88 | 18.77 | 9.6E-06 | 1.30 | 0.93 | 19.90 | 7.7E-06 | B230206F22Rik (mir-374) |
| 1431094_at | 12 | 110833610 | 110835408 | 1.20 | 0.91 | 17.13 | 1.9E-05 | 1.20 | 0.87 | 25.24 | 1.2E-06 | 1110006E14Rik (mir-136) |
| 1457030_at | 12 | 110973190 | 110987665 | 1.29 | 0.91 | 14.82 | 5.3E-05 | 1.22 | 0.80 | 9.73 | 7.9E-04 | Mirg |
| 1434730_at | 7 | 86676773 | 86677477 | 1.42 | 0.96 | 14.75 | 5.5E-05 | 1.40 | 0.95 | 13.99 | 9.2E-05 | AI854517 (mir-9-3) |
| 1427410_at | 14 | 62221673 | 62301210 | 1.27 | 0.90 | 13.75 | 8.8E-05 | 1.49 | 0.95 | 33.16 | 1.2E-07 | Dleu2 (mir-15a) |
| 1442913_at | 3 | 118242789 | 118243450 | 1.31 | 0.92 | 9.92 | 6.4E-04 | 1.39 | 0.84 | 22.06 | 3.5E-06 | AK141880 |

* Bal = mouse strain balanced for copy number; Del = mouse model of the 22q11.2 microdeletion; Dup = mouse model of the 22q11.2 microduplication

FIG. 20

Three factor ANOVA of the impact of *mir-185*, *mir-485* and *mir-491* on luciferase activity, related to Figure 4.

| FACTOR | DF | SS | MS | F | Pr > F |
|---|---|---|---|---|---|
| pre_mir_185 | 1 | 0.582 | 0.582 | 6554 | 0 |
| pre_mir_491 | 1 | 0.0307 | 0.0307 | 346.3 | 0 |
| pre_mir_185*pre_mir_491 | 1 | 0.0062 | 0.0062 | 70.27 | 0 |
| pre_mir_485 | 1 | 0.0011 | 0.0011 | 12.86 | 0.0059 |
| pre_mir_185*pre_mir_485 | 1 | 0.0008 | 0.0008 | 9.069 | 0.0147 |
| pre_mir_485*pre_mir_491 | 1 | 2.50E-05 | 2.50E-05 | 0.282 | 0.6084 |

FIG. 21

List of transcripts outside the 22q11.2 syntenic region misregulated in a reciprocal manner

| Brain region | AffyID | Chr | Chr_start | Chr_end | Fold change (Del/Bal)* | Fold change (Dup/Bal)* | F | P Value | Symbols |
|---|---|---|---|---|---|---|---|---|---|
| PFC | 1424038_a_at | 7 | 51745308 | 51751883 | 1.43 | 0.86 | 73 | 2.60E-11 | 2310044H10Rik |
| PFC | 1435179_at | 13 | 83367710 | 83875274 | 1.46 | 0.89 | 52.6 | 8.50E-10 | C130071C03Rik (miR-9-2) |
| PFC | 1460033_at | 1 | 196850302 | 196864096 | 1.76 | 0.85 | 44.49 | 4.60E-09 | A330023F24Rik (miR-29c) |
| PFC | 1435089_at | 13 | 63116293 | 63400964 | 1.77 | 0.78 | 43.72 | 5.50E-09 | 2010111I01Rik (miR-23b) |
| PFC | 1428562_at | 11 | 75275040 | 75280192 | 1.33 | 0.85 | 42.88 | 6.70E-09 | 2210403K04Rik (miR-22) |
| PFC | 1440357_at | 15 | 85537748 | 85537832 | 2.07 | 0.87 | 32.51 | 9.40E-08 | (let-7b) |
| PFC | 1436838_at | X | 100764843 | 100819093 | 1.3 | 0.88 | 18.77 | 9.60E-06 | B230206F22Rik (miR-374) |
| PFC | 1431094_at | 12 | 110833610 | 110835408 | 1.2 | 0.91 | 17.13 | 1.90E-05 | 1110006E14Rik (miR-136) |
| PFC | 1439305_at | X | 100772966 | 100773671 | 1.4 | 0.97 | 15.3 | 4.20E-05 | (miR-374) |
| PFC | 1430959_at | 17 | 17967938 | 17976035 | 1.46 | 0.88 | 14.93 | 5.00E-05 | Ncrna00085 |
| PFC | 1456904_at | 11 | 97049276 | 97050652 | 0.82 | 1.08 | 14.92 | 5.10E-05 | NA |
| PFC | 1457030_at | 12 | 110973190 | 110987665 | 1.29 | 0.91 | 14.82 | 5.30E-05 | Mirg |
| PFC | 1434730_at | 7 | 86676773 | 86677477 | 1.42 | 0.96 | 14.75 | 5.50E-05 | AB054517 (miR-9-3) |
| PFC | 1427410_at | 12 | 62221673 | 62301210 | 1.27 | 0.9 | 13.75 | 8.80E-05 | Dleu2 (miR-15a) |
| PFC | 1419161_e_at | 14 | 94395304 | 94547116 | 1.17 | 0.97 | 13.66 | 9.20E-05 | Nox4 |
| PFC | 1441666_at | 1 | 148274740 | 148342171 | 0.81 | 1.02 | 13.48 | 1.00E-04 | AK162963 |
| PFC | 1453713_s_at | 17 | 17967938 | 17976035 | 1.8 | 0.89 | 13.18 | 1.20E-04 | Ncrna00085 |
| PFC | 1457181_at | 15 | 81822952 | 81846570 | 0.84 | 1.16 | 12.67 | 1.50E-04 | Pppde2 |
| PFC | 1438053_at | 16 | 56690444 | 56717467 | 0.71 | 1.06 | 11.63 | 2.60E-04 | Tfg |
| PFC | 1431343_at | 14 | 8603700 | 8625033 | 1.16 | 0.91 | 11.59 | 2.60E-04 | Gm10044 |
| PFC | 1430603_at | 9 | 98462878 | 98464030 | 0.93 | 1.25 | 11.14 | 3.30E-04 | 4930579K19Rik |
| PFC | 1459704_at | 11 | 100447804 | 100448219 | 0.85 | 1.05 | 10.91 | 3.70E-04 | Dnajc7 |
| PFC | 1457760_at | 4 | 131435283 | 131436411 | 0.7 | 1.04 | 10.8 | 4.00E-04 | A930004J17Rik |
| PFC | 1425173_s_at | 3 | 95392880 | 95423164 | 1.03 | 0.82 | 10.4 | 4.90E-04 | Golph3l |
| PFC | 1419586_at | X | 19941733 | 19977475 | 0.78 | 1.03 | 10.36 | 5.00E-04 | Rp2h |

FIG. 27

| | | | | | | | |
|---|---|---|---|---|---|---|---|
| PFC | 1453087_at | 5 | 139475528 | 139476533 | 0.91 | 1.08 | 10.35 | 5.10E-04 | 6330403J08Rik |
| PFC | 1420483_at | 1 | 36568720 | 36585082 | 1.23 | 0.94 | 10.07 | 5.90E-04 | Cnnm3 |
| PFC | 1436503_at | 6 | 128499839 | 128531624 | 1.1 | 0.87 | 9.98 | 6.20E-04 | BC048546 |
| PFC | 1417272_at | 5 | 65361313 | 65433140 | 0.82 | 1.1 | 9.97 | 6.30E-04 | Fam114a1 |
| PFC | 1442913_at | 3 | 118247789 | 118243450 | 1.31 | 0.92 | 9.92 | 6.40E-04 | NA |
| PFC | 1437686_x_at | 5 | 136750114 | 137043301 | 1.2 | 0.95 | 9.79 | 6.90E-04 | Cux1 |
| PFC | 1429599_a_at | 5 | 91360221 | 91450395 | 1.26 | 0.98 | 9.79 | 6.90E-04 | Mlhfd2l |
| PFC | 1424291_at | 8 | 96738500 | 96838966 | 1.23 | 0.98 | 9.77 | 7.00E-04 | Nup93 |
| PFC | 1427587_at | 7 | 6336027 | 6349347 | 0.98 | 0.97 | 9.48 | 8.30E-04 | Zfp28 |
| PFC | 1446835_at | 17 | 6109658 | 6110258 | 0.96 | 1.22 | 9.48 | 8.30E-04 | Tulp4 |
| PFC | 1429647_at | 1 | 89083240 | 89084978 | 0.93 | 1.31 | 9.38 | 8.80E-04 | 1700027L20Rik |
| PFC | 1452817_at | 1 | 180885169 | 181448134 | 0.94 | 1.25 | 9.37 | 8.80E-04 | Smyd3 |
| PFC | 1446932_at | 4 | 108470038 | 108470615 | 0.98 | 1.3 | 9.2 | 9.70E-04 | NA |
| HPC | 1424038_a_at | 7 | 51745308 | 51751883 | 1.29 | 0.88 | 68.49 | 1.10E-10 | 2310044H10Rik (let-7b) |
| HPC | 1440357_at | 15 | 85537748 | 85537832 | 1.68 | 0.81 | 48.73 | 3.30E-09 | C130071C03Rik (miR-9-2) |
| HPC | 1435179_at | 13 | 83867710 | 83875274 | 1.42 | 0.95 | 45.42 | 6.40E-09 | 2010111I01Rik (miR-23b) |
| HPC | 1435089_at | 13 | 63116293 | 63400964 | 1.41 | 0.82 | 43.86 | 8.90E-09 | A330023F24Rik (miR-29c) |
| HPC | 1460033_at | 1 | 196850302 | 196864096 | 1.71 | 0.86 | 42.71 | 1.10E-08 | Dleu2 (miR-15a) |
| HPC | 1427410_at | 14 | 62221673 | 62301210 | 1.49 | 0.95 | 33.16 | 1.20E-07 | 2210403K04Rik (miR-22) |
| HPC | 1428562_at | 11 | 75275040 | 75280192 | 1.33 | 0.92 | 30.51 | 2.40E-07 | 1110006E14Rik (miR-136) |
| HPC | 1431094_at | 12 | 110833610 | 110835408 | 1.2 | 0.87 | 25.24 | 1.20E-06 | AK141880 |
| HPC | 1442913_at | 3 | 118242789 | 118243450 | 1.39 | 0.84 | 22.06 | 3.50E-06 | B230206F22Rik (miR-374) |
| HPC | 1438838_at | X | 100764843 | 100819093 | 1.3 | 0.93 | 19.9 | 7.70E-06 | 2010111I01Rik |
| HPC | 1447298_at | 13 | 83979857 | 83880314 | 1.29 | 0.98 | 19.9 | 7.70E-06 | (miR-9-2) |
| HPC | 1436467_at | 9 | 41422406 | 41423268 | 1.2 | 0.83 | 15.31 | 5.10E-05 | D230004N17Rik (miR-125b-1) |
| HPC | 1424525_at | 18 | 66053147 | 66046233 | 1.06 | 0.83 | 14.34 | 7.80E-05 | Grp |
| HPC | 1434730_at | 7 | 86676773 | 86677477 | 1.4 | 0.95 | 13.99 | 9.20E-05 | AI854517 (miR-9-3) |
| HPC | 1460695_a_at | 13 | 63116293 | 63400964 | 1.11 | 0.89 | 13.92 | 9.40E-05 | 2010111I01Rik |

FIG. 27 (Cont.)

| | | | | | | | |
|---|---|---|---|---|---|---|---|
| HPC | 1455965_at | 1 | 173180552 | 173190053 | 0.75 | 13.5 | 1.20E-04 | Adamts4 |
| HPC | 1428792_at | 2 | 170172490 | 170253345 | 0.8 | 13.37 | 1.20E-04 | Bcas1 |
| HPC | 1458783_at | 11 | 22753661 | 22754585 | 1.19 | 13.05 | 1.40E-04 | B3gnt2 |
| HPC | 1459340_at | 3 | 94771437 | 94772099 | 1.25 | 12.96 | 1.50E-04 | NA |
| HPC | 1453184_at | 11 | 61497911 | 61523452 | 1.22 | 11.96 | 2.40E-04 | Fam83g |
| HPC | 1419148_at | 10 | 126437764 | 126458050 | 1.15 | 11.45 | 3.20E-04 | Avil |
| HPC | 1430600_at | 14 | 55555306 | 55558114 | 0.81 | 11.27 | 3.50E-04 | Cmtm5 |
| HPC | 1445039_at | 1 | 120955632 | 120956425 | 0.9 | 11.21 | 3.60E-04 | NA |
| HPC | 1426852_x_at | 15 | 54577482 | 54585316 | 1.11 | 11.15 | 3.70E-04 | Nov |
| HPC | 1440109_at | 7 | 54261880 | 54262492 | 0.88 | 10.94 | 4.10E-04 | D7Ertd413e |
| HPC | 1436796_at | 18 | 35721811 | 35751699 | 0.88 | 10.91 | 4.20E-04 | Motr3 |
| HPC | 1454212_x_at | 15 | 63712281 | 63720628 | 0.86 | 10.71 | 4.60E-04 | Gsdmcl2 |
| HPC | 1432862_at | 2 | 146909611 | 146911081 | 0.89 | 10.37 | 5.60E-04 | Mx2-4 |
| HPC | 1439943_at | 11 | 21138891 | 21221136 | 0.8 | 10.27 | 5.90E-04 | Vps54 |
| HPC | 1426851_a_at | 15 | 54577482 | 54585316 | 1.12 | 9.98 | 6.90E-04 | Nov |
| HPC | 1449465_at | 5 | 21390271 | 21850523 | 1.14 | 9.95 | 7.00E-04 | Reln |
| HPC | 1415951_at | 11 | 100277007 | 100286153 | 0.95 | 9.84 | 7.50E-04 | Fkbp10 |
| HPC | 1459493_at | 18 | 79083283 | 79083977 | 1.21 | 9.83 | 7.50E-04 | Setbp1 |
| HPC | 1419411_at | 10 | 127162447 | 127168824 | 1.2 | 9.76 | 7.80E-04 | Tac2 |
| HPC | 1435047_at | 13 | 110844396 | 111070414 | 1.03 | 9.74 | 7.90E-04 | Rab3c |
| HPC | 1457030_at | 12 | 110973190 | 110987665 | 0.9 | 9.73 | 7.90E-04 | Mrg |
| HPC | 1438748_at | 19 | 60600598 | 60656926 | 0.85 | 9.62 | 8.40E-04 | 2700078E11Rik |
| HPC | 1422703_at | X | 82947275 | 83022158 | 1.15 | 9.39 | 9.60E-04 | Gyk |

* Bal = mouse strain balanced for copy number; Del = mouse model of the 22q11.2 microdeletion; Dup = mouse model of the 22q11.2 microduplication

FIG. 27 (Cont.)

Gene Expression profile of predicted mir-185 targets that have Golgi related functions

| Rank | AffyID | Gene Symbols | P.Value | logFC |
|---|---|---|---|---|
| 31 | 1425690_at | B3gat1 | 3.94E-09 | 0.478 |
| 52 | 1420833_at | Vamp2 | 2.92E-07 | 0.607 |
| 66 | 1425691_at | B3gat1 | 6.47E-07 | 0.319 |
| 70 | 1421270_at | Sh3rf1 | 7.53E-07 | 0.391 |
| 117 | 1421890_at | St3gal2 | 3.97E-06 | 0.292 |
| 176 | 1423228_at | B4galt6 | 1.23E-05 | 0.286 |
| 192 | 1450105_at | Adam10 | 1.48E-05 | 0.28 |
| 199 | 1422758_at | Chst2 | 1.57E-05 | 0.296 |
| 201 | 1421271_at | Sh3rf1 | 1.58E-05 | 0.276 |
| 216 | 1450913_at | B4galt6 | 1.80E-05 | 0.291 |
| 340 | 1448367_at | Sdf4 | 5.34E-05 | 0.267 |
| 458 | 1450153_at | Gopc | 9.82E-05 | 0.233 |
| 493 | 1421978_at | Gad2 | 1.16E-04 | 0.437 |
| 535 | 1431646_a_at | Stx6 | 1.42E-04 | 0.215 |
| 647 | 1422718_at | Ap3s2 | 2.27E-04 | 0.236 |
| 726 | 1450247_a_at | Scamp5 | 3.09E-04 | 0.255 |
| 730 | 1449111_a_at | Grb2 | 3.13E-04 | 0.217 |
| 734 | 1423720_a_at | Sar1a | 3.16E-04 | 0.292 |
| 825 | 1428398_at | B3galt5 | 4.25E-04 | 0.224 |
| 845 | 1416437_a_at | Mapk8ip3 | 4.48E-04 | 0.238 |
| 914 | 1431320_a_at | Myo5a | 5.23E-04 | 0.179 |
| 923 | 1427481_a_at | Atp1a3 | 5.33E-04 | 0.198 |
| 1018 | 1421891_at | St3gal2 | 6.61E-04 | 0.194 |
| 1029 | 1449943_at | Lfng | 6.74E-04 | 0.312 |
| 1155 | 1422664_at | Rab10 | 8.79E-04 | 0.183 |
| 1270 | 1437107_at | Rab6b | 1.08E-03 | 0.395 |
| 1304 | 1426744_at | Srebf2 | 1.14E-03 | 0.295 |
| 1338 | 1428374_at | Glce | 1.20E-03 | 0.164 |
| 1354 | 1438373_at | App | 1.22E-03 | -0.21 |
| 1387 | 1431120_a_at | Golga1 | 1.28E-03 | 0.259 |
| 1430 | 1420643_at | Lfng | 1.37E-03 | 0.283 |
| 1450 | 1419190_at | Vti1a | 1.41E-03 | 0.217 |
| 1464 | 1424633_at | Camk1g | 1.44E-03 | 0.161 |
| 1502 | 1443220_at | NA | 1.50E-03 | 0.217 |
| 1589 | 1422044_at | Ndst1 | 1.68E-03 | 0.352 |
| 1694 | 1429296_at | Rab10 | 1.93E-03 | 0.166 |
| 1739 | 1433571_at | Serinc5 | 2.05E-03 | -0.245 |
| 1805 | 1449129_a_at | Kcnip3 | 2.18E-03 | 0.161 |
| 1822 | 1420262_at | NA | 2.25E-03 | -0.203 |
| 2003 | 1448309_at | Ap3m1 | 2.74E-03 | 0.196 |
| 2042 | 1423075_at | Lman2 | 2.85E-03 | 0.17 |
| 2217 | 1431053_at | Mphosph9 | 3.37E-03 | 0.257 |

FIG. 28

| | | | | |
|---|---|---|---|---|
| 2246 | 1435758_at | B4galt6 | 3.45E-03 | 0.158 |
| 2257 | 1424755_at | Hip1 | 3.51E-03 | 0.264 |
| 2414 | 1416550_at | Slc35b4 | 4.08E-03 | 0.135 |
| 2516 | 1432017_at | Hip1 | 4.47E-03 | -0.146 |
| 2712 | 1436321_at | B3gnt7 | 5.02E-03 | -0.185 |
| 2740 | 1432054_at | Golga1 | 5.13E-03 | 0.244 |
| 2995 | 1451484_a_at | Syn1 | 6.13E-03 | 0.13 |
| 3025 | 1452174_at | Srebf2 | 6.30E-03 | 0.132 |
| 3093 | 1439853_at | B4galnt2 | 6.58E-03 | -0.181 |
| 3148 | 1455924_at | Rab6b | 6.85E-03 | 0.145 |
| 3281 | 1431066_at | Fut11 | 7.49E-03 | 0.187 |
| 3345 | 1450730_at | Hs2st1 | 7.76E-03 | 0.177 |
| 3358 | 1450104_at | Adam10 | 7.83E-03 | 0.144 |
| 3427 | 1457356_at | NA | 8.17E-03 | -0.17 |
| 3683 | 1416459_at | Arf2 | 9.41E-03 | 0.119 |
| 3710 | 1428397_at | B3galt5 | 9.58E-03 | 0.156 |
| 3722 | 1460191_at | Ykt6 | 9.65E-03 | 0.144 |
| 3788 | 1436155_at | Nmnat2 | 1.01E-02 | 0.145 |
| 3822 | 1457045_at | Galnt13 | 1.03E-02 | 0.251 |
| 3826 | 1423743_at | Arcn1 | 1.03E-02 | 0.148 |
| 3969 | 1448477_at | Chst12 | 1.10E-02 | 0.113 |
| 3986 | 1415670_at | Copg | 1.11E-02 | 0.124 |
| 3998 | 1419754_at | Myo5a | 1.12E-02 | 0.134 |
| 4049 | 1444943_at | NA | 1.14E-02 | -0.184 |
| 4089 | 1423358_at | Ece2 | 1.16E-02 | -0.207 |
| 4101 | 1444413_at | Ap3s2 | 1.17E-02 | 0.255 |
| 4459 | 1436525_at | Ap3s2 | 1.39E-02 | 0.135 |
| 4584 | 1455986_at | Zdhhc17 | 1.48E-02 | 0.245 |
| 4608 | 1423229_at | Inpp5e | 1.49E-02 | 0.119 |
| 4656 | 1436193_at | Man1c1 | 1.52E-02 | 0.099 |
| 4708 | 1435762_at | Pacs1 | 1.55E-02 | 0.153 |
| 4795 | 1453095_at | Rab10 | 1.60E-02 | 0.094 |
| 4866 | 1434945_at | Lpcat2 | 1.66E-02 | -0.1 |
| 4905 | 1443398_at | NA | 1.68E-02 | 0.308 |
| 5038 | 1426575_at | Sgms1 | 1.77E-02 | 0.185 |
| 5075 | 1449063_at | Sec22b | 1.80E-02 | 0.125 |
| 5154 | 1440684_at | Lpcat2 | 1.85E-02 | -0.121 |
| 5157 | 1460329_at | B4galt6 | 1.85E-02 | 0.086 |
| 5225 | 1443842_at | Arfgef2 | 1.90E-02 | 0.133 |
| 5582 | 1430966_at | Cml3 | 2.16E-02 | -0.158 |
| 5633 | 1460070_at | NA | 2.20E-02 | 0.13 |
| 5663 | 1455735_at | Ap1s3 | 2.22E-02 | 0.129 |
| 5664 | 1418508_a_at | Grb2 | 2.22E-02 | 0.101 |
| 5671 | 1425363_at | B4galnt1 | 2.22E-02 | -0.122 |
| 5681 | 1422468_at | Ppt1 | 2.23E-02 | 0.133 |

FIG. 28 (Cont.)

| | | | | |
|---|---|---|---|---|
| 5811 | 1416549_at | Slc35b4 | 2.33E-02 | 0.107 |
| 5837 | 1422129_at | Apc2 | 2.36E-02 | 0.114 |
| 5882 | 1425539_a_at | Rtn3 | 2.40E-02 | 0.108 |
| 6004 | 1447834_at | NA | 2.51E-02 | -0.162 |
| 6169 | 1423167_at | Mobkl3 | 2.63E-02 | 0.117 |
| 6247 | 1445103_at | NA | 2.70E-02 | -0.101 |
| 6461 | 1454865_at | Slc9a8 | 2.88E-02 | 0.11 |
| 6526 | 1424112_at | Igf2r | 2.94E-02 | 0.126 |
| 6637 | 1451837_at | Ap3b2 | 3.04E-02 | -0.111 |
| 6756 | 1459801_at | B3galt5 | 3.16E-02 | -0.185 |
| 6868 | 1457316_at | Mtap6 | 3.24E-02 | 0.133 |
| 6882 | 1428150_at | Coro7 | 3.26E-02 | 0.105 |
| 6950 | 1426704_at | Gak | 3.33E-02 | -0.118 |
| 6971 | 1426576_at | Sgms1 | 3.35E-02 | 0.113 |
| 7015 | 1426274_at | Slc9a8 | 3.39E-02 | 0.194 |
| 7049 | 1453221_at | Gopc | 3.42E-02 | 0.095 |
| 7088 | 1450729_at | Hs2st1 | 3.45E-02 | 0.116 |
| 7283 | 1458363_at | Zdhhc17 | 3.61E-02 | 0.114 |
| 7303 | 1423152_at | Vapb | 3.63E-02 | 0.314 |
| 7426 | 1429661_at | Rhobtb3 | 3.74E-02 | 0.173 |
| 7435 | 1431136_at | Rab36 | 3.75E-02 | 0.141 |
| 7450 | 1447012_at | Gm10791 | 3.76E-02 | -0.127 |
| 7669 | 1459144_at | NA | 3.97E-02 | -0.093 |
| 7928 | 1426703_at | Gak | 4.23E-02 | 0.092 |
| 7956 | 1418582_at | Cbfa2t3 | 4.26E-02 | 0.102 |
| 8007 | 1458501_at | Vapb | 4.31E-02 | 0.169 |
| 8158 | 1428149_at | Coro7 | 4.48E-02 | 0.162 |
| 8286 | 1460322_at | Chst3 | 4.60E-02 | -0.114 |
| 8611 | 1448308_at | Ap3m1 | 4.93E-02 | 0.094 |
| 8746 | 1419189_at | Vti1a | 5.07E-02 | 0.079 |
| 8831 | 1450384_at | Bace1 | 5.15E-02 | 0.086 |
| 8939 | 1423038_at | Stx6 | 5.28E-02 | 0.078 |
| 8968 | 1442028_at | B4galnt2 | 5.30E-02 | -0.138 |
| 9185 | 1458189_at | Emid2 | 5.57E-02 | -0.111 |
| 9251 | 1448464_at | Ykt6 | 5.63E-02 | 0.087 |
| 9285 | 1439610_at | Rab27b | 5.68E-02 | 0.128 |
| 9324 | 1441216_at | St3gal1 | 5.73E-02 | -0.124 |
| 9331 | 1421825_at | Bace1 | 5.74E-02 | 0.116 |
| 9491 | 1425876_a_at | Glce | 5.92E-02 | 0.174 |
| 9552 | 1424856_at | Atp1a3 | 5.98E-02 | -0.098 |
| 9608 | 1442234_at | Chst2 | 6.05E-02 | 0.127 |
| 9850 | 1416548_at | Slc35b4 | 6.36E-02 | 0.098 |
| 9907 | 1435718_at | Ap3s2 | 6.42E-02 | 0.069 |
| 9932 | 1416375_at | Ap3m1 | 6.45E-02 | 0.163 |
| 10029 | 1421892_at | St3gal2 | 6.58E-02 | 0.117 |

FIG. 28 (Cont.)

| | | | | |
|---|---|---|---|---|
| 10410 | 1424708_at | Tmed10 | 7.12E-02 | 0.159 |
| 10733 | 1416374_at | Ap3m1 | 7.55E-02 | 0.087 |
| 10817 | 1450509_at | Chst11 | 7.66E-02 | 0.126 |
| 10868 | 1454821_at | B3gat1 | 7.75E-02 | 0.077 |
| 10928 | 1436676_at | Mapk8ip3 | 7.84E-02 | −0.092 |
| 11304 | 1435199_at | Apc2 | 8.31E-02 | 0.182 |
| 11552 | 1415958_at | Slc2a4 | 8.65E-02 | −0.131 |
| 11608 | 1452471_at | Il17rd | 8.73E-02 | −0.13 |
| 11746 | 1443857_at | Hook3 | 8.90E-02 | 0.138 |
| 11832 | 1436471_at | Rab36 | 9.03E-02 | −0.073 |
| 11896 | 1445688_at | NA | 9.12E-02 | −0.093 |
| 11919 | 1419909_at | Mphosph9 | 9.17E-02 | −0.094 |
| 12475 | 1433630_at | Map6d1 | 9.98E-02 | 0.068 |
| 12508 | 1428044_at | Ap3s2 | 1.00E-01 | −0.102 |
| 12518 | 1428902_at | Chst11 | 1.00E-01 | 0.084 |
| 12643 | 1417215_at | Rab27b | 1.02E-01 | 0.104 |
| 12745 | 1460083_at | Adam10 | 1.04E-01 | −0.073 |
| 12789 | 1423759_a_at | Tmco1 | 1.04E-01 | 0.078 |
| 12811 | 1435801_at | Fktn | 1.05E-01 | 0.101 |
| 12906 | 1427020_at | Scara3 | 1.06E-01 | 0.125 |
| 12922 | 1430549_at | Bet1l | 1.07E-01 | 0.107 |
| 13027 | 1425316_at | B3gat1 | 1.08E-01 | −0.106 |
| 13056 | 1446049_at | NA | 1.09E-01 | −0.096 |
| 13109 | 1418946_at | St3gal1 | 1.09E-01 | 0.091 |
| 13608 | 1453227_at | Rhobtb3 | 1.17E-01 | 0.105 |
| 13625 | 1437748_at | Fut11 | 1.17E-01 | 0.103 |
| 13687 | 1418929_at | Ift57 | 1.18E-01 | 0.084 |
| 13889 | 1419186_a_at | St8sia4 | 1.22E-01 | −0.075 |
| 13935 | 1447656_at | Zdhhc17 | 1.22E-01 | −0.109 |
| 13967 | 1418655_at | B4galnt1 | 1.23E-01 | 0.106 |
| 13968 | 1423647_a_at | Zdhhc3 | 1.23E-01 | 0.063 |
| 14000 | 1448404_at | Scamp2 | 1.23E-01 | 0.139 |
| 14073 | 1438008_at | Gga3 | 1.25E-01 | 0.094 |
| 14264 | 1440011_at | NA | 1.27E-01 | −0.176 |
| 14265 | 1445374_at | NA | 1.28E-01 | −0.07 |
| 14657 | 1451036_at | Spg21 | 1.34E-01 | 0.105 |
| 14708 | 1420928_at | St6gal1 | 1.35E-01 | 0.093 |
| 14715 | 1428367_at | Ndst1 | 1.35E-01 | 0.092 |
| 14960 | 1439094_at | Cltc | 1.39E-01 | −0.116 |
| 15016 | 1450528_at | B3galt5 | 1.40E-01 | 0.129 |
| 15062 | 1451017_at | Ergic3 | 1.40E-01 | −0.064 |
| 15117 | 1421853_at | Psen1 | 1.41E-01 | 0.072 |
| 15173 | 1450844_at | Stx6 | 1.43E-01 | 0.06 |
| 15267 | 1452657_at | Ap1s2 | 1.44E-01 | 0.054 |
| 15301 | 1438063_at | Mphosph9 | 1.45E-01 | 0.107 |
| 15413 | 1458296_at | NA | 1.47E-01 | −0.147 |

FIG. 28 (Cont.)

| | | | | |
|---|---|---|---|---|
| 15447 | 1443881_at | Pofut1 | 1.48E-01 | 0.064 |
| 15609 | 1442463_at | NA | 1.50E-01 | 0.101 |
| 15617 | 1456655_at | NA | 1.50E-01 | -0.09 |
| 15685 | 1424111_at | Igf2r | 1.52E-01 | 0.062 |
| 15742 | 1442904_at | Chst2 | 1.53E-01 | -0.144 |
| 16001 | 1415766_at | Sec22b | 1.57E-01 | 0.075 |
| 16220 | 1439922_at | Prrc1 | 1.61E-01 | 0.117 |
| 16277 | 1421155_at | B3galt6 | 1.62E-01 | 0.067 |
| 16372 | 1424707_at | Tmed10 | 1.64E-01 | 0.063 |
| 16416 | 1435679_at | Optn | 1.65E-01 | -0.075 |
| 16561 | 1418544_at | Kcnip3 | 1.67E-01 | 0.055 |
| 16664 | 1447347_at | NA | 1.69E-01 | -0.117 |
| 16694 | 1454982_at | Arfgef2 | 1.69E-01 | 0.064 |
| 16773 | 1435982_at | Stx12 | 1.71E-01 | -0.065 |
| 17109 | 1434123_at | Fut11 | 1.77E-01 | -0.052 |
| 17199 | 1440585_at | Stx6 | 1.78E-01 | -0.086 |
| 17742 | 1429778_at | Optn | 1.90E-01 | 0.114 |
| 18074 | 1420621_a_at | App | 1.96E-01 | 0.054 |
| 18150 | 1417327_at | Cav2 | 1.97E-01 | 0.093 |
| 18184 | 1440014_at | NA | 1.98E-01 | -0.102 |
| 18225 | 1455368_at | Zdhhc3 | 1.99E-01 | 0.074 |
| 18374 | 1440979_at | Igf2r | 2.02E-01 | -0.047 |
| 18470 | 1446737_a_at | Hook3 | 2.04E-01 | 0.095 |
| 18685 | 1436051_at | Myo5a | 2.08E-01 | 0.057 |
| 18823 | 1442079_at | Sgms1 | 2.11E-01 | -0.058 |
| 18878 | 1416086_at | Tpst2 | 2.12E-01 | 0.059 |
| 19009 | 1423168_at | Mobkl3 | 2.14E-01 | 0.046 |
| 19055 | 1425549_at | Psen1 | 2.15E-01 | 0.07 |
| 19058 | 1420832_at | Qsox1 | 2.15E-01 | -0.061 |
| 19193 | 1448936_at | Stx12 | 2.19E-01 | 0.054 |
| 19621 | 1440963_at | Cbfa2t3 | 2.28E-01 | -0.069 |
| 19946 | 1445009_at | NA | 2.34E-01 | -0.072 |
| 20048 | 1420016_at | Ppt1 | 2.37E-01 | -0.063 |
| 20091 | 1426393_a_at | Sdf4 | 2.37E-01 | 0.066 |
| 20302 | 1426886_at | Cln5 | 2.42E-01 | -0.072 |
| 20382 | 1440915_at | Mphosph9 | 2.44E-01 | 0.108 |
| 20406 | 1422467_at | Ppt1 | 2.44E-01 | 0.057 |
| 20483 | 1438566_at | St8sia6 | 2.46E-01 | -0.08 |
| 20589 | 1427442_a_at | App | 2.49E-01 | 0.041 |
| 20638 | 1431325_at | Cml3 | 2.50E-01 | 0.083 |
| 20681 | 1420112_at | NA | 2.51E-01 | -0.054 |
| 20768 | 1444275_at | NA | 2.52E-01 | -0.07 |
| 21064 | 1452515_a_at | Xylt2 | 2.60E-01 | -0.063 |
| 21300 | 1420927_at | St6gal1 | 2.65E-01 | 0.075 |
| 21507 | 1446617_at | NA | 2.70E-01 | -0.066 |

FIG. 28 (Cont.)

| | | | | |
|---|---|---|---|---|
| 21565 | 1460436_at | Ndst1 | 2.72E-01 | 0.05 |
| 21605 | 1458920_at | NA | 2.73E-01 | 0.116 |
| 21742 | 1415696_at | Sar1a | 2.76E-01 | 0.057 |
| 21867 | 1418129_at | Dhcr24 | 2.80E-01 | 0.137 |
| 21870 | 1455584_at | Sdf4 | 2.80E-01 | 0.053 |
| 22017 | 1432230_at | Hip1 | 2.83E-01 | −0.069 |
| 22036 | 1446696_at | Ift57 | 2.84E-01 | −0.123 |
| 22131 | 1434397_at | Zdhhc17 | 2.86E-01 | 0.051 |
| 22165 | 1455741_a_at | Ece1 | 2.87E-01 | 0.05 |
| 22331 | 1436192_at | Arfgef2 | 2.91E-01 | 0.058 |
| 22341 | 1460431_at | Gcnt1 | 2.91E-01 | 0.095 |
| 22363 | 1440905_at | Hs2st1 | 2.91E-01 | −0.077 |
| 22645 | 1436664_a_at | Slc35a2 | 2.98E-01 | 0.042 |
| 22797 | 1425031_at | Fktn | 3.02E-01 | 0.051 |
| 22906 | 1451215_at | Prrc1 | 3.05E-01 | 0.048 |
| 23037 | 1451089_a_at | Arcn1 | 3.08E-01 | 0.035 |
| 23265 | 1439876_at | Vti1a | 3.14E-01 | −0.061 |
| 23269 | 1430904_at | Arfgap3 | 3.14E-01 | −0.075 |
| 23324 | 1436062_at | Arcn1 | 3.15E-01 | 0.045 |
| 23558 | 1436956_at | NA | 3.22E-01 | −0.053 |
| 23566 | 1436101_at | NA | 3.22E-01 | 0.044 |
| 23601 | 1453858_at | Slc35a2 | 3.23E-01 | −0.044 |
| 23760 | 1424746_at | Kif1c | 3.27E-01 | 0.069 |
| 23774 | 1439877_at | NA | 3.27E-01 | −0.098 |
| 23978 | 1449538_a_at | Gcnt1 | 3.32E-01 | −0.06 |
| 24169 | 1458524_at | Fndc3a | 3.37E-01 | −0.073 |
| 24233 | 1457968_at | NA | 3.38E-01 | 0.064 |
| 24321 | 1440457_at | NA | 3.41E-01 | −0.056 |
| 24330 | 1450137_at | Pofut1 | 3.41E-01 | 0.054 |
| 24445 | 1421609_a_at | Cml3 | 3.44E-01 | 0.048 |
| 24546 | 1422687_at | Nras | 3.47E-01 | 0.041 |
| 24588 | 1418774_a_at | Atp7a | 3.48E-01 | −0.077 |
| 24690 | 1435157_at | Hook3 | 3.51E-01 | 0.034 |
| 24721 | 1432631_at | Prrc1 | 3.51E-01 | −0.06 |
| 24887 | 1434316_at | NA | 3.56E-01 | −0.055 |
| 24932 | 1420821_at | Sgpp1 | 3.57E-01 | −0.1 |
| 24999 | 1440340_at | B3galt6 | 3.59E-01 | −0.062 |
| 25088 | 1434557_at | Hip1 | 3.61E-01 | 0.055 |
| 25240 | 1425128_at | B3gnt8 | 3.65E-01 | −0.075 |
| 25460 | 1439433_a_at | Slc35a2 | 3.71E-01 | 0.074 |
| 25610 | 1422622_at | Nos3 | 3.75E-01 | 0.076 |
| 25660 | 1458342_at | Tmem90a | 3.76E-01 | 0.078 |
| 25735 | 1443863_at | Fndc3a | 3.78E-01 | −0.039 |
| 25921 | 1424747_at | Kif1c | 3.82E-01 | −0.043 |
| 25932 | 1426903_at | Fndc3a | 3.83E-01 | 0.038 |

FIG. 28 (Cont.)

| | | | | |
|---|---|---|---|---|
| 26127 | 1455826_a_at | Bace1 | 3.88E-01 | 0.055 |
| 26230 | 1446314_at | Gcnt7 | 3.92E-01 | -0.053 |
| 26239 | 1450399_at | Psen1 | 3.92E-01 | 0.035 |
| 26692 | 1423074_at | Lman2 | 4.05E-01 | 0.036 |
| 26788 | 1453393_a_at | Chst4 | 4.07E-01 | -0.037 |
| 26884 | 1417730_at | Ext1 | 4.10E-01 | 0.046 |
| 27080 | 1425955_at | Cav2 | 4.15E-01 | -0.053 |
| 27188 | 1434914_at | Rab6b | 4.18E-01 | 0.033 |
| 27310 | 1424894_at | Rab13 | 4.20E-01 | 0.037 |
| 27493 | 1444873_at | NA | 4.25E-01 | -0.048 |
| 27548 | 1439899_at | Galnt13 | 4.27E-01 | -0.06 |
| 27767 | 1458608_at | NA | 4.33E-01 | -0.046 |
| 27770 | 1423230_at | Inpp5e | 4.33E-01 | 0.055 |
| 27794 | 1444705_at | NA | 4.34E-01 | -0.071 |
| 28091 | 1439417_at | Qsox1 | 4.43E-01 | 0.051 |
| 28164 | 1416828_at | Snap25 | 4.45E-01 | -0.035 |
| 28323 | 1440386_at | Glce | 4.50E-01 | -0.038 |
| 28342 | 1459654_at | NA | 4.50E-01 | 0.043 |
| 28620 | 1444563_at | NA | 4.58E-01 | -0.045 |
| 28728 | 1431761_at | Entpd4 | 4.61E-01 | -0.048 |
| 28771 | 1441423_at | Ece1 | 4.62E-01 | -0.048 |
| 28825 | 1426372_a_at | Bet1l | 4.64E-01 | 0.026 |
| 29026 | 1451224_at | Scamp5 | 4.70E-01 | 0.031 |
| 29052 | 1444361_at | Ap1s2 | 4.71E-01 | 0.05 |
| 29079 | 1428147_at | Coro7 | 4.71E-01 | 0.038 |
| 29100 | 1420902_at | St6galnac3 | 4.72E-01 | 0.065 |
| 29292 | 1422550_a_at | Mtap6 | 4.78E-01 | 0.033 |
| 29339 | 1438661_a_at | Arf2 | 4.79E-01 | 0.054 |
| 29538 | 1439196_at | Hook3 | 4.85E-01 | 0.045 |
| 29727 | 1454626_at | Cltc | 4.91E-01 | 0.025 |
| 29739 | 1458084_at | Zdhhc17 | 4.91E-01 | -0.029 |
| 30054 | 1454077_at | Vti1a | 5.00E-01 | -0.03 |
| 30521 | 1418195_at | Galnt10 | 5.12E-01 | 0.056 |
| 30636 | 1458897_at | Ust | 5.16E-01 | 0.036 |
| 30681 | 1422980_a_at | Bet1l | 5.18E-01 | 0.038 |
| 31145 | 1459097_at | NA | 5.32E-01 | 0.038 |
| 31455 | 1427617_at | Fut10 | 5.41E-01 | -0.032 |
| 31508 | 1435027_at | Golga1 | 5.43E-01 | 0.022 |
| 31615 | 1459707_at | NA | 5.46E-01 | -0.027 |
| 31807 | 1426325_at | Kif1c | 5.51E-01 | 0.034 |
| 32077 | 1444102_at | NA | 5.60E-01 | 0.033 |
| 32304 | 1438355_at | Tmem90a | 5.67E-01 | 0.029 |
| 32464 | 1446624_at | Fktn | 5.72E-01 | -0.037 |
| 32703 | 1421522_at | B4galnt2 | 5.79E-01 | -0.038 |
| 32779 | 1439218_at | NA | 5.81E-01 | -0.049 |

FIG. 28 (Cont.)

| | | | | |
|---|---|---|---|---|
| 32833 | 1415959_at | Slc2a4 | 5.83E-01 | -0.038 |
| 32882 | 1437388_at | Fut10 | 5.84E-01 | 0.035 |
| 32946 | 1416591_at | Rab34 | 5.86E-01 | -0.028 |
| 32960 | 1416590_a_at | Rab34 | 5.87E-01 | -0.024 |
| 33007 | 1416760_at | Galntl1 | 5.88E-01 | 0.023 |
| 33138 | 1432819_at | Prrc1 | 5.93E-01 | -0.032 |
| 33158 | 1416611_at | Scamp2 | 5.94E-01 | 0.022 |
| 33175 | 1447235_at | NA | 5.94E-01 | 0.033 |
| 33517 | 1455149_at | Sh3rf1 | 6.04E-01 | 0.035 |
| 33813 | 1432818_at | Prrc1 | 6.14E-01 | 0.029 |
| 34235 | 1421824_at | Bace1 | 6.27E-01 | 0.018 |
| 34412 | 1445505_at | Ndst1 | 6.32E-01 | 0.023 |
| 34607 | 1436865_at | Slc26a11 | 6.39E-01 | -0.032 |
| 34680 | 1431549_at | NA | 6.41E-01 | -0.038 |
| 34744 | 1416017_at | Copg | 6.44E-01 | 0.022 |
| 34779 | 1436499_at | Sgms1 | 6.45E-01 | 0.026 |
| 34819 | 1452365_at | Csgalnact1 | 6.47E-01 | 0.027 |
| 34832 | 1454924_at | Fut10 | 6.47E-01 | 0.027 |
| 34887 | 1451825_a_at | Copz1 | 6.49E-01 | -0.017 |
| 35005 | 1441133_at | NA | 6.52E-01 | -0.023 |
| 35022 | 1429589_at | Gad2 | 6.52E-01 | -0.019 |
| 35229 | 1429652_at | Prrc1 | 6.59E-01 | 0.026 |
| 35272 | 1430391_a_at | St8sia4 | 6.60E-01 | 0.029 |
| 35397 | 1453032_at | Mobkl3 | 6.64E-01 | 0.019 |
| 35670 | 1420333_at | Txndc8 | 6.74E-01 | 0.028 |
| 35685 | 1441993_at | Ap3s2 | 6.75E-01 | -0.019 |
| 35814 | 1458616_at | NA | 6.80E-01 | 0.019 |
| 35954 | 1416199_at | Kifc3 | 6.84E-01 | -0.021 |
| 36001 | 1444884_at | Ppt1 | 6.86E-01 | 0.019 |
| 36267 | 1445966_at | NA | 6.95E-01 | -0.029 |
| 36278 | 1418014_a_at | B4galt1 | 6.95E-01 | 0.022 |
| 36301 | 1421967_at | B4galt5 | 6.96E-01 | 0.025 |
| 36355 | 1441148_at | NA | 6.98E-01 | 0.027 |
| 36408 | 1459970_at | NA | 7.00E-01 | -0.021 |
| 36487 | 1437998_at | Ap1s2 | 7.03E-01 | -0.02 |
| 36607 | 1458773_at | NA | 7.07E-01 | -0.021 |
| 36699 | 1453929_at | Rnf24 | 7.10E-01 | 0.032 |
| 36742 | 1438252_at | Qsox1 | 7.12E-01 | -0.014 |
| 36795 | 1425310_a_at | Emid2 | 7.13E-01 | -0.021 |
| 36894 | 1417214_at | Rab27b | 7.16E-01 | 0.022 |
| 37011 | 1454060_a_at | Nras | 7.20E-01 | 0.022 |
| 37023 | 1445178_at | Sh3rf1 | 7.20E-01 | 0.05 |
| 37039 | 1451895_a_at | Dhcr24 | 7.21E-01 | -0.015 |
| 37096 | 1420261_at | Psen1 | 7.23E-01 | -0.015 |
| 37194 | 1422739_at | Hs2st1 | 7.26E-01 | 0.022 |

FIG. 28 (Cont.)

| | | | | |
|---|---|---|---|---|
| 37503 | 1420831_at | Qsox1 | 7.35E-01 | -0.026 |
| 37522 | 1427923_at | Zmpste24 | 7.36E-01 | 0.018 |
| 37524 | 1419910_at | Mphosph9 | 7.36E-01 | -0.019 |
| 37638 | 1424058_at | Prrc1 | 7.41E-01 | -0.021 |
| 37757 | 1458054_at | Ext1 | 7.45E-01 | -0.022 |
| 37768 | 1456147_at | St8sia6 | 7.45E-01 | 0.035 |
| 37836 | 1429893_at | Il17rd | 7.47E-01 | 0.019 |
| 38090 | 1446739_at | NA | 7.56E-01 | 0.023 |
| 38187 | 1458258_at | NA | 7.60E-01 | 0.012 |
| 38215 | 1447763_at | NA | 7.61E-01 | -0.017 |
| 38284 | 1436797_a_at | Surf4 | 7.63E-01 | 0.016 |
| 38293 | 1440493_at | Galnt10 | 7.63E-01 | -0.02 |
| 38312 | 1460036_at | Ap1s2 | 7.64E-01 | -0.052 |
| 38364 | 1440092_at | NA | 7.66E-01 | -0.028 |
| 38429 | 1444411_at | NA | 7.68E-01 | -0.025 |
| 38435 | 1419320_at | Chst5 | 7.69E-01 | -0.02 |
| 38548 | 1418130_at | Dhcr24 | 7.73E-01 | -0.015 |
| 38586 | 1436224_at | Kif1c | 7.74E-01 | 0.019 |
| 38629 | 1423646_at | Zdhhc3 | 7.76E-01 | -0.011 |
| 38767 | 1438705_at | Cbfa2t3 | 7.80E-01 | 0.017 |
| 38795 | 1442365_at | NA | 7.81E-01 | -0.019 |
| 38806 | 1440121_at | NA | 7.82E-01 | 0.032 |
| 38913 | 1421517_at | St6galnac1 | 7.85E-01 | -0.011 |
| 39243 | 1426927_at | Ap3b2 | 7.98E-01 | -0.011 |
| 39548 | 1424561_at | Ece2 | 8.08E-01 | -0.014 |
| 39772 | 1418101_a_at | Rtn3 | 8.15E-01 | -0.008 |
| 40008 | 1424979_at | Aph1a | 8.24E-01 | 0.014 |
| 40539 | 1423609_a_at | Mgat1 | 8.42E-01 | 0.007 |
| 40735 | 1415672_at | Golga7 | 8.48E-01 | -0.008 |
| 40782 | 1456323_at | Pofut1 | 8.50E-01 | -0.012 |
| 40839 | 1443082_at | NA | 8.52E-01 | -0.01 |
| 41035 | 1434862_at | Fut2 | 8.58E-01 | -0.009 |
| 41074 | 1428103_at | Adam10 | 8.59E-01 | -0.01 |
| 41243 | 1457009_at | Rhobtb3 | 8.65E-01 | 0.014 |
| 41365 | 1432533_a_at | Slc35a2 | 8.70E-01 | 0.009 |
| 41408 | 1436921_at | Atp7a | 8.71E-01 | 0.016 |
| 41588 | 1446365_at | Vti1a | 8.77E-01 | -0.014 |
| 41613 | 1420834_at | Vamp2 | 8.78E-01 | 0.007 |
| 41628 | 1451853_at | Fktn | 8.79E-01 | 0.007 |
| 41685 | 1452366_at | Csgalnact1 | 8.81E-01 | 0.008 |
| 41705 | 1435252_at | B3galt6 | 8.81E-01 | 0.008 |
| 41726 | 1438897_at | Zdhhc3 | 8.82E-01 | -0.009 |
| 41824 | 1457583_at | NA | 8.86E-01 | -0.012 |
| 42111 | 1425975_a_at | Mapk8ip3 | 8.96E-01 | -0.006 |
| 42167 | 1450246_at | Fut2 | 8.97E-01 | 0.006 |

FIG. 28 (Cont.)

| | | | | |
|---|---|---|---|---|
| 42229 | 1448255_a_at | Surf4 | 9.00E-01 | 0.006 |
| 42245 | 1449432_a_at | Mmel1 | 9.00E-01 | -0.006 |
| 42495 | 1443141_at | NA | 9.08E-01 | 0.005 |
| 42617 | 1450497_at | Apc2 | 9.13E-01 | -0.008 |
| 42710 | 1434177_at | Ece1 | 9.16E-01 | -0.006 |
| 42987 | 1445466_at | Map6d1 | 9.26E-01 | -0.007 |
| 43014 | 1445838_at | NA | 9.26E-01 | 0.004 |
| 43082 | 1431941_at | Slc35b4 | 9.29E-01 | 0.005 |
| 43387 | 1431205_at | Slc9a8 | 9.40E-01 | 0.004 |
| 43455 | 1430932_at | Slc9a8 | 9.43E-01 | 0.004 |
| 43457 | 1416458_at | Arf2 | 9.43E-01 | 0.004 |
| 43643 | 1418194_at | Galnt10 | 9.50E-01 | 0.003 |
| 43797 | 1458179_at | NA | 9.55E-01 | 0.003 |
| 43822 | 1422688_a_at | NA | 9.56E-01 | 0.003 |
| 44117 | 1442402_at | Sh3rf1 | 9.66E-01 | -0.003 |
| 44298 | 1455064_at | Rab36 | 9.72E-01 | -0.002 |
| 44305 | 1445224_at | NA | 9.73E-01 | 0.002 |
| 44314 | 1420903_at | St6galnac3 | 9.73E-01 | -0.002 |
| 44475 | 1451554_a_at | Aph1a | 9.78E-01 | -0.004 |
| 44677 | 1424756_at | Hip1 | 9.85E-01 | -0.001 |
| 44797 | 1449737_at | NA | 9.89E-01 | 0.001 |
| 44798 | 1458525_at | NA | 9.89E-01 | -0.001 |
| 44883 | 1443581_at | St6gal1 | 9.92E-01 | -0.001 |

FIG. 28 (Cont.)

SEQUENCE LISTING

<160> NUMBER OF SEQ ID NOS: 26

<210> SEQ ID NO 1
<211> LENGTH: 258
<212> TYPE: PRT
<213> ORGANISM: Mus musculus

<400> SEQUENCE: 1

Met Val Ala Ala Gly Ala Gly Val Thr Arg Leu Leu Val Leu Leu Leu
1               5                   10                  15

Met Val Ala Ala Ala Pro Ser Arg Ala Arg Gly Ser Gly Cys Arg Val
                20                  25                  30

Gly Ala Ser Ala Arg Gly Thr Gly Ala Asp Gly Arg Glu Ala Glu Gly
            35                  40                  45

Cys Gly Thr Val Ala Leu Leu Leu Glu His Ser Phe Glu Leu Gly Asp
50                  55                  60

Gly Ala Asn Phe Gln Lys Arg Gly Leu Leu Trp Asn Gln Gln Asp
65                  70                  75                  80

Gly Thr Leu Ser Ala Thr Gln Arg Gln Leu Ser Glu Glu Glu Arg Gly
                85                  90                  95

Arg Leu Arg Asp Val Ala Ala Val Asn Gly Leu Tyr Arg Val Arg Val
            100                 105                 110

Pro Arg Arg Pro Gly Thr Leu Asp Gly Ser Glu Ala Gly Gly His Val
            115                 120                 125

Ser Ser Phe Val Pro Ala Cys Ser Leu Val Glu Ser His Leu Ser Asp
130                 135                 140

Gln Leu Thr Leu His Val Asp Val Ala Gly Asn Val Val Gly Leu Ser
145                 150                 155                 160

Val Val Val Tyr Pro Gly Gly Cys Arg Gly Ser Val Glu Asp Glu
                165                 170                 175

Asp Leu Glu Leu Phe Asn Thr Ser Val Gln Leu Arg Pro Pro Ser Thr
            180                 185                 190

Ala Pro Gly Pro Glu Thr Ala Ala Phe Ile Glu Arg Leu Glu Met Glu
            195                 200                 205

Gln Ala Gln Lys Ala Lys Asn Pro Gln Glu Gln Lys Ser Phe Phe Ala
    210                 215                 220

Lys Tyr Trp Met Tyr Ile Ile Pro Val Val Leu Phe Leu Met Met Ser
225                 230                 235                 240

Gly Ala Pro Asp Ala Gly Gly Gln Gly Gly Gly Gly Gly Ser
                245                 250                 255

Ser Arg

<210> SEQ ID NO 2
<211> LENGTH: 262
<212> TYPE: PRT
<213> ORGANISM: Homo sapiens

<400> SEQUENCE: 2

Met Ala Ala Ala Ser Ala Gly Ala Thr Arg Leu Leu Leu Leu Leu Leu
1               5                   10                  15

Met Ala Val Ala Ala Pro Ser Arg Ala Arg Gly Ser Gly Cys Arg Ala
                20                  25                  30

Gly Thr Gly Ala Arg Gly Ala Gly Ala Glu Gly Arg Glu Gly Glu Ala
            35                  40                  45

Cys Gly Thr Val Gly Leu Leu Leu Glu His Ser Phe Glu Ile Asp Asp
50                  55                  60

```
Ser Ala Asn Phe Arg Lys Arg Gly Ser Leu Leu Trp Asn Gln Gln Asp
 65                  70                  75                  80

Gly Thr Leu Ser Leu Ser Gln Arg Gln Leu Ser Glu Glu Glu Arg Gly
                 85                  90                  95

Arg Leu Arg Asp Val Ala Ala Leu Asn Gly Leu Tyr Arg Val Arg Ile
            100                 105                 110

Pro Arg Arg Pro Gly Ala Leu Asp Gly Leu Glu Ala Gly Tyr Val
        115                 120                 125

Ser Ser Phe Val Pro Ala Cys Ser Leu Val Glu Ser His Leu Ser Asp
130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175

Asp Leu Glu Leu Phe Asn Thr Ser Val Gln Leu Gln Pro Pro Thr Thr
            180                 185                 190

Ala Pro Gly Pro Glu Thr Ala Ala Phe Ile Glu Arg Leu Glu Met Glu
        195                 200                 205

Gln Ala Gln Lys Ala Lys Asn Pro Gln Glu Gln Lys Ser Phe Phe Ala
210                 215                 220

Lys Tyr Trp Met Tyr Ile Ile Pro Val Val Leu Phe Leu Met Met Ser
225                 230                 235                 240

Gly Ala Pro Asp Thr Gly Gly Gln Gly Gly Gly Gly Gly Gly Gly Gly
                245                 250                 255

Gly Gly Gly Ser Gly Arg
            260

<210> SEQ ID NO 3
<211> LENGTH: 1961
<212> TYPE: DNA
<213> ORGANISM: Homo sapiens

<400> SEQUENCE: 3
ttcctcccgg cgtgctccgc ggctcttggc tcacagccgt cccttcgctg gtgggaagaa      60
gccgagatgg cggcagccag cgctggggca acccggctgc tcctgctctt gctgatggcg     120
gtagcagcgc ccagtcgagc ccggggcagc ggctgccggg ccgggactgg tgcgcgaggg     180 gctgggcgg aaggtcgaga gggcgaggcc tgtggcacgg tggggctgct gctggagcac     240
tcatttgaga tcgatgacag tgccaacttc cggaagcggg gctcactgct ctggaaccag     300
caggatggta ccttgtccct gtcacagcgg cagctcagcg aggaggagcg ggccgactc      360 cgggatgtgg cagccctgaa tggcctgtac cgggtccgga tcccaaggcg acccggggcc     420
ctggatggcc tggaagctgg tggctatgtc tcctcctttg tccctgcgtg ctccctggtg     480
gagtcgcacc tgtcggacca gctgaccctg cacgtggatg tggccggcaa cgtggtgggc     540
gtgtcggtgg tgacgcaccc cggggctgc cggggccatg aggtgaggga cgtggacctg     600
gagctgttca acacctcggt gcagctgcag ccgcccacca cagccccagg ccctgagacg     660
gcggccttca ttgagcgcct ggagatggaa caggcccaga aggccaagaa cccccaggag     720
cagaagtcct tcttcgccaa atactggatg tacatcattc ccgtcgtcct gttcctcatg     780
atgtcaggag cgccagacac cggggggcca ggtgggggtg gggtgggggg tggtggtggg     840
ggtagtggcc ggtgagggcc caggctggtc agcgtcccgt cttgcacacc caggggcctc     900
cctttctgct ggagtcccct gtgtcctcag ccatcccaag aagggtttgc tggtcccctcc    960
```

```
tttcccccg tcccacgagg ccacctgggc cagccccttg tcctctgcct tctgctggca    1020
gaggagcagc tggactgggg cctttggcac agcagccggt gtctcctgcg cccgcctccc    1080
ccatggcccc atgcagcccc aggggcttcc ccctgccca tggagtagag cccgagatcc     1140
tggccactat gccagttctg acctcgcatc ccctacccc gagcccatgc agtctgggaa     1200
catgccgcct tctctccagc ctctgtgcct ttgttccagg tggtctcacc ctcctgtccc    1260
tggctgggct aggtggtcct gtccaggctc ctgcagcgcc cccctcactt tgacactgga    1320
ctaggatgca gcctcccttc tgtgtcccct tgagggtacc ctgggtcccc tcatcagggg    1380
cagaggcatg aaagagtcgg ggctggatgg ccgggggctt ctgggcccga cgcctagtgc    1440
agcccctggg gtcgtggttt gacatttgtc tgcctggtgc aaacaaggaa tccttgcctt    1500
taaggtgaca ggccctccac aggcttccag acttgaagga aaggtttaa gaaagaaaac     1560 aaaaccaaca gttagtggag tcaaagccca gacactgtaa atagaacccc ctccaccacc    1620
ccccgccgcc cagcatccta cctggactgc ggtgctacga gggcctgcgg gcctttgctg    1680
tgtgccaccc tccctgtaag tctatttaaa acatcgacg atacattgaa atgtgtgaac      1740
gttttgaaaa gctacagctt ccagcagcca aaagcaactg ttgttttggc aagacggtcc    1800
tgatgtacaa gcttgattga aattcactgc tcacttgata cgttattcag aaacccaagg    1860
aatggctgtc cccatcctca tgtggctgtg tggagctcag ctgtgttgtg tggcagttta    1920
ttaaactgtc ccccagatcg acacgcaaaa aaaaaaaaa a                          1961

<210> SEQ ID NO 4
<211> LENGTH: 254
<212> TYPE: PRT
<213> ORGANISM: Homo sapiens

<400> SEQUENCE: 4

Met Ala Ala Ala Ser Ala Gly Ala Thr Arg Leu Leu Leu Leu Leu
1               5                   10                  15

Met Ala Val Ala Ala Pro Ser Arg Ala Arg Gly Ser Gly Cys Arg Ala
                20                  25                  30

Gly Thr Gly Ala Arg Gly Ala Gly Ala Glu Gly Arg Glu Gly Glu Ala
            35                  40                  45

Cys Gly Thr Val Gly Leu Leu Leu Glu His Ser Phe Glu Ile Asp Asp
        50                  55                  60

Ser Ala Asn Phe Arg Lys Arg Gly Ser Leu Leu Trp Asn Gln Gln Asp
65                  70                  75                  80

Gly Thr Leu Ser Leu Ser Gln Arg Gln Leu Ser Glu Glu Glu Arg Gly
                85                  90                  95

Arg Leu Arg Asp Val Ala Ala Leu Asn Gly Leu Tyr Arg Val Arg Ile
                100                 105                 110

Pro Arg Arg Pro Gly Ala Leu Asp Gly Leu Glu Ala Gly Gly Tyr Val
            115                 120                 125

Ser Ser Phe Val Pro Ala Cys Ser Leu Val Glu Ser His Leu Ser Asp
        130                 135                 140

Gln Leu Thr Leu His Val Asp Val Ala Gly Asn Val Val Gly Val Ser
145                 150                 155                 160

Val Val Thr His Pro Gly Gly Cys Arg Gly His Glu Val Glu Asp Val
                165                 170                 175

Asp Leu Glu Leu Phe Asn Thr Ser Val Gln Leu Gln Pro Pro Thr Thr
            180                 185                 190
```

Ala Pro Gly Pro Glu Thr Ala Ala Phe Ile Glu Arg Leu Glu Met Glu
            195                 200                 205

Gln Ala Gln Lys Ala Lys Asn Pro Gln Glu Gln Lys Ser Phe Phe Ala
    210                 215                 220

Lys Tyr Trp His Ile Ile Leu Gly Gly Ala Val Leu Leu Thr Ala Leu
225                 230                 235                 240

Arg Pro Ala Ala Pro Gly Pro Ala Pro Pro Gln Glu Ala
                245                 250

<210> SEQ ID NO 5
<211> LENGTH: 2048
<212> TYPE: DNA
<213> ORGANISM: Homo sapiens

<400> SEQUENCE: 5

| | | | | | |
|---|---|---|---|---|---|
| ttcctcccgg | cgtgctccgc | ggctcttggc | tcacagccgt | cccttcgctg | gtgggaagaa | 60 |
| gccgagatgg | cggcagccag | cgctggggca | acccggctgc | tcctgctctt | gctgatggcg | 120 |
| gtagcagcgc | ccagtcgagc | ccggggcagc | ggctgccggg | ccgggactgg | tgcgcgaggg | 180 |
| gctggggcgg | aaggtcgaga | gggcgaggcc | tgtggcacgg | tggggctgct | gctggagcac | 240 |
| tcatttgaga | tcgatgacag | tgccaacttc | cggaagcggg | gctcactgct | ctggaaccag | 300 |
| caggatggta | ccttgtccct | gtcacagcgg | cagctcagcg | aggaggagcg | gggccgactc | 360 |
| cgggatgtgc | agccctgaa | tggcctgtac | cgggtccgga | tcccaaggcg | acccggggcc | 420 |
| ctggatggcc | tggaagctgg | tggctatgtc | tcctcctttg | tcctgcgtg | ctccctggtg | 480 |
| gagtcgcacc | tgtcggacca | gctgaccctg | cacgtggatg | tggccggcaa | cgtggtgggc | 540 |
| gtgtcggtgg | tgacgcaccc | cggggctgc | cggggccatg | aggtggagga | cgtggacctg | 600 |
| gagctgttca | acacctcggt | gcagctgcag | ccgcccacca | cagccccagg | ccctgagacg | 660 |
| gcggccttca | ttgagcgcct | ggagatggaa | caggcccaga | aggccaagaa | ccccaggag | 720 |
| cagaagtcct | tcttcgccaa | atactggcac | atcatcctgg | ggggggccgt | gttgctcaca | 780 |
| gccctgcgtc | ctgctgcgcc | agggcccgcg | ccaccgccac | aggaggcctg | atggatgtac | 840 |
| atcattcccg | tcgtcctgtt | cctcatgatg | tcaggagcgc | cagacaccgg | gggccagggt | 900 |
| gggggtgggg | gtggggtgg | tggtgggggt | agtggccggt | gagggcccag | gctggtcagc | 960 |
| gtccgtcttt | gcacacccag | gggctccct | ttctgctgga | gtccctgtg | tcctcagcca | 1020 |
| tcccaagaag | ggtttgctgg | tccctccttt | ccccccgtcc | cacgaggcca | cctgggccag | 1080 |
| cccccttgtcc | tctgccttct | gctggcagag | gagcagctgg | actggggcct | ttggcacagc | 1140 |
| agccggtgtc | tcctgcgccc | gcctccccca | tggccccatg | cagccccagg | ggcttccccc | 1200 |
| ctgcccatgg | agtagagccc | gagatcctgg | ccactatgcc | agttctgacc | tcgcatcccc | 1260 |
| ctaccccgag | cccatgcagt | ctgggaacat | gccgccttct | ctccagcctc | tgtgcctttg | 1320 |
| ttccaggtgg | tctcaccctc | ctgtccctgg | ctgggctagg | tggtcctgtc | caggctcctg | 1380 |
| cagcgccccc | ctcactttga | cactggacta | ggatgcagcc | tccttctgt | gtccccttga | 1440 |
| gggtaccctg | ggtcccctca | tcaggggcag | aggcatgaaa | gagtcggggc | tggatggccg | 1500 |
| ggggcttctg | ggcccgacgc | ctagtgcagc | cctggggtc | gtggtttgac | atttgtctgc | 1560 |
| ctggtgcaaa | caaggaatcc | ttgcctttaa | ggtgacaggc | cctccacagg | cttccagact | 1620 |
| tgaaggaaaa | ggtttaagaa | agaaaacaaa | accaacagtt | agtggagtca | aagcccagac | 1680 |
| actgtaaata | gaaccccctc | caccaccccc | cgccgcccag | catcctacct | ggactgcggt | 1740 |
| gctacgaggg | cctgcgggcc | tttgctgtgt | gccaccctcc | ctgtaagtct | atttaaaaac | 1800 |

```
atcgacgata cattgaaatg tgtgaacgtt ttgaaaagct acagcttcca gcagccaaaa    1860
gcaactgttg ttttggcaag acggtcctga tgtacaagct tgattgaaat tcactgctca    1920
cttgatacgt tattcagaaa cccaaggaat ggctgtcccc atcctcatgt ggctgtgtgg    1980
agctcagctg tgttgtgtgg cagtttatta aactgtcccc cagatcgaca cgcaaaaaaa    2040
aaaaaaaa                                                              2048

<210> SEQ ID NO 6
<211> LENGTH: 65
<212> TYPE: DNA
<213> ORGANISM: Mus musculus

<400> SEQUENCE: 6
agggattgga gagaaaggca gttcctgatg gtcccctccc aggggctggc tttcctctgg    60
tcctt                                                                 65

<210> SEQ ID NO 7
<211> LENGTH: 65
<212> TYPE: RNA
<213> ORGANISM: Mus musculus

<400> SEQUENCE: 7
agggauugga gagaaaggca guuccugaug gucccCucCC aggggcuggc uuCCucugg     60 uccuu                                                                 65

<210> SEQ ID NO 8
<211> LENGTH: 22
<212> TYPE: RNA
<213> ORGANISM: Mus musculus

<400> SEQUENCE: 8
uggagagaaa ggcaguuccu ga                                              22

<210> SEQ ID NO 9
<211> LENGTH: 82
<212> TYPE: DNA
<213> ORGANISM: Homo sapiens

<400> SEQUENCE: 9 aggggggcgag ggattggaga gaaaggcagt tcctgatggt cccctcccca ggggctggct   60
ttcctctggt ccttccctcc ca                                              82

<210> SEQ ID NO 10
<211> LENGTH: 82
<212> TYPE: RNA
<213> ORGANISM: Homo sapiens

<400> SEQUENCE: 10 aggggggcgag ggauuggaga gaaaggcagu uccugauggu cccCucccca ggggcuggcu   60
uuccucuggu ccuucccucc ca                                              82

<210> SEQ ID NO 11
<211> LENGTH: 73
<212> TYPE: RNA
<213> ORGANISM: Mus musculus

<400> SEQUENCE: 11
acuuggagag aggcuggccg ugaugaauuc gauucaucua aacgagucau acacggcucu    60
```
ccucucuucu agu                                                          73

<210> SEQ ID NO 12
<211> LENGTH: 22
<212> TYPE: RNA
<213> ORGANISM: Mus musculus

<400> SEQUENCE: 12
agaggcuggc cgugaugaau uc                                                22

<210> SEQ ID NO 13
<211> LENGTH: 73
<212> TYPE: RNA
<213> ORGANISM: Homo sapiens

<400> SEQUENCE: 13
acuuggagag aggcuggccg ugaugaauuc gauucaucaa agcgagucau acacggcucu       60
ccucucuuuu agu                                                          73

<210> SEQ ID NO 14
<211> LENGTH: 22
<212> TYPE: RNA
<213> ORGANISM: Homo sapiens

<400> SEQUENCE: 14
agaggcuggc cgugaugaau uc                                                22

<210> SEQ ID NO 15
<211> LENGTH: 86
<212> TYPE: RNA
<213> ORGANISM: Mus musculus

<400> SEQUENCE: 15
aauugacuua gcugggaagu ggggaacccu uccaugagga guagaacacu ccuuaugcaa       60
gauucccuuc uaccugacug aguuga                                            86

<210> SEQ ID NO 16
<211> LENGTH: 22
<212> TYPE: RNA
<213> ORGANISM: Mus musculus

<400> SEQUENCE: 16 agugggggaac ccuuccauga gg                                               22

<210> SEQ ID NO 17
<211> LENGTH: 84
<212> TYPE: RNA
<213> ORGANISM: Homo sapiens

<400> SEQUENCE: 17
uugacuuagc uggguagugg ggaacccuuc caugaggagu agaacacucc uuaugcaaga       60
uucccuucua ccuggcuggg uugg                                              84

<210> SEQ ID NO 18
<211> LENGTH: 22
<212> TYPE: RNA
<213> ORGANISM: Homo sapiens

<400> SEQUENCE: 18 agugggggaac ccuuccauga gg                                               22

<210> SEQ ID NO 19
<211> LENGTH: 1855
<212> TYPE: DNA
<213> ORGANISM: Mus musculus

<400> SEQUENCE: 19

| | | | | | |
|---|---|---|---|---|---|
| gagaaatggc | cgccctgact | gcgggagcag | gcggacgggc | gctagtgcgc | aggcgcggcg | 60 |
| tgcggcgcag | gcgcgtgagc | ctcaggatga | accctgtgtt | tcctagcggg | ctgtatggct | 120 |
| ctcggttttt | ctcaacgctc | ccgtatggtg | gccgcgggtg | ccggggtgac | ccggctgcta | 180 |
| gtgctcttgc | tgatggtagc | cgcggctcct | agcagagccc | gaggcagcgg | ctgccgggtc | 240 |
| ggggcctccg | cgcgtgggac | cggggccgat | ggccgtgaag | ctgagggctg | tggcaccgtg | 300 |
| gctttgctgc | tggagcattc | atttgagctc | ggtgatggag | ccaacttcca | gaagcgaggc | 360 |
| ttgctgctct | ggaaccagca | ggatggcacc | ctgtcggcaa | cacagcgaca | gctcagtgag | 420 |
| gaggagcgtg | gccgactccg | ggatgtggct | gctgtcaatg | gcctctacag | ggtccgggtc | 480 |
| ccgaggcggc | ctgggacact | tgatggttca | gaagctggcg | gccatgtgtc | ttccttcgtc | 540 |
| ccagcgtgct | ccctggtgga | gtcgcacctt | tcggaccagc | tgaccttgca | cgtggatgtg | 600 |
| gctggcaacg | tggtgggcct | gtctgtggtg | gtgtaccctg | ggggctgccg | gggctccgag | 660 |
| gtggaagatg | aggacctgga | gctgttcaat | acatctgtgc | agctgcggcc | tcccagcact | 720 |
| gctccaggcc | ccgagactgc | agccttcatt | gagcgcctgg | agatggagca | ggcccagaag | 780 |
| gccaagaacc | acaggagca | gaagtctttc | tttgccaaat | actggatgta | catcattcca | 840 |
| gttgtgctgt | tcctcatgat | gtcgggagcg | ccggacgctg | ggggccaggg | cggcggtggg | 900 |
| ggcgggggca | gcagccggtg | agcagctgtg | ccacctagag | ccccccccag | agccagccca | 960 |
| agaaggagtt | cctgtcccca | catttcccta | ttgcatgaat | atggaaggct | gtcccttcag | 1020 |
| tgagccctct | ggccttcctg | taagcccctc | tttctgtccc | tgagcctctc | tctcatcctg | 1080 |
| ttgactgaga | gcttgggtgg | acctcccgt | agccagctca | ctgcaactgt | gtcccaccat | 1140 |
| gtggcactgt | gctcctctgt | ctgctaaaca | cccaccagcc | tgccccaccc | caccccacca | 1200 |
| tacactttgg | gaacttgcca | agctctctcc | agcctctgtg | cctttgccct | gcaggccccg | 1260 |
| tgcgcccctc | actgtcactc | tccagccctt | tgccaaggat | ctgtggccca | gaggcctctg | 1320 |
| ctcttagtgg | ctaggtcagc | ctccagccca | ctgtccaggt | ggcatgctgt | cttctttgcc | 1380 |
| cccctctctg | gtgccccaga | ataccatggt | gacctaccac | tatcctttct | gcctttggat | 1440 |
| gtcatagcct | ggatctgtca | ccaggagagg | attgtgggcc | tccacgttag | tctgtgaatg | 1500 |
| cacacttcga | gtgacttgtg | tgcaggtttt | gagagccggt | tttgcactag | ctgctcgaca | 1560 |
| gctgctggca | tggccgtgct | cttgcacatg | cgccgctgtg | ggcatgggga | ttgctgtgca | 1620 |
| gcctcagctg | tgttgtgtgg | ctgctgatta | aactgtcccc | taaacagcca | ctcttcagct | 1680 |
| cacttcctgc | cttctgtgct | tgtgaatagt | cctgagttgc | cgctgtggtt | tgcctggttt | 1740 |
| atgtttgaat | ggctttctta | gggtatgtta | cagaggggtg | cctgagcaga | ttaaagttgc | 1800 |
| tgtgagcaag | gacgccttcc | gaactctggg | aggaggctgg | ttcctgaccc | tccta | 1855 |

<210> SEQ ID NO 20
<211> LENGTH: 19
<212> TYPE: PRT
<213> ORGANISM: Mus musculus

<400> SEQUENCE: 20

Glu Gln Ala Gln Lys Ala Lys Asn Pro Gln Glu Gln Lys Ser Phe Phe
1               5                   10                  15

Ala Lys Tyr

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 21

Cys Glu Gln Ala Gln Lys Ala Lys Asn Pro Gln Glu Gln Lys Ser Phe
1               5                   10                  15

Phe Ala Lys Tyr
            20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ctgctgtcaa tggcctctac                                            20

<210> SEQ ID NO 23
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtccgaaagg tgcgactc                                              18

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
catggccgcc agcttctga                                             19

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
ggagtttgcc aagctcggta aa                                         22

<210> SEQ ID NO 26
<211> LENGTH: 14

```
-continued

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
attgtcacgc taaa                                                         14
```

INHIBITOR OF NEURONAL CONNECTIVITY LINKED TO SCHIZOPHRENIA SUSCEPTIBILITY AND COGNITIVE DYSFUNCTION

CROSS REFERENCE TO RELATED APPLICATIONS

This application is a continuation of International Application No. PCT/US2012/045093 filed Jun. 29, 2012, which claims priority to U.S. Provisional Application Ser. No. 61/502,661, filed Jun. 29, 2011, priority to both of which is claimed, and the contents of each of which is incorporated by reference in its entirety herein.

GRANT INFORMATION

This invention was made with government support under grants MH067068 and MH077235 awarded by the National Institutes of Health. The Government has certain rights in the invention.

1. INTRODUCTION

The present invention relates to methods and compositions for enhancing neuronal connectivity.

SEQUENCE LISTING

The specification further incorporates by reference the Sequence Listing submitted herewith via EFS on Dec. 20, 2013. Pursuant to 37 C.F.R. §1.52(e)(5), the Sequence Listing text file, identified as 0700505112Seqlist.txt, is 19,313 bytes and was created on Dec. 19, 2013. The Sequence Listing, electronically filed herewith, does not extend beyond the scope of the specification and thus does not contain new matter.

2. BACKGROUND OF THE INVENTION

Association between recurrent de novo 22q11.2 microdeletions and schizophrenia represented a shift in our understanding of the genetic architecture of schizophrenia (SCZ), highlighting the role that rare and highly penetrant mutations play in the disease risk (1,2). This view has been strengthened recently by the identification of a widespread role of chromosomal microdeletions and microduplications (copy-number variants or CNVs) in determining susceptibility to schizophrenia and other psychiatric disorders (3-5). Individuals with 22q11.2 microdeletions have specific behavioral impairments and exhibit a spectrum of deficits in cognitive abilities linked to activity in the hippocampus and prefrontal cortex, such as measures of attention, working memory and executive function. Up to one third of children with the microdeletion develop schizophrenia or schizoaffective disorder in adolescence or early adulthood accounting for 1-2% of sporadic schizophrenia cases (2). Understanding how the genes disrupted by this microdeletion contribute to the emergence of the psychiatric and cognitive phenotypes associated with this genomic imbalance would provide important clues for the pathogenesis of SCZ and can guide future analysis of other CNVs that cause psychiatric disorders (6,7).

3. SUMMARY OF THE INVENTION

The present invention relates to methods and compositions for enhancing neuronal connectivity. It is based, at least in part, on the discovery of a protein, termed "Mirta22," that inhibits the formation of structures which create connections between neurons. It is further based, in part, on the discovery that inhibiting Mirta22 activity by short hairpin RNA was able to restore these structures. Mirta22 was discovered in experiments relating to 22q11 microdeletions, which have been linked to schizophrenia. Accordingly, the present invention provides for methods of treating schizophrenia comprising administering an agent that inhibits Mirta22 activity. It may also be used in the treatment of other disorders that would benefit from enhanced neural connectivity, including learning and memory disorders.

4. BRIEF DESCRIPTION OF THE FIGURES

FIG. 1A-D. Generation of Df(16)A$^{+/-}$ mice. (A) Schematic showing the human chromosome 22q11.2 region and the syntenic mouse region. Asterisks note Dgcr2 and Hira, the two endpoints of the targeted deletion. (B) Wild-type chromosomal loci for Dgcr2 and Hira, and their corresponding targeted loci after the introduction of a 5'HPRT and a 3'HPRT mini-cassette, respectively. (C) Cre-induced recombination between loxP sites in cis leads to a functional HPRT minigene and a 1.3 Mb deletion in the mice. After the loxP sites recombine to produce the deletion, an 829-bp PCR product can be detected. (D) FISH analysis of Het deletion mice. Metaphase preps from splenocyte cultures demonstrate a Het deletion FIG. 2A-E. Production, validation and analysis of miRNA biogenesis in Dgcr8-deficient mice. (A) Diagram showing the genomic structure of the Dgcr8 gene and the gene trap insert located in the intron between exons 8 and 9 (diagram not drawn to scale). En2 intron 1:1.5 kb of mouse En2 Intron 1:SA: splice acceptor of mouse En2 exon 2:β-geo: fusion of β-galactosidase and neomycin transferase; pA: SV40 polyadenylation signal. Arrowheads indicate the approximate genomic location of the PCR primers used for genotyping. (B) PCR genotyping designed to verify the gene trap insertion in HET Dgcr8$^{+/-}$ mice. (C) Northern blot analysis indicating the reduction in levels of the WT 4.5-kb Dgcr8 mRNA and the production of the expected 7.2-kb chimeric mRNA in Dgcr8$^{+/-}$ mice (arrowhead). (D) qRT-PCR analysis confirming reduction in the levels of WT Dgcr8$^-$ mRNA. (E) Western blot analysis indicating a reduction of the 120-kd WT Dgcr8 protein and the production of the expected ~220 kD chimeric protein (arrow).

FIG. 3A-J. Drastic reduction in mir-185 levels affects neuronal connectivity. (A) Expression of mir-185 mRNA in HPC and cortex as shown by in situ hybridization in coronal brain sections using an antisense mir-185 probe. An antisense U6 probe and a scramble probe were used as positive and negative controls, respectively. Images were taken at either ×4 (left panels) or ×10 (right panels) magnification. (B-D) mir-185 expression levels in HPC (B) or PFC (C) of Df(16)A$^{+/-}$ (n=7 for mutant, n=9 for WT littermates) and in HPC (D) of Dgcr8$^{+/-}$ (n=10 for mutant and WT littermates), as assayed by qRT-PCR. Expression levels in mutant animals were normalized to their respective WT littermates. (E) Representative Df(16)A$^{+/-}$ neurons at DIV9 transfected with pre-scramble or pre-mir-185 mimic and enhanced GFP for visualization. Scale Bar, 20 μm. (F,G) Reduction in the number of primary dendrites (F) and branch points (G) in Df(16)A$^{+/-}$ neurons at DIV9 relative to WT neurons is reversed by the transfection of pre-mir-185, but not pre-scramble mimic (pre-scr) (n=21 for WT=pre-scr; n=21 for Df(16)A$^{+/-}$+pre-scr; n=21 for Df(16)A$^{+/-}$+pre-mir-185). Values of Df(16)A$^{+/-}$ neurons were normalized to WT+pre-scr. (H) Representative images of spines on Df(16)A$^{+/-}$ neurons at DIV19, transfected with pre-scramble or pre-mir-185 mimic as well as enhanced GFP. Scale Bar, 5 μm. (I) Reduction in the density of mushroom spines (estimated over 75 μm of dendritic length) in DIV19 Df(16)A$^{+/-}$ neurons relative to WT control neurons is reversed by the transfection of pre-mir-185, but not pre-scramble mimic, into Df(16)A$^{+/-}$ neurons, (n=23 for WT+pre-scr; n=21 for Df(16)A$^{+/-}$+pre-scr; n=23 for Df(16)A$^{+/-}$+pre-mir-185). Values of Df(16)A$^{+/-}$ neurons were normalized to WT+pre-scr. (J) Transfection of pre-mir-185 mimic, but not pre-scramble control, significantly increased the width of mushroom spines of Df(16)A$^{+/-}$ neurons at DIV19 (P<0.001, Kolmogorov-Smirnov test) (n=568 for WT=pre-scr; n=339 for Df(16)A$^{+/-}$+pre-scr; n=527 for Df(16)A$^{+/-}$+pre-mir-185). For all data, *P<0.001, P<0.01, *P<0.05 (Student's t-test); Error bars indicate s.e.m.

FIG. 4A-E. 2310044H10Rik (Mirta22) is robustly unregulated in the brain of Df(16)A$^{+/-}$ mice. (A) Changes in gene expression in the PFC (upper panel) or HPC (lower panel) of Df(16)A$^{+/-}$ and WT littermate control mice at E16, P6 and adulthood (n=10 each group): Volcano plot of the P-values and the corresponding relative expression of each gene. (B) Top 10 protein encoding genes that show significant upregulation in the PFC (upper panel) or HPC (lower panel) of Df(16)A$^{+/-}$ and WT littermate mice at E16, P6 and adulthood. (C,D) Temporal expression of 2310044H10Rik (Mirta22) in the PFC (c) and HPC (d) of Df(16)A$^{+/-}$ and WT littermate mice as monitored by qRT-PCR. n=9-10 for each group. (E) Increased expression of endogenous 2310044H10Rik (Mirta22) in DIV9 hippocampal neurons isolated from Df(16)A+/− animals as assayed by qRT-PCR (n=3 each genotype). Expression levels in mutant neurons were normalized to WT neurons. *P<0.001, P<0.01, *P<0.05 (Student's t-test); Error bars indicate s.e.m.

FIG. 5A-H. miR-185 directly targets and represses 2310044H10Rik (Mirta22). (A) Structure of the 3'UTR of 2310044H10Rik (Mirta22) showing miRNA binding sites predicted by TargetScan or mirDB. Blocks in mouse 2310044H10Rik (Mirta22) 3'UTR that are highly conserved in rat and human orthologues are shown below the mouse 3'UTR. Evolutionary conservation is also assessed by the "30-way multiz alignment and conservation analysis" in the USCS browser.
(B-C) qRT-PCR quantification of endogenous 2310044H10Rik (Mirta22) in DIV7 hippocampal neurons. Expression levels in anti-mir-185-treated and pre-mir-185-treated neurons were normalized to expression levels under respective controls. (B) Increased expression levels of Mirta22 in neurons transfected with anti-miR-185 at DIV5 (n=5, each treatment), (C) Reduced expression levels of Mirta22 in DIV9 hippocampal neurons transfected with pre-miR-185 mimic at DIV7 (n=3, each treatment). (D-E) qRT-PCR quantification of endogenous 2310044H10Rik (Mirta22) in N18 cells. Expression levels in pre-mir-185-treated and anti-mir-185-treated cells were normalized to expression levels under respective controls. (D) Reduced expression levels of Mirta22 in cells transfected with pre-mir-185 mimic (n=3, each treatment). (E) Up-regulation of Mirta22 in cells transfected with an anti-mir-185 LNA oligo (n=3, each treatment). (F-H) Repression effects of pre-mir-185, pre-mir-485 and pre-mir-491 on Mirta22 3'UTR were examined by a dual-luciferase reporter assay. psiCHECK2 plasmids containing a *Renilla luciferase* gene under the control of either Wt or one of the mutant 2310044H10Rik (Mirta22) 3'UTRs were co-transfected with pre-miRNA or pre-scramble mimic into the N18 neuroblastoma cell line (n=3 for each condition). Firefly luciferase expressed from the same plasmid was used as internal control. Values are *Renilla luciferase* levels relative to firefly luciferase levels and normalized to the relative expression levels under pre-scramble treatment (F, H) or to the relative expression levels from plasmid with no 3'UTR (G). Pre-mir-185 significantly decreases the 2310044H10Rik (Mirta22) 3'UTR reporter expression over a concentration range of 10 nM to 0.01 nM (F). pre-mir-185 mediated repression on 2310044H10Rik (Mirta22) 3'UTR reporter expression depends on conserved miRNA binding sites (G). 2310044H10Rik (Mirta22) 3'UTR luciferase reporters with mutations at Site 1 (Mut1) or Site 2 (Mut2) or both sites (Mut1& 2) were analyzed. Mutated 2310044H10Rik (Mirta22) 3'UTR reporters express significantly higher luciferase activities than Wt Mirta22 3'UTR reporters. Pre-mir-485 and pre-mir-491 significantly decreases the 2310044H10Rik (Mirta22) 3'UTR reporter expression (H). For all data, *P<0.001, P<0.01, *P<0.05 (Student's t-test); Error bars indicate s.e.m.

FIG. 6A-D. Genomic structure, neuronal expression and subcellular localization of 2310044H10Rik (Mirta22). (A) Top: Structure of mRNA transcripts of 2310044H10Rik (Mirta22) and its human orthologue, C19orf63. RefSeq reports a 2310044H10Rik (Mirta22) transcript with 7 exons, which is predicted to encode a signal peptide and a transmembrane domain. For C19orf63, RefSeq reports 2 alternatively spliced transcripts: one that encodes a predicted transmembrane protein and one with an additional exon that encodes a predicted secreted protein. Bottom: Protein sequence alignment of predicted transmembrane isoforms encoded by 2310044H10Rik (Mirta22) and its human orthologue. Black blocks indicate completely conserved residues; grey blocks indicate similar residues (defined by Boxshade default similarities); white blocks indicate different residues. (B) Upper: Representative western blot assays of 2310044H10Rik (Mirta22) in PFC lysates prepared from Df(16)A$^{+/-}$ animals and Wt littermates. Alpha-tubulin is used as loading control. Lower: Quantification of 2310044H10Rik (Mirta22) protein level in PFC of Wt and Df(16)A$^{+/-}$ animals (n=9 each genotype). Expression levels in mutant mice were normalized to Wt littermates. Results are expressed as mean±SEM. **p<0.01 (Student's t-test). (C) Quantification 2310044H10Rik (Mirta22) immunocytochemical signals in Wt and Df(16)A$^{+/-}$ cultured neurons (n=34 for Wt; n=31 for Df(16)A$^{+/-}$). Expression levels in mutant neurons were normalized to Wt neurons. Results are expressed as mean±SEM. *p<0.05 (Student's t-test). (D) Upper panel: 2310044H10Rik (Mirta22) co-localizes with neuron specific marker NeuN, but not with glia specific marker GFAP, in cultured hippocampal neurons at DIV20. Lower panel: 2310044H10Rik (Mirta22) co-localizes with Golgi specific marker GM130 in the soma. 2310044H10Rik (Mirta22) is also found in vesicles and tubular-like clusters in the dendrites, which are highlighted by the dendritic marker MAP2.

FIG. 7A-L. Elevated 2310044H10Rik (Mirta22) Levels Contribute to Structural Alterations of Df(16)A$^{+/-}$ Neurons. (A) qRT-PCR results showing that the Mirta22 mRNA was significantly increased in DIV12 hippocampal cultured neurons transfected with a full length Mirta22 cDNA plasmid. (B) Right: Representative western blot showing the reduction of the endogenous Mirta22 protein in DIV12 hippocampal neurons transfected with Mirta22 cDNA (lane 2) or empty vector (lane 1). Alpha-tubulin is the loading control. Left: Quantification of western blots showing a 58% increase (p<10$^{-4}$; n=4 each condition) in Mirta22 signal in Mirta22 cDNA-transfected cells, compared to empty vector-transfected cells. (C-D) Transfection of a 2310044H10Rik (Mirta22) expression construct into Wt neurons at DIV7 results in decrease in the number of primary dendrites (C) and branch points (D) at DIV9 (n=24 for empty vector transfected and n=27 for Mirta22 transfected cells). In (D), values of Mirta22 overexpressing neurons were normalized to empty vector-transfected neurons. (E-F) Introduction of 2310044H10Rik (Mirta22) into Wt neurons at DIV17 results in decrease in the density of mushroom spines (E) and the width of those spines (F) ($P<0.01$, Kolmogorov-Smirnov test) at DIV19 [n=16 for vector transfected and n=17 for Mirta22 transfected neurons (E); n=278 for spines on vector transfected neurons and n=231 for spines on Mirta22 transfected neurons (F)]. Values of Mirta22 overexpressing neurons were normalized to empty vector-transfected neurons. (G) qRT-PCR results showing that the endogenous Mirta22 mRNA was significantly reduced in DIV12 hippocampal cultured neurons transfected with Mirta22 shRNA. (H) Right: Representative western blot showing the reduction of the endogenous Mirta22 protein in DIV12 hippocampal neurons transfected with Mirta22 shRNA (lane 2) or scramble shRNA (lane 1). Alpha-tubulin is the loading control. Left: Quantification of western blots showing a 48% decrease (p<0.01; n=4 each condition) in Mirta22 levels in Mirta22 shRNA-transfected cells, compared to scramble shRNA-transfected cells. (I-J) Reduction in the number of primary dendrites (I), but not reduction in the number branch points (J), in Df(16)A$^{+/-}$ neurons at DIV9 relative to Wt neurons is reversed by the transfection of a construct that expresses 2310044H10Rik (Mirta22) shRNA$^{+/-}$ (n=24 for Wt+scr shRNA; n=21 for Df(16)A$^{+/-}$ scr shRNA; n=25 for Df(16)A$^{+/-}$+Mirta22 shRNA). Scr shRNA: scramble shRNA. N.S.: not significant. In (J), values of Df(16)A$^{+/-}$ neurons were normalized to Wt+scr shRNA. (K) Reduction in the density of mushroom spines (estimated over 75 μm of dendritic length) in Df(16)A$^{+/-}$ neurons at DIV19 relative to Wt neurons is reversed by the introduction of Mirta22 shRNA, but not scramble shRNA$^{+/-}$ (n=22 for Wt+scr shRNA; n=24 for Df(16)A$^{+/-}$ scr shRNA; n=15 for Df(16) A$^{+/-}$+Mirta22 shRNA). Values of Df(16)A$^{+/-}$ neurons were normalized to Wt+scr shRNA. (L) Transfection of Mirta22 shRNA does not affect the width of mushroom spines of Df(16)A$^{+/-}$ neurons at DIV19 (p 0.05, Kolmogorov-Smirnov test), n=342 for Wt+pre-scr; n=289 for Df(16) A$^{+/-}$+pre-scr, n=177 for Df(16)A$^{+/-}$+pre-miR-185. (A-E, G-K) Results are expressed as mean±SEM. *p<0.05, **p<0.01 (Student's t-test).

Figure 8A:
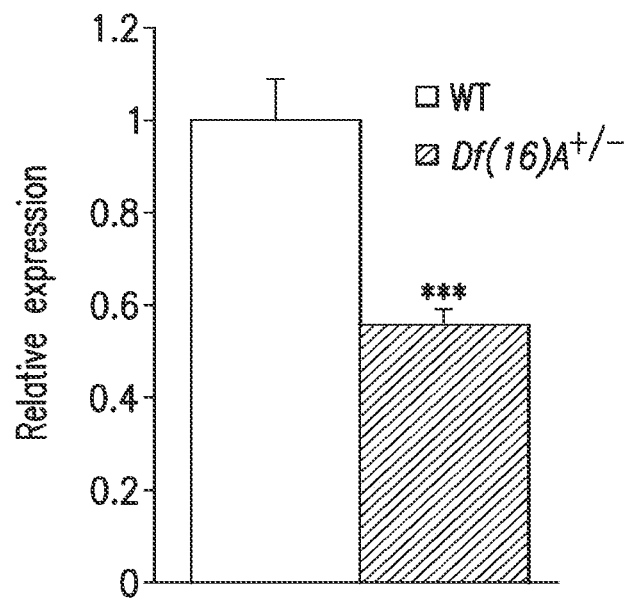
Figure 8B:
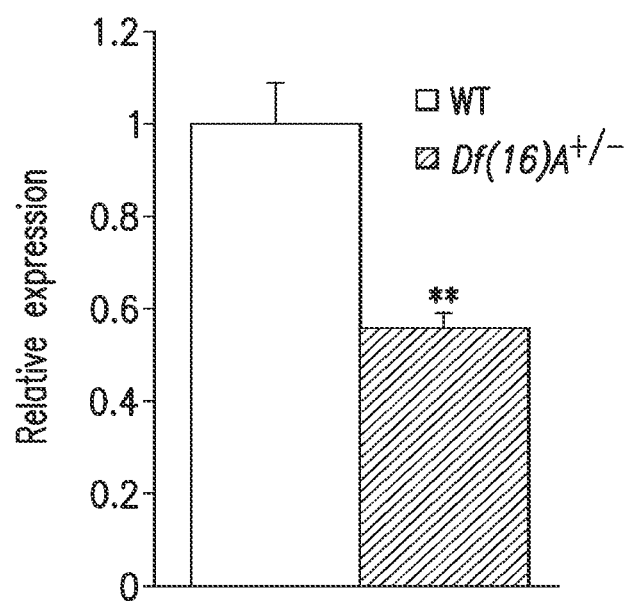

FIG. 8A-B. Dgcr8 levels in Df(16)A$^{+/-}$ mice during brain development. (A,B) Dgcr8 expression levels in HPC of E17 (a) and P6 (b) Df(16)A$^{+/-}$ mice (n=10) and their respective WT littermate controls (n=10), as assayed by qRT-PCR. Expression levels in mutant animals were normalized to their respective WT littermates. *P<0.001, P<0.01 (Student's t-test); Error bars indicate s.e.m.

Figure 9A:
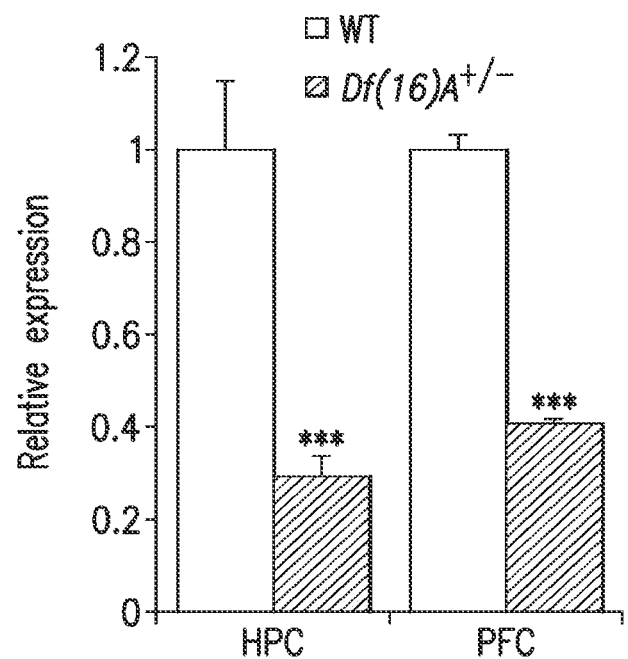
Figure 9B:
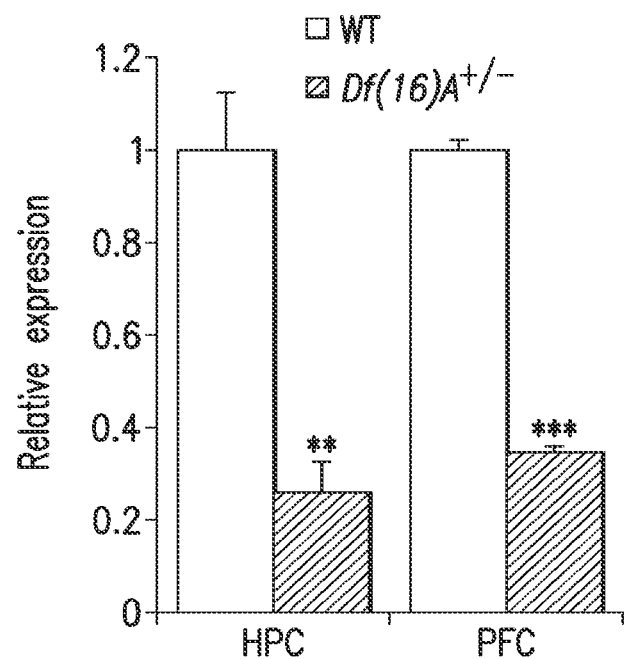

FIG. 9A-B. mir-185 levels in Df(16)A$^{+/-}$ mice during brain development. (A,B) mir-185 expression levels in HPC and PFC of E17 (a) and P6 (b) Df(16)A$^{+/-}$ mice (n=10 for HPC or PFC) and their respective WT littermate control mice (n=10 for HPC or PFC), as assayed by qRT-PCR. Expression levels in mutant animals were normalized to their respective WT littermates. *P<0.001, P<0.01 (Student's t-test); Error bars indicate s.e.m.

Figure 10:
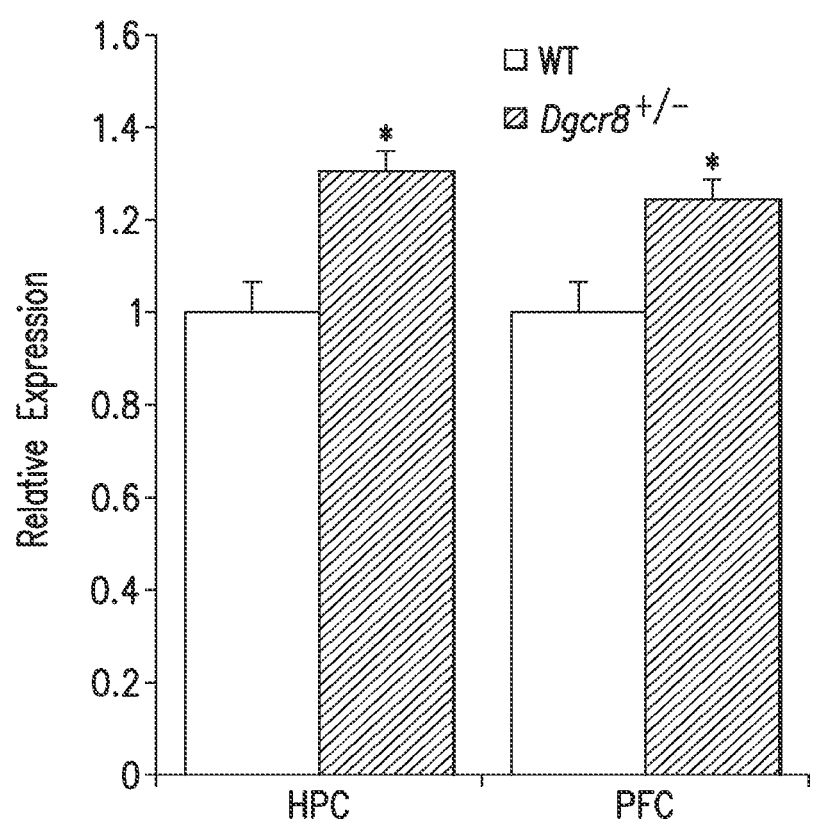

FIG. 10. 2310044H10Rik (Mirta22) expression in the brain of Dgcr8$^{+/-}$ mice. Expression levels in HPC and PFC of adult Dgcr8$^{+/-}$ mice (n=7 for HPC; n=10 for PFC) and their respective WT littermate controls (n=8 for HPC; n=10 for PFC), as assayed by qRT-PCR. Expression levels in mutant animals were normalized to their respective WT littermates. *P<0.05 (Student's t-test); Error bars indicate s.e.m.

Figure 11A:
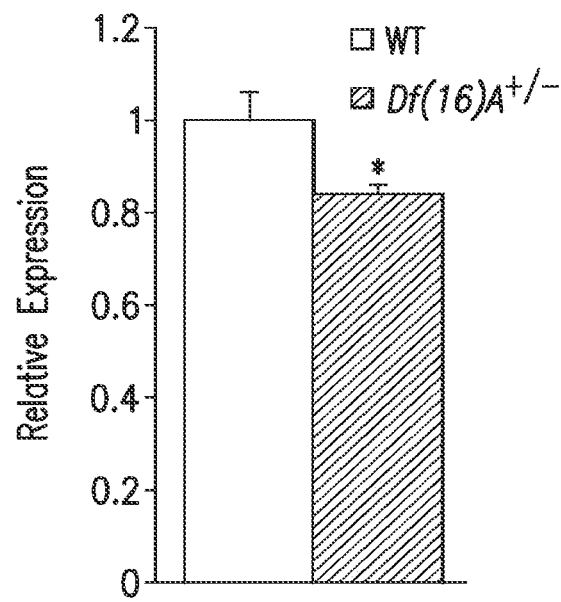
Figure 11B:
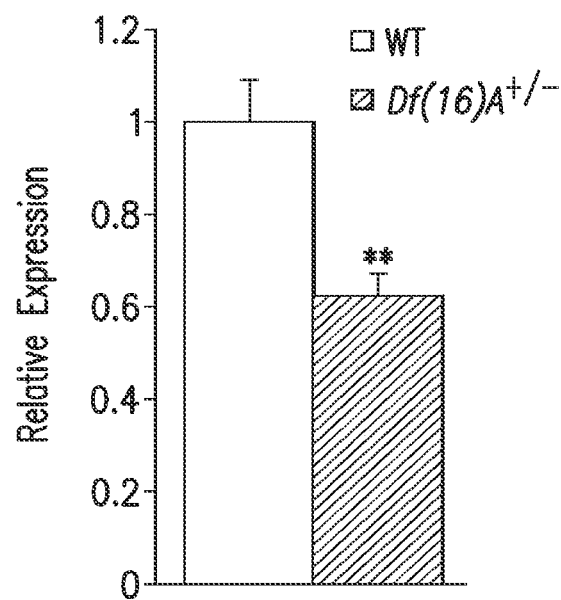

FIG. 11A-B. mir-485 and mir-491 levels are reduced in Df(16)A$^{+/-}$ mice. (A,B) Expression levels of mir-485 (a) and mir-491 (b) in HPC of adult Df(16)A$^{+/-}$ mice (n=7) and their respective WT littermate control mice (n=9), as assayed by qRT-PCR. Expression levels in mutant animals were normalized to their respective WT littermates. **P<0.01, *P<0.05 (Student's t-test); Error bars indicate s.e.m.

Figure 12:
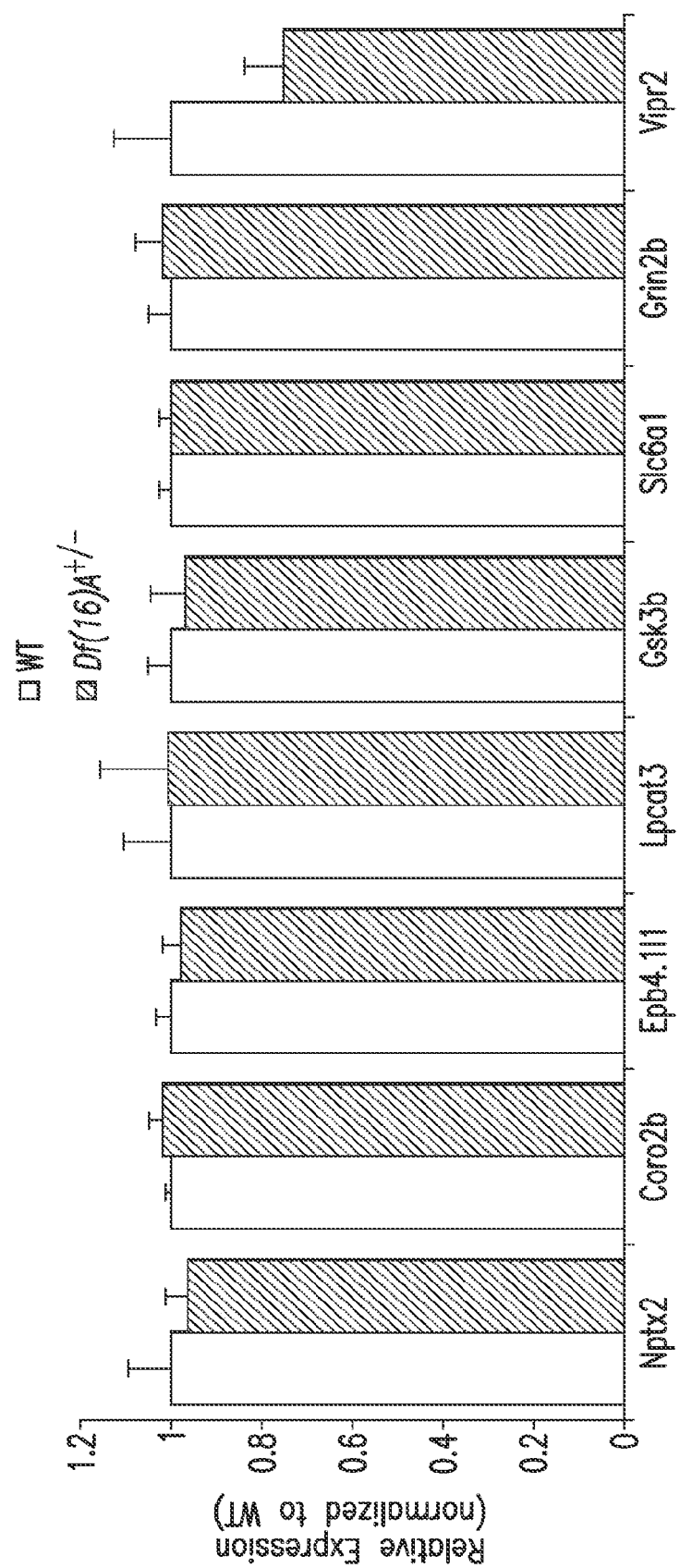

FIG. 12. Expression levels of a sample of putative miR-185 targets predicted by both TargetScan and miRanda (Nptx2, Coro2b, Epb4.1l1, Lpcat3, Gsk3b, Slc6a1, Grin2b and Vipr2) in the HPC of adult Df(16)A$^{+/-}$ mice (n=10) and their respective Wt littermate mice (n=10), as assayed by qRT-PCR. Expression levels in mutant animals were normalized to their respective Wt littermates. For all genes tested, expression levels were not significantly altered in mutant animals. Expression levels in mutant animals were normalized to their respective Wt littermates. Results are expressed as mean±SEM. *p<0.05, p<0.01, *p<0.001 (Student's t-test).

FIG. 13A-G. Specificity of 23100441H10Rik (Mirta22) Antibody. (A) Anti-2310044H10Rik (anti-Mirta22) antibody, as well as polyclonal and monoclonal anti-FLAG antibodies, recognize a 28 kD band in western blots on lysates of 293T cells transfected with a plasmid expressing full length 2310044H10Rik (Mirta22) cDNA with a C-terminal FLAG tag ("Flag tagged" lanes). Lysates of cells transfected with empty vector were used as control ("control" lanes). Note that there is a 28 kD band recognized by anti-2310044H10Rik antibody, but not by anti-FLAG antibodies, in control lysates. This likely represents the endogenous human 2310044H10Rik (Mirta22) orthologous protein (C19orf63). (3) Upper panel: Representative western blot showing the reduction of the endogenous 2310044H10Rik (Mirta22) protein in N18 cells transfected with 2310044H10Rik (Mirta22) shRNA (lane 2) compared to scramble shRNA-transfected cells (lane 1). Alpha-tubulin is the loading control. Lower panel: Quantification of western blots showing a 32% reduction (p<0.01; n=6 each condition) in 2310044H10Rik (Mirta22) signal in 2310044H10Rik (Mirta22) shRNA-transfected cells, compared to scramble shRNA-transfected cells. Expression levels in 2310044H10Rik (Mirta22) shRNA-manipulated neurons were normalized to their respective controls. (C) Upper panel: Representative western blot showing the expected increase in 2310044H10Rik (Mirta22) protein levels in N18 cells transfected with 2310044H10Rik (Mirta22) cDNA (lane 2) compared to empty vector-transfected cells (lane 1). Alpha-tubulin is the loading control. Lower panel: Quantification of western blots showing a 57% increase (p<0.05; n=6 each condition) in 2310044H10Rik (Mirta22) signal in 2310044H10Rik (Mirta22) cDNA-transfected cells, compared to empty vector-transfected cells. Expression levels in 2310044H10Rik (Mirta22) cDNA-manipulated neurons were normalized to their respective controls. (D) Anti-23100441l0Rik (anti-Mirta22) antiserum, but not pre-immune serum, recognizes endogenous Mirta22 protein in DIV20 Wt hippocampal neurons, as assayed by immunocytochemistry. (E) Representative immunocytochemistry images showing that 2310044H10Rik (Mirta22) signal as compared to Golgi marker GM130, is largely reduced in 2310044H10Rik (Mirta22) shRNA-transfected (RFP+) DIV14 Wt hippocampal neurons (lower panel) but not in scramble shRNA-transfected (RFP+) neurons (upper panel).

Note that in 2310044H10Rik (Mirta22) shRNA-treated culture (lower panel), 2310044H10Rik (Mirta22) signal in un-transfected neurons (marked by white arrows) is not reduced, as compared to scramble shRNA-transfected (RFP+) neurons (shown in upper panel). Transfection was performed at DIV12 and neurons were fixed and immunostained 2 days later. (F) Quantification of Mirta22 immunocytochemical signal shown in (E). Note that in 2310044H10Rik (Mirta22) shRNA-treated neuronal cultures, there is a 64% decrease (p<0.001) in 2310044H10Rik (Mirta22) signal in transfected neurons (RFP+, n=20), compared to un-transfected neurons in (RFP−, n=20). In scramble shRNA-treated cultures, there is no difference in 2310044H10Rik (Mirta22) signal between transfected (RFP+, n=10) and un-transfected (RFP−, n=10) neurons. Mirta22 signal measurements in transfected (RFP+) and un-transfected (RFP−) neurons in scramble shRNA treated culture and 2310044H10Rik (Mirta22) shRNA-transfected neurons (RFP+) were normalized to un-transfected neurons (RFP−) in 2310044H10Rik (Mirta22) shRNA treated culture. (G) Anti-Mirta22 antibody serum, but not pre-immune serum, recognizes endogenous Mirta22 protein in western blot assays of hippocampal protein extracts. Representative western blot images from two animals are shown in each case. Results are expressed as mean±SEM. *p<0.05, p<0.01, *p<0.001 (Student's t-test).

Figure 14A:
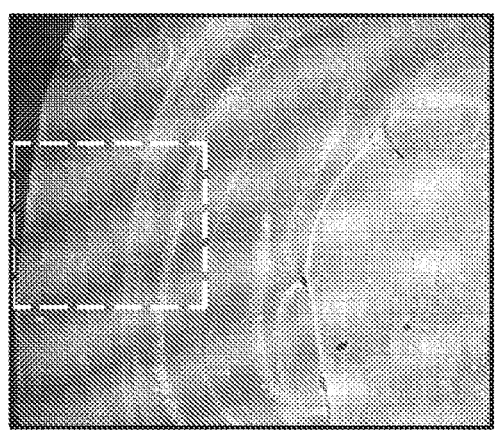
Figure 14B:
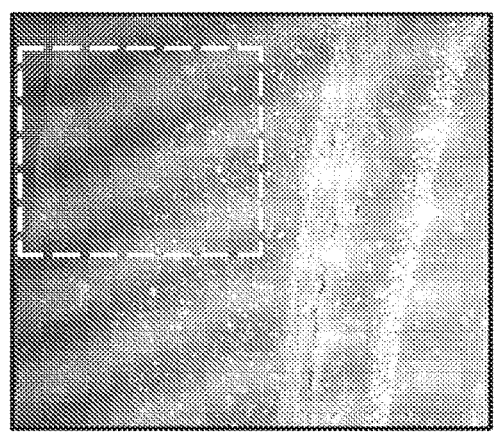
Figure 14C:
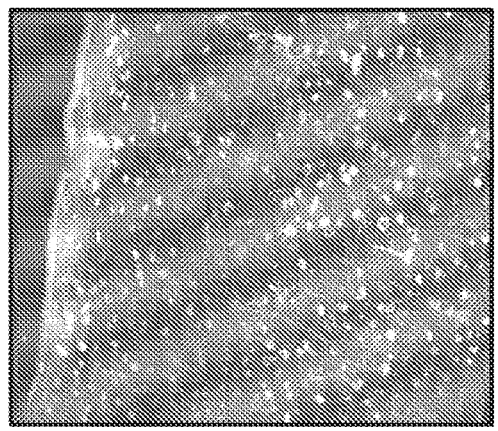

FIG. 14A-C. 2310044H10Rik (Mirta22) distribution in the adult brain. (A-C) Mirta22 distribution as assayed by immunohistochemistry on brain slices using anti-Mirta22 antibody. Images were taken at 4× (A), 10× (B) and 20× (C) magnification. Boxes in 4× and 10× images outline the area shown in 10× and 20× images, respectively. Note the widespread distribution of Mirta22 immunoreactivity in the brain, including in the cortex and hippocampus. Cortical neurons with processes can be seen clearly in the 20× image (C).

Figure 15A:
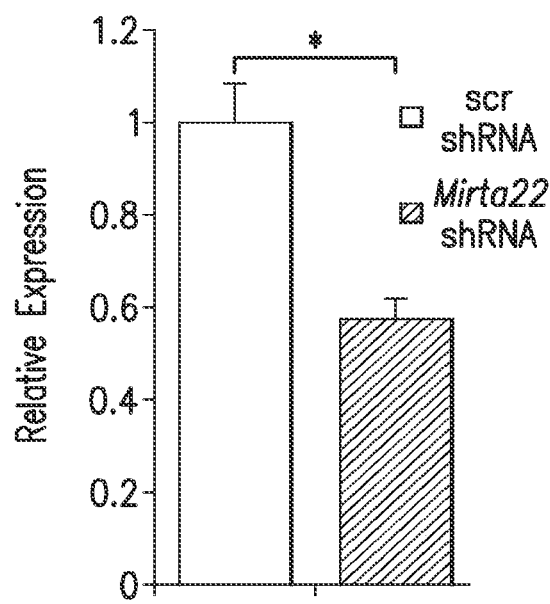
Figure 15B:
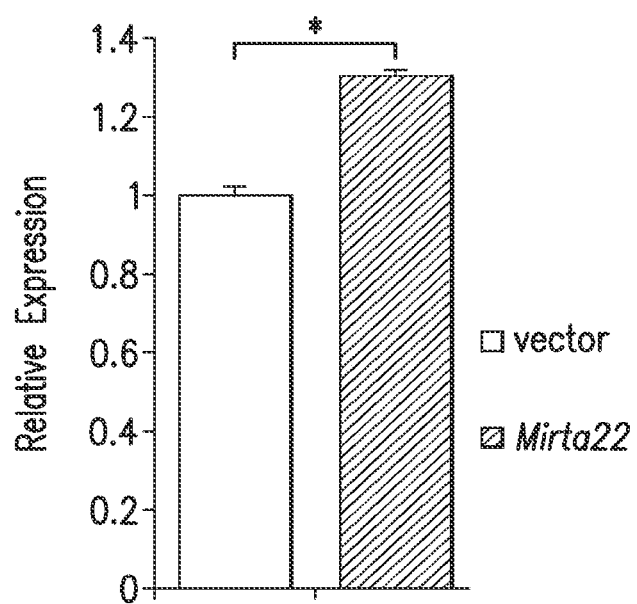

FIG. 15A-B. Bidirectional manipulation of 2310044H10Rik (Mirta22) levels. (A) Mirta22 expression levels in N18 cells, a mouse neuroblastoma cell line, transfected with plasmids expressing Mirta22 shRNA or scramble shRNA (n=3 for each treatment), as assayed by qRT-PCR. Expression levels in Mirta22 shRNA-treated cells were normalized to scramble shRNA-treated cells. (B) Mirta22 expression levels in N18 cells transfected with plasmids expressing Mirta22 cDNA or empty vector (n=3 for each treatment), as assayed by qRT-PCR. Expression levels in Mirta22 cDNA-treated cells were normalized to vector-treated cells. *P<0.05 (Student's t-test); Error bars indicate s.e.m.

FIG. 16A-C. Mirta-encoding cDNA. (A) Human Isoform 1, Genbank Accession No. NM_175063 (SEQ ID NO:3); (B) Human Isoform 2, Genbank Accession No. NM_175063 (SEQ ID NO:5); (C) Murine mirta-encoding cDNA, GenBank Accession No. NM_197991 (SEQ ID NO: 19).

FIG. 17A-F. (A) Representative images of Wt neurons at DIV9 transfected with anti-miR control or anti-miR-185 oligos and enhanced GFP to facilitate visualization of dendrites and spines. (B-C) Reduction in the number of primary dendrites (B) and branch points (C) in Wt neurons at DIV9, 2 days after transfected with anti-miR-185 relative to Wt neurons transfected with anti-miR control (n=21 for Wt+anti-miR-185; n=20 for Wt+anti-miR control). In (C), values of Wt+anti-miR-185 were normalized to Wt+anti-miR control. (D) Representative images of spines on Wt neurons at DIV19, transfected with anti-miR control or anti-miR-185 as well as enhanced GFP. (E) Reduction in the density of mushroom spines (quantified over 75 μm of dendritic length) in neurons transfected with anti-miR-185 relative to neurons transfected with anti-miR control (n=20 for Wt+anti-miR-185; n=20 for Wt+anti-miR control). Values of Wt+anti-miR-185 were normalized to Wt+anti-miR control. (F) Transfection of anti-miR-185 oligos significantly decreased the width of mushroom spines compared to that of the neurons transfected with anti-miR control at DIV19 (15%, P<0.001, Kolmogorov-Smirnov test) (n=232 for Wt+anti-miR-185; n=293 for Wt+anti-miR control). (B, C, E) Results are expressed as mean±SEM. *p<0.05, **p<0.01 (Student's t-test).

FIG. 18A-F. miR-185 Levels Affect Dendritic and Spine Development. (A) Sholl analysis of dendritic complexity using 10 μm concentric circles around the soma. Wt neurons transfected with either anti-miR-185 (n=21) or anti-miR control (n=20) at DIV7 and fixed at DIV9. Increase in branching is prevalent in the vicinity of the most proximal dendrites. (B) Distribution of spine morphotypes (other than mushroom spines, quantified over 75 μm of dendritic length from soma), as well as total protrusions, in cultured Wt hippocampal neurons transfected with anti-mir-185 relative to neurons transfected with anti-mir control (n=20 for Wt+anti-mir control; n=20 for Wt+anti-mir-185). (C) Increase in the number of primary dendrites and branch points in DIV9 (2 days following transfection) Wt neurons transfected with pre-mir-185 relative to Wt neurons transfected with pre-scramble mimic (pre-scr) (n=21 for Wt+pre-mir-185; n=20 for Wt+pre-scr). For the number of branch point, values of Wt+pre-mir-185 were normalized to Wt+pre-scr. (D) Left: Increase in the density of mushroom spines (quantified over 75 μm of dendritic length) in DIV19 Wt neurons transfected with pre-mir-185 relative to Wt neurons transfected with pre-scr (n=23 for Wt+pre-scr; n=23 for Wt+pre-mir-185). Values of Wt neurons with pre-mir-185 were normalized to Wt with pre-scr. Right: Transfection of pre-mir-185 mimic, but not pre-scramble control, significantly increased the width of mushroom spines on Wt neurons at DIV19 (18%, P<0.001, Kolmogorov-Smirnov test) (n=568 for Wt+pre-scr; n=527 for Wt+pre-mir-185). (E) Sholl analysis of dendritic complexity using 30 μm concentric circles around the soma. Df(16)A$^{+/-}$ neurons transfected with either pre-miR-185 mimic (n=21) or pre-scramble mimic (n=21) at DIV7 and fixed at DIV9. Reduction in branching in Df(16)A$^{+/-}$ neurons is reversed by pre-miR-185 mimic throughout the dendritic tree, although it is more pronounced in the vicinity of the most proximal dendrites. (F) Distribution of spine morphotypes (other than mushroom spines, quantified over 75 μm of dendritic length from soma), as well as total protrusions, in cultured DIV19 Df(16)A$^{+/-}$ hippocampal neurons transfected pre-mir-185 or pre-scramble mimic relative to Wt neurons transfected with pre-scramble mimic (n=23 for Wt+pre-scr; n=21 for Df(16)A$^{+/-}$+pre-scr; n=23 for Df(16)A$^{+/-}$+pre-mir-185).

Results are expressed as mean±SEM. *p<0.05, p<0.01, *p<0.001 (Student's t-test).

FIG. 19A-D. Generation of Df(16)B and Dp(16)B. (A) Dgcr14 and Hira loci and the corresponding targeted loci following the introduction of 5' HPRT and 3' HPRT minicassettes, respectively. (B) Upon exposure to Cre recombinase. recombination between the Lox P sites of modified loci positioned in the trans orientation, led to the generation of a deletion between Dgcr14 and Hira, as well as a duplication of the region. (C) Southern blot of 2 ES cell clones, using probes A and B (positions of probes, as well as expected sizes upon digestion with KpnI, indicated in panel B. E5 and E8 possess both the deletion (indicated by a 22.9 kb band) as well as the duplication (indicated by a 16.6 kb band). Wt indicates lane with DNA from wild type ES cells. M indicates the marker lane, BstEII cut λ DNA. (D) FISH verification. Top panel: metaphase chromosome spread of MEFs possessing the duplication. A slightly brighter signal (arrow) indicates the duplicated region. Middle panel: Interphase FISH of the duplication. The duplication is demonstrated by a third separate signal. Bottom panel: Metaphase chromosome spread of Mt-Ts possessing the deletion. MEF: mouse embryonic fibroblast. FISH: fluorescent in situ hybridization. RP23-420H6: mouse BAC probe located within the deleted and duplicated regions. RP23-290E4: mouse BAC probe located outside of the deleted and duplicated regions.

FIG. 20. List of transcripts outside the 22q11.2 syntenic region significantly misregulated in a reciprocal manner in both PFC and HPC.

FIG. 21. Three-factor ANOVA of the impact of mir-185, mir-485 and mir-491 on luciferase activity, related to FIG. 4.

Figure 22:
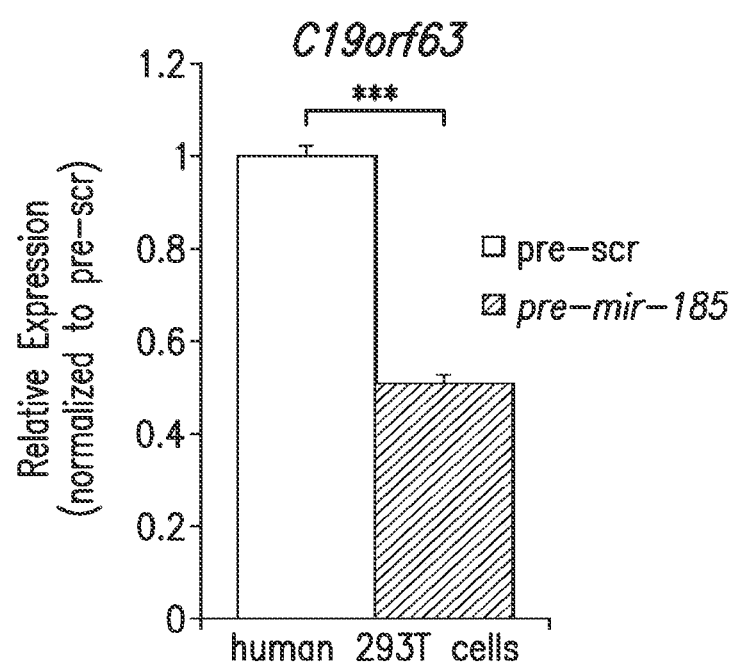

FIG. 22. 293T cells transfected with pre-miR-185 mimic or pre-scramble (pre-scr) oligo. Expression levels of C19orf63, the human homolog of 2310044H10Rik (Mirta22), were assayed by qRT-PCR. Expression levels of C19orf63 in cells transfected with pre-miR-185 (n=3) were normalized to the pre-scr controls (n=3).

Figure 23A:
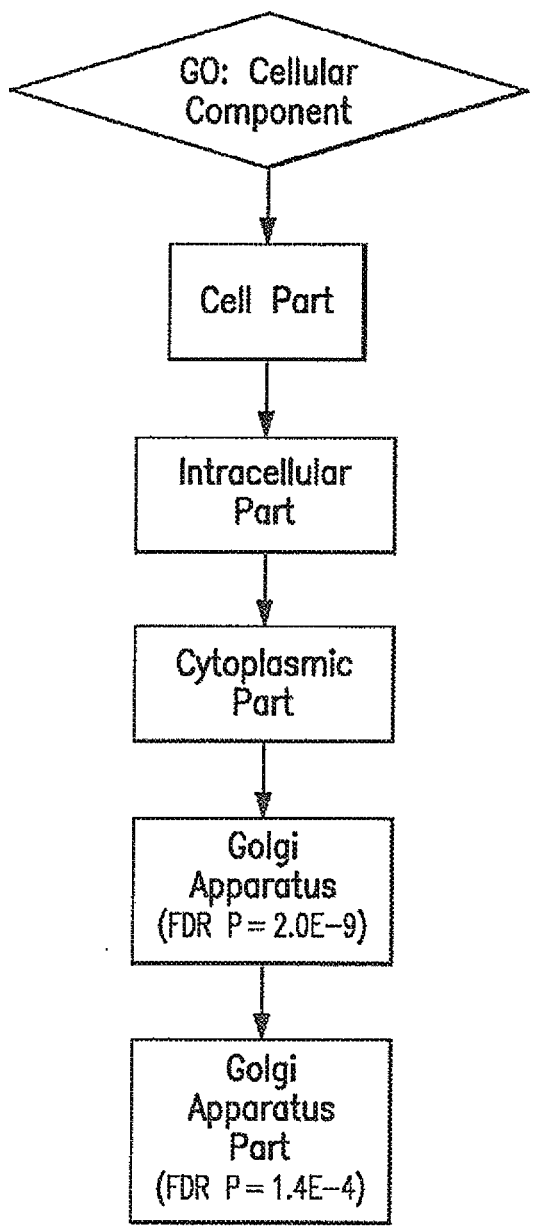
Figure 23A:
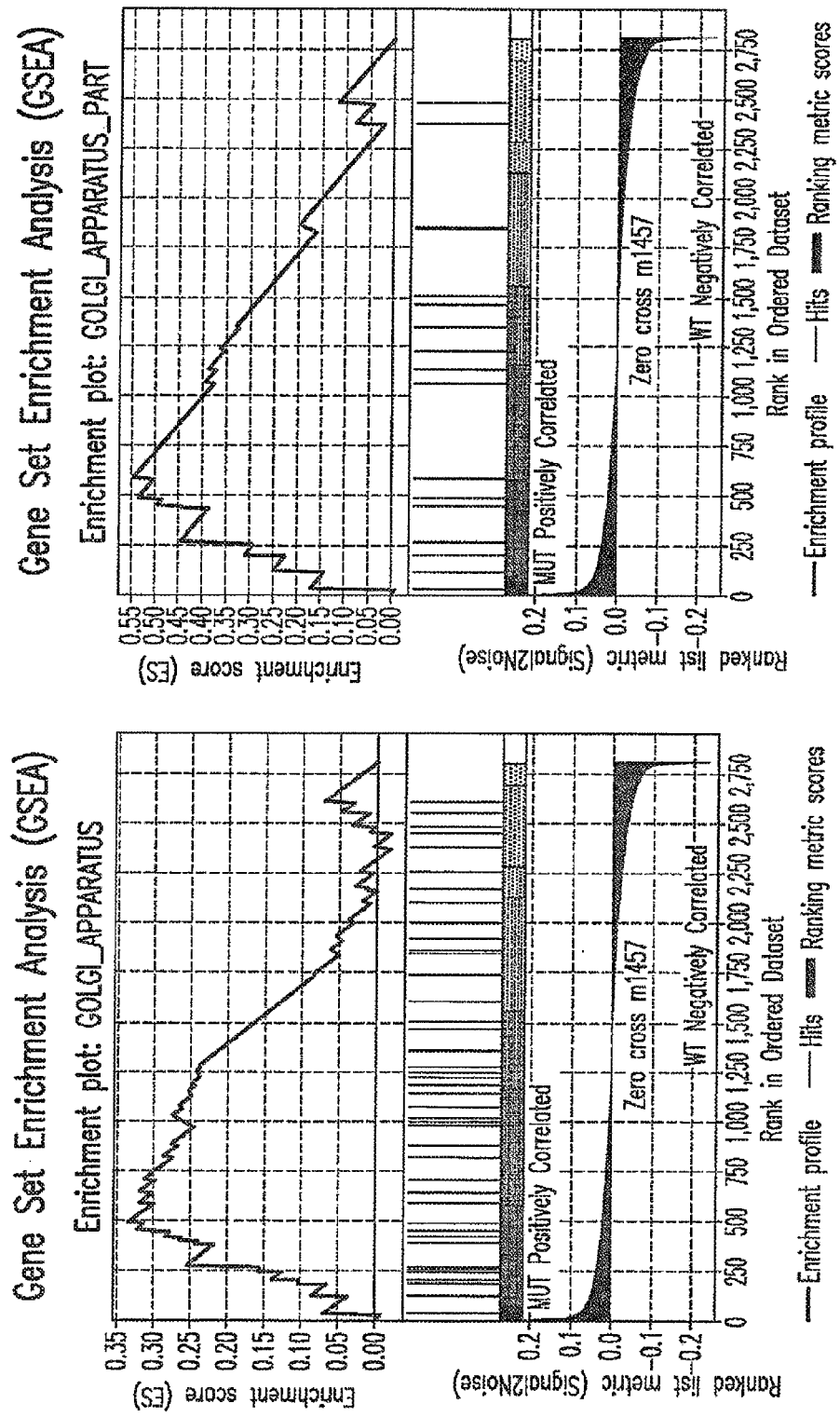
Figure 23B:
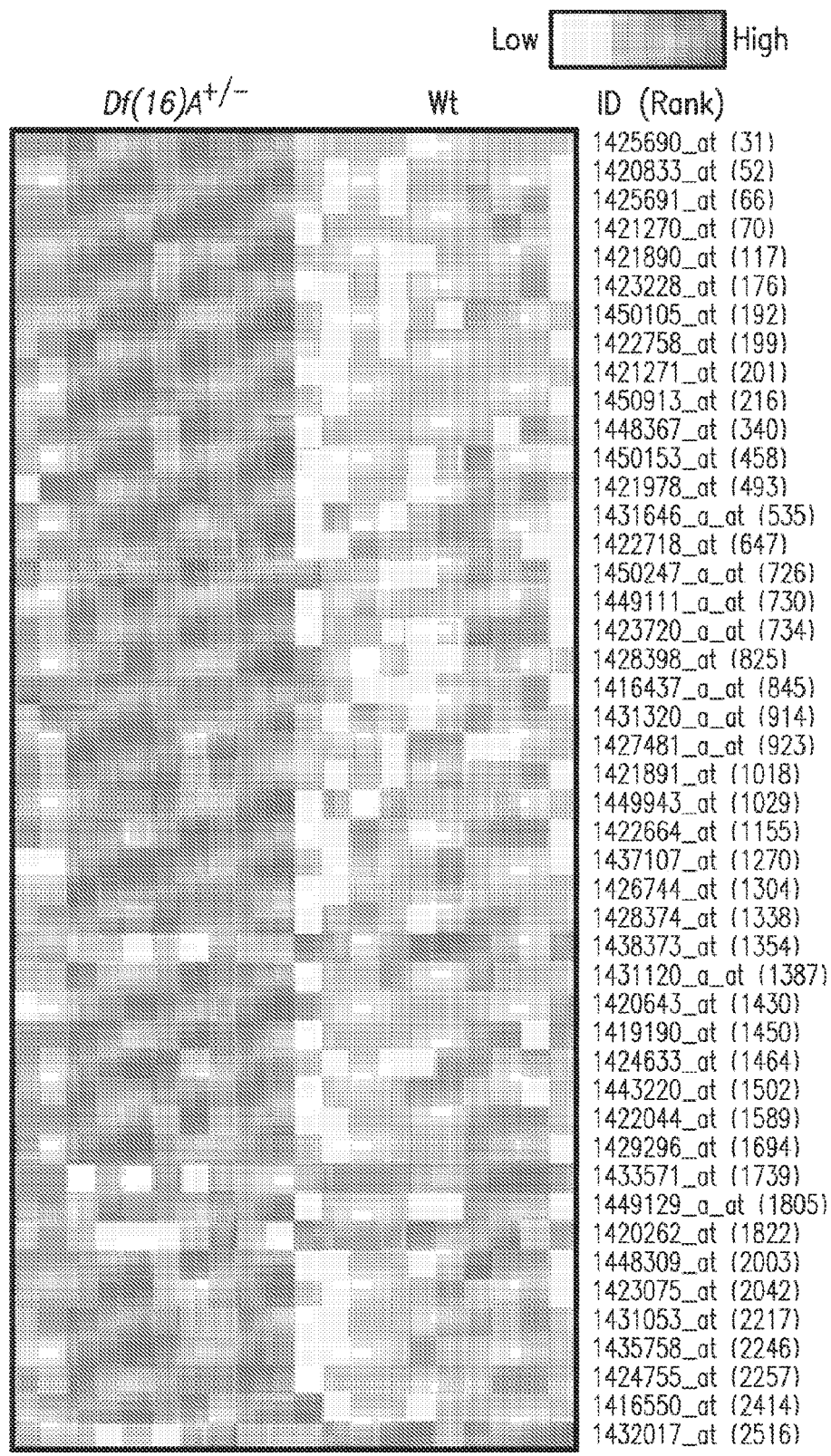

FIG. 23A-B. Coordinated Mild Dysregulation of Golgi-related Putative mir-185 Targets in Df(16)A$^{+/-}$ mice. (A) 2708 genes that were predicted to be miR-185 targets by TargetScan Mouse v5.2 were imported into the DAVID bioinformatics resources 6.7 (http://david.abcc.ncifcrf.gov) and 2695 genes have corresponding DAVID IDs. Functional annotation analysis using *Mus musculus* genes as background identified Gene Ontology (cellular component) term "Golgi apparatus" as the top enriched gene cluster (gene count=159, Enrichment Score=8.56, FDR-corrected P=2× $10^{-9}$) and term "Golgi apparatus part" as the second best hit with FDR-corrected P=4×$10^{-3}$ (left). The same gene list was also imported into Gene Set Enrichment Analysis (GSEA v2.0). The Gene Ontology (cellular component) terms "Golgi apparatus part" (NES=1.35, P=0.1) and "Golgi apparatus" (NES=1.3, P=0.1) were again among the top enriched gene sets (right). (B) Expression heatmap plot of the potential miR-185 targets that serve Golgi apparatus related functions (GO term) and are differentially expressed (p<0.005) between adult HPC of Df(16)A$^{+/-}$ mice and Wt littermates. ID is Affymetrix ID (see FIG. 28) and Rank is the ranking position in the list of all differentially expressed genes according to significance level. Note that the majority (91%, 42 out of 46) of the genes are upregulated.

Figure 24:
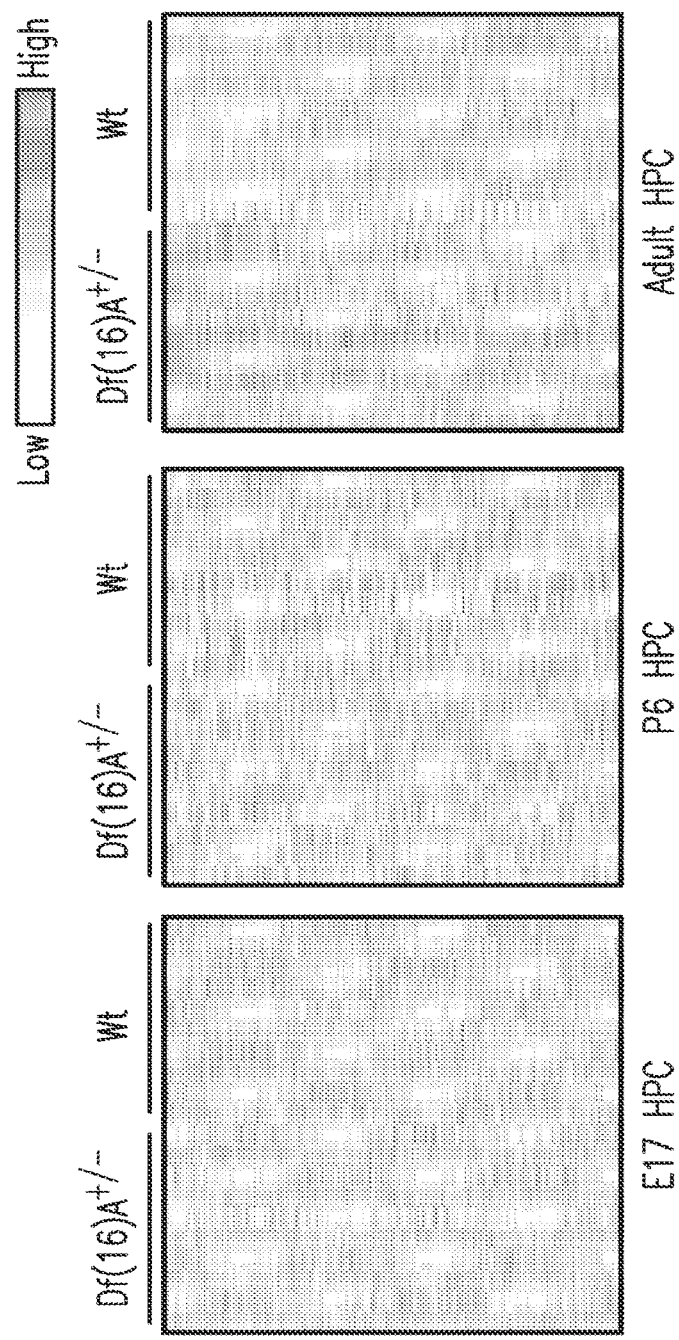

FIG. 24. miR-185 Reduction Results in Coordinated Mild and Age-specific Dysregulation of Golgi-related Genes, Related to FIG. 5
Expression heatmap plot of all potential miR-185 targets that have Golgi apparatus related function (GO term) in E17 (left panel), P6 (middle panel) and adult (right panel) HPC of Df(16)A$^{+/-}$ mice and Wt littermates.

Figure 25:
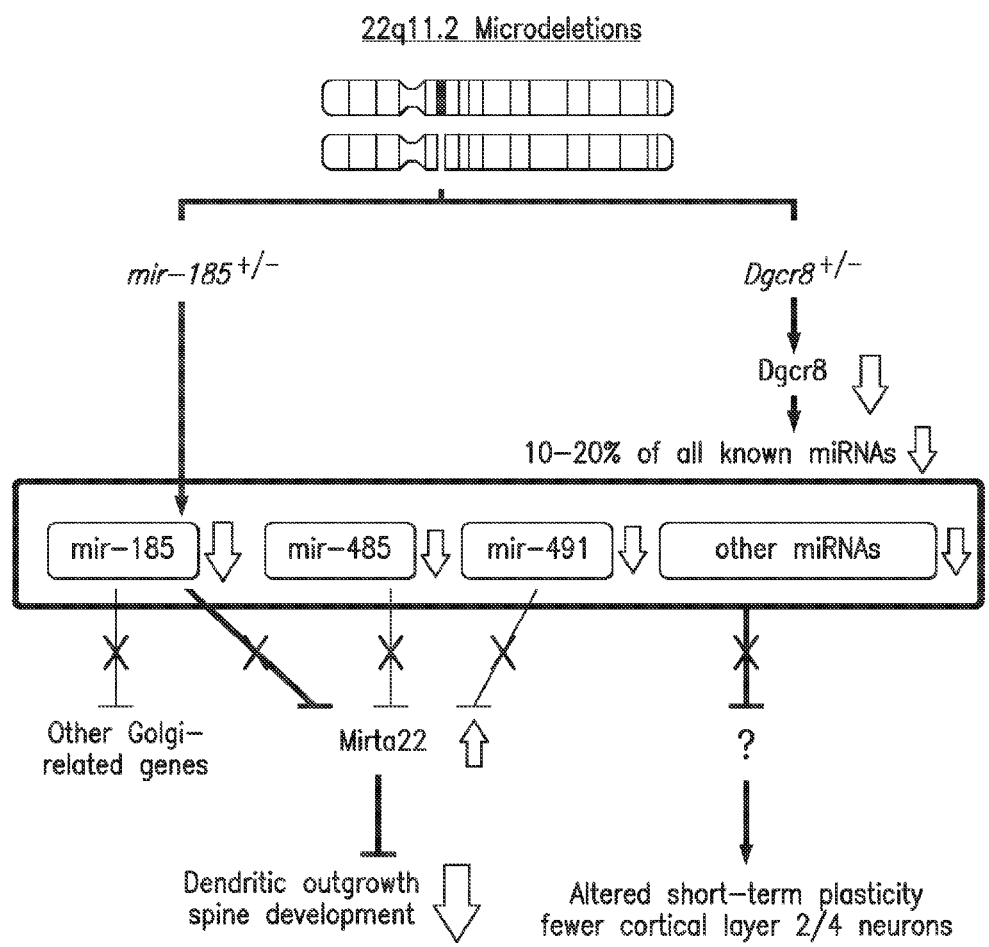

FIG. 25. Schematic outlining the proposed relationship among 22q11.2 microdeletions, miRNA dysregulation, 2310044H10Rik (Mirta22) and neuronal maturation. In normal postnatal development, mir-185, together with other miRNAs (such as mir-485 and mir-491) whose biogenesis is controlled by Dgcr8, repress Mirta22 levels and promote the development of dendrites and spines. In 22q11.2 microdeletion carriers, miRNA biogenesis deficits due to hemizygosity of Dgcr8 along with a drastic reduction in the levels of mir-185 results in protracted elevation of Mirta22 levels, which in turn may impair the growth of dendrites and spines and affect formation and maintenance of neural circuits.

FIG. 26A-E. 2310044H10Rik (Mirta22) Levels Affect Dendritic and Spine Development, Related to FIG. 7. (A) Sholl analysis of dendritic complexity (using 10-µm concentric circles around the soma) of Wt neurons transfected with a plasmid carrying either full length 2310044H10Rik (Mirta22) (n=25) or no insert (n=24) at DIV7 and fixed at DIV9. Increase in branching in Wt neurons transfected with full length 2310044H10Rik (Mirta22), is prevalent throughout the dendritic tree. (B) Sholl analysis of dendritic complexity (using 10-µm concentric circles around the soma) of Df(16)A$^{+/-}$ neurons transfected with either 2310044H10Rik (Mirta22) shRNA (n=29) or scramble shRNA (n=26) at DIV7 and fixed at DIV9. Reduction in branching in Df(16)A$^{+/-}$ neurons is partially reversed by 2310044H10Rik (Mirta22) shRNA, especially in the vicinity of the most proximal dendrites. (C) Reduction in the number of primary dendrites in Df(16)A$^{+/-}$ neurons at DIV9 relative to Wt neurons is reversed by the transfection of a construct that expresses an independent 2310044H10Rik (Mirta22) shRNA (n=16 for Wt+scr shRNA; n=16 for Df(16)A$^{+/-}$ scr shRNA; n=16 for Df(16)A$^{+/-}$+Mirta22 shRNA). Scr shRNA: scramble shRNA. (D) Sholl analysis showing that reduction in branching in Df(16)A$^{+/-}$ neurons is partially reversed by 2310044H10Rik (Mirta22)shRNA, especially in the vicinity of the most proximal dendrites. (E) Reduction in the density of mushroom spines (estimated over 75 µm of dendritic length) in Df(16)A$^{+/-}$ neurons at DIV19 relative to Wt neurons is reversed by the introduction of 2310044H10Rik (Mirta22) shRNA, but not scramble shRNA (n=12 for Wt+scr shRNA; n=12 for Df(16)A$^{+/-}$ scr shRNA; n=12 for Df(16)A$^{+/-}$+Mirta22 shRNA). Values of Df(16)A$^{+/-}$ neurons were normalized to Wt+scr shRNA. Results are expressed as mean±SEM. *p<0.05, p<0.01, *p<0.001 (Student's t-test).

FIG. 27. List of transcripts outside the 22q11.2 syntenic region misregulated in a reciprocal manner, related to FIG. 4.

FIG. 28. Gene Expression profile of predicted mir-185 targets that have Golgi related functions, related to FIG. 23.

5. DETAILED DESCRIPTION OF THE INVENTION

As discussed in the working example below, it was discovered that a consequence of 22q11.2 hemizygous microdeletion is heterozygosity for expression of the microRNA, mir-185. It was further discovered that decreased levels of mir-185 consequent to heterozygosity lead to overexpression of Mirta22, and that overexpression of Mirta22 is associated with changes in neuronal morphology, including decreased numbers of primary dendrites, decreased spine density, and a small but significant reduction in mushroom spine width, all of which are, in turn, associated with decreased neuronal connectivity. According to the invention, neuronal connectivity may be increased by decreasing the activity of Mirta22 and/or increasing the activity of mir-185. Further, as both mir-485 and mir-491 also have binding sites in proximity to Mirta22, the present invention also provides for increasing neuronal connectivity by increasing the activity of mir-485 and/or mir-491.

For clarity of description, and not by way of limitation, the detailed description of the invention is divided into the following subsections:
(i) mir-185, mir-485 and mir-491;
(ii) Mirta22; and
(iii) methods of treatment.

5.1 MIR-185, MIR-485 and MIR-491

The present invention provides for mir-185, mir-485 and mir-491 nucleic acid molecules. These nucleic acid molecules may be comprised of deoxyribonucleotides and/or ribonucleotides and may optionally comprise non-naturally occurring nucleotides, for example phosphorothioate residues, to promote stability. In non-limiting embodiments the mir-185, mir-485 or mir-491 nucleic acid molecules are between about 15 and 100, or between about 15 and 80, or between about 15 and 70, or between about 15 and 60, or between about 15 and 50, or between about 15 and 40, or between about 15 and 30, nucleotides in length or between about 22 and 100, or between about 22 and 80, or between about 22 and 70, or between about 22 and 60, or between about 22 and 50, or between about 22 and 40, or between about 22 and 30, nucleotides in length.

In certain non-limiting embodiments, the present invention provides for murine mir-185 nucleic acid molecules, including, as non-limiting examples, the mir-185 RNA molecule as well as precursors thereof. In certain non-limiting embodiments, the present invention provides for murine mir-185 nucleic acid molecules. Such molecules may comprise the sequence, GenBank Acc. No. NR_029571: agggattggagagaaaggcagttcctgatggtcccctcccagg ggctggctttcctctggtcctt (SEQ ID NO:6), or a sequence at least 95 percent homologous thereto or at least 99 percent homologous thereto (homology, as that term is used herein, may be measured using standard software such as BLAST or FASTA). In related non-limiting embodiments, some or all of the thymidines in SEQ ID NO:6 may be substituted with uridine. For example, a murine mir-185 nucleic acid may comprise the sequence agggauuggagagaaaggcaguuccugaug-guccccucccagggggcuggcuuuccucugguccuu (SEQ ID NO:7). or may comprise the subsequence (miRBase Acc. No. MIMAT0000214) uggagagaaaggcaguuccuga (SEQ ID NO:8). In further embodiments, a murine mir-185 nucleic acid may comprise a 15-21 nucleotide fragment of SEQ ID NO:6 or SEQ ID NO:7 or SEQ ID NO:8.

In certain non-limiting embodiments, the present invention provides for human mir-185 nucleic acid molecules, including, as non-limiting examples, the mir-185 RNA molecule as well as precursors thereof. In certain non-limiting embodiments, the present invention provides for human mir-185 nucleic acid molecules. Such molecules may comprise the sequence, GenBank Acc No. NR_029706: aggggcgagggattggagagaaaggcagttcctgatggtcccctcccca ggggctggctttcctctggt ccttccctccca (SEQ ID NO:9), or a sequence at least 95 percent homologous thereto or at least 99 percent homologous thereto. In related non-limiting embodiments, some or all of the thymidines in SEQ ID NO:9 may be substituted with uridine. For example, a human mir-185 nucleic acid may comprise the sequence: aggggcgagggauuggagagaaaggcaguuccugaugguccccuc-cccagggggcuggcuuuccucuggu ccuucccuccca (SEQ ID NO: 10) or the sequence uggagagaaaggcaguuccuga (SEQ ID NO:8). In further embodiments, a human mir-185 nucleic acid may comprise a 15-21 nucleotide fragment of SEQ ID NO:8 or SEQ ID NO:9 or SEQ ID NO: 10.

In certain non-limiting embodiments, the present invention provides for murine mir-485 nucleic acid molecules, including, as non-limiting examples, the mir-485 RNA molecule as well as precursors thereof. In certain non-limiting embodiments, the present invention provides for murine mir-485 nucleic acid molecules. Such molecules may comprise the sequence, MiRBase Acc. No. MI0003492: ACUUGGAGAGAGGCUGGCCGUGAUGAAU UCGAUUCAUCUAAACGAGUCAUACACGGCUCUC-CUCUCUUUCUAGU (SEQ ID NO:11) or MiRBase Acc. No. MIMAT0003128: AGAGGCUGGC-CGUGAUGAAUUC (SEQ ID NO: 12), or a sequence at least 95 percent homologous thereto or at least 99 percent homologous thereto (homology, as that term is used herein, may be measured using standard software such as BLAST or FASTA). In further embodiments, a murine mir-485 nucleic acid may comprise a 15-21 nucleotide fragment of SEQ ID NO:11 or SEQ ID NO: 12.

In certain non-limiting embodiments, the present invention provides for human mir-485 nucleic acid molecules, including, as non-limiting examples, the mir-485 RNA molecule as well as precursors thereof. In certain non-limiting embodiments, the present invention provides for human mir-485 nucleic acid molecules. Such molecules may comprise the sequence, MiRBase Acc. No. MI0002469: ACUUGGAGAGAGGCUGGCCGUGAUGAAU UCGAUUCAUCAAAGCGAGUCAUACACGGCUCUC-CUCUCUUUUAGU (SEQ ID NO: 13) or MiRBase Acc. No. MIMAT0002175: AGAGGCUGGC-CGUGAUGAAUUC (SEQ ID NO: 14), or a sequence at least 95 percent homologous thereto or at least 99 percent homologous thereto. In further embodiments, a human mir-485 nucleic acid may comprise a 15-21 nucleotide fragment of SEQ ID NO: 13 or SEQ ID NO: 14.

In certain non-limiting embodiments, the present invention provides for murine mir-491 nucleic acid molecules, including, as non-limiting examples, the mir-491 RNA molecule as well as precursors thereof. In certain non-limiting embodiments, the present invention provides for murine mir-491 nucleic acid molecules. Such molecules may comprise the sequence, MiRBase Acc. No. MI0004680: AAUUGACUUAGCUGGGAAGUGGGGAACCCU UCCAUGAGGAGUAGAACACUCCUUAUG-CAAGAUUCCCUUCUACCUGACUGAGUUG A (SEQ ID NO: 15) or MiRBase Acc. No. MIMAT0003486: AGUGGGGAACCCUUCCAUGAGG (SEQ ID NO: 16), or a sequence at least 95 percent homologous thereto or at least 99 percent homologous thereto (homology, as that term is used herein, may be measured using standard software such as BLAST or FASTA). In further embodiments, a murine mir-491 nucleic acid may comprise a 15-21 nucleotide fragment of SEQ ID NO:15 or SEQ ID NO: 16.

In certain non-limiting embodiments, the present invention provides for human mir-491 nucleic acid molecules, including, as non-limiting examples, the mir-491 RNA molecule as well as precursors thereof. In certain non-limiting embodiments, the present invention provides for human mir-491 nucleic acid molecules. Such molecules may comprise the sequence, MiRBase Acc. No. MI0003126: UUGACUUAGCUGGGUAGUGGGGAACCCU UCCAUGAGGAGUAGAACACUCCUUAUG-CAAGAUUCCCUUCUACCUGGCUGGGUUG G (SEQ ID NO: 17), or MiRBase Acc. No. MIMAT0002807: AGUGGGGAACCCUUCCAUGAGG (SEQ ID NO: 18), or a sequence at least 95 percent homologous thereto or at least 99 percent homologous thereto. In further embodiments, a human mir-491 nucleic acid may comprise a 15-21 nucleotide fragment of SEQ ID NO:17 or SEQ ID NO:18.

The present invention further provides for nucleic acid molecules comprising nucleotide sequences that are the complements of any of the above-described nucleotide sequences (SEQ ID NO:6-18).

5.2 Mirta22

The present invention provides for Mirta22, also known in the literature as 2310044H10Rik (murine) and C19orf63 (human).

Figure 6A:
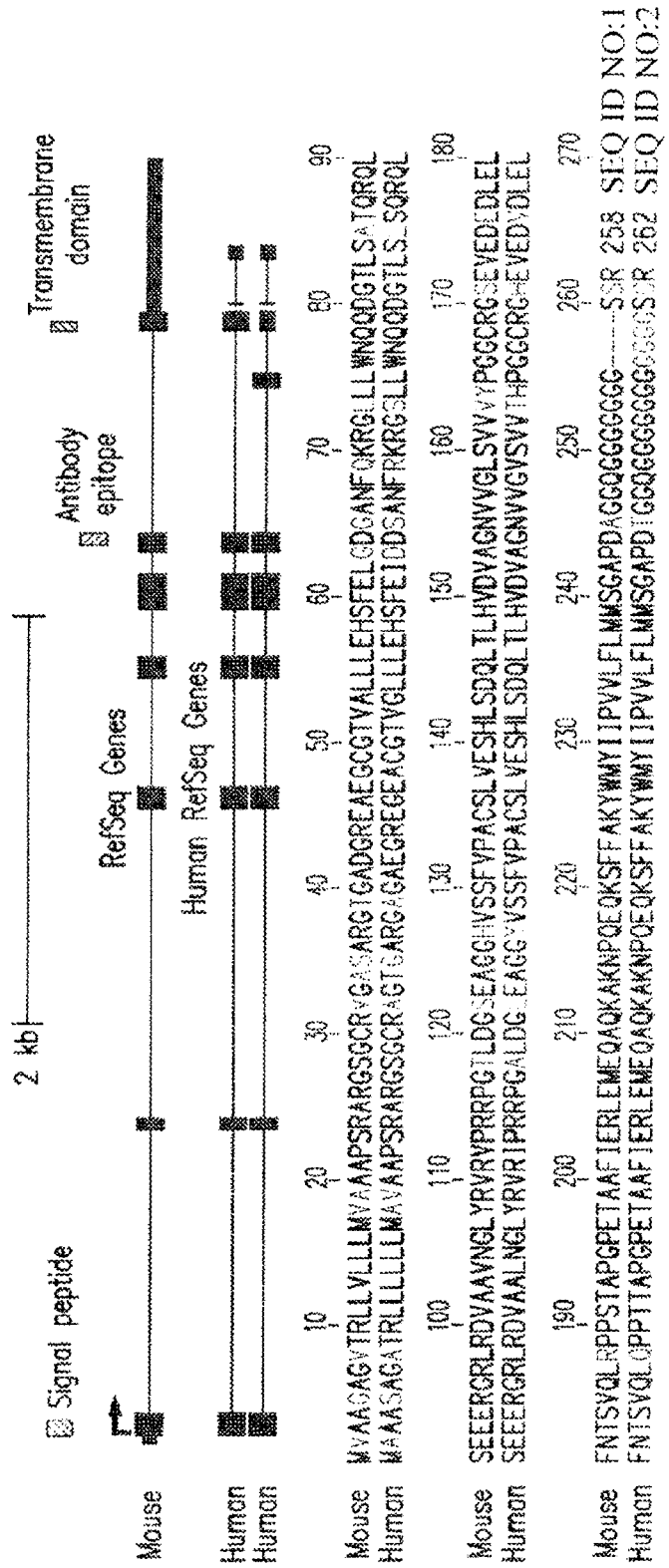

In certain non-limiting embodiments, the present invention provides for a murine Mirta22 protein comprising an amino acid sequence as depicted in FIG. 6A (SEQ ID NO:1) or a subsequence comprising amino acids 11-269 thereof, or a subsequence comprising amino acids 38-269 thereof, or a variant of the complete protein or subsequence that is at least about 95 percent or at least about 99 percent homologous thereto.

In certain non-limiting embodiments, the present invention provides for a nucleic acid encoding a murine Mirta22 protein, as described above. For example, said nucleic acid may comprise the sequence set forth in GenBank Accession No. NM_197991.2 and as depicted in FIG. 16C (SEQ ID NO: 19), or may be at least about 95 percent or at least about 99 percent homologous thereto, or may comprise a subsequence of SEQ ID NO: 19 comprising the coding sequence from nucleotide 115 through 921, or a sequence that is at least about 95 percent or at least about 99 percent homologous thereto, or a nucleic acid that is complementary to any of the foregoing sequences. The present invention further provides for an antisense RNA or interfering RNA ("RNAi") or short hairpin RNA ("shRNA") that comprises a nucleotide sequence complementary to a portion of SEQ ID NO:19 over a region of between about 15 and 35 or between about 15 and 25 nucleotides, where there can be no more than five or no more than four or no more than three or no more than two or no more than one or zero mismatches in complementarity.

In certain non-limiting embodiments, the present invention provides for an antibody or fragment (e.g., Fab or F(ab')2 thereof, or single chain antibody, or diabody, that specifically binds to murine Mirta22 protein, for example a protein having SEQ ID NO: 1. Antibody or the source of antibody fragment may be polyclonal or monoclonal antibody. In a specific, non-limiting embodiment of the invention, the antibody may be directed to the subfragment of murine Mirta22, EQAQKAKNPQEQKSFFAKY (SEQ ID NO:20).

In certain non-limiting embodiments, the present invention provides for a human Mirta22 protein (isotype 1) comprising an amino acid sequence as depicted in FIG. 6A (SEQ ID NO:2), GenBank Accession No. NM_206538.2, MAAASAGATRLLLLLLMAVAAPSRARGSGCRAGT-GARGAGAEGREGEACGTVGLLLE HSFEIDDSAN-FRKRGSLLWNQQDGTLSLSQRQLSEEERGRLRD-VAALNGLYRVRIPRRP GALDGLEAGGYVSSFVPACSLVESHLSDQLTLHVD-VAGNVVGVSVVTHPGGCRGHEVE DVDLELFNTS-VQLQPPTTAPGPETAAFIERLEMEQAQKAKN-PQEQKSFFAKYWMYIIPV VLFLMMSGAPDTGGQGGGGGGGGGGSGR (SEQ ID NO:2) or a subsequence thereof comprising amino acids 28-263, or a variant of the complete protein or subsequence that is at least about 95 percent or at least about 99 percent homologous thereto.

In certain non-limiting embodiments, the present invention provides for a nucleic acid encoding a human Mirta22 protein (isotype 1), as described above. For example, said nucleic acid may comprise the sequence as set forth in GenBank Accession No. NM_206538.2 and as depicted in FIG. 16A (SEQ ID NO:3) or a sequence that is at least about 95 percent or at least about 99 percent homologous thereto, or may comprise a subsequence of SEQ ID NO:3 comprising the coding sequence between nucleotides 67 and 855 (inclusive; all ranges recited in this document are inclusive of their stated limits unless provided otherwise) or a sequence that is at least about 95 percent or at least about 99 percent homologous thereto, or may comprise a subsequence of SEQ ID NO:3 comprising the coding sequence without the portion encoding the signal peptide between nucleotides 148 and 855, or a sequence that is at least about 95 percent or at least about 99 percent homologous thereto, or a nucleic acid that is complementary to any of the foregoing sequences. The present invention further provides for an antisense RNA or RNAi or shRNA comprising a nucleotide sequence that is complementary to a portion of SEQ ID NO:3 over a region of between about 15 and 35 or between about 15 and 25 nucleotides, where there can be no more than five or no more than four or no more than three or no more than two or no more than one or zero mismatches in complementarity.

In certain non-limiting embodiments, the present invention provides for an antibody or fragment (e.g., Fab or F(ab')2 thereof, or single chain antibody, or diabody, that specifically binds to human Mirta22 protein, for example a protein having SEQ ID NO:2, Antibody or the source of antibody fragment may be polyclonal or monoclonal antibody. In a specific, non-limiting embodiment of the invention, the antibody may be directed to the sub fragment of human Mirta22 sharing the sequence with the murine protein, EQAQKAKNPQEQKSFFAKY (SEQ ID NO: 20).

In certain non-limiting embodiments, the present invention provides for a human Mirta22 protein (isotype 2) comprising an amino acid sequence as depicted in GenBank Accession No. NM_175063.4, MAAASAGATRLLLLLL-MAVAAPSRARGSGCRAGTGARGAGAEGR EGE-ACGTVGLLLEHSFEIDDSANFRKRGSLLWN-QQDGTLSLSQRQLSEEERGRLRDVAA LNGLYRVRIPRRPGALDGLEAGGYVSSFVPACSLVES-HLSDQLTLHVDVAGNWGVSV VTHPGGCRGHEVED-VDLELFNTSVQLQPPTTAPGPETAAFIERLE-MEQAQKAKNPQE QKSFFAKYWHIILGGAVLLTALRPAAPGPAPPPQEA (SEQ ID NO:4), or a subsequence thereof comprising amino acids 28-263, or a variant of the complete protein or subsequence that is at least about 95 percent or at least about 99 percent homologous thereto.

In certain non-limiting embodiments, the present invention provides for a nucleic acid encoding a human Mirta22 protein (isotype 2), as described above. For example, said nucleic acid may comprise the sequence as set forth in GenBank Accession No. NM_175063.4 and as depicted in FIG. 16B (SEQ ID NO:5) or a sequence that is at least about 95 percent or at least about 99 percent homologous thereto, or may comprise a subsequence of SEQ ID NO:5 comprising the coding sequence between nucleotides 67 and 831 or a sequence that is at least about 95 percent or at least about 99 percent homologous thereto, or may comprise a subsequence of SEQ ID NO: 5 comprising the coding sequence without the portion encoding the signal peptide between nucleotides 148 and 831, or a sequence that is at least about 95 percent or at least about 99 percent homologous thereto, or a nucleic acid that is complementary to any of the foregoing sequences. The present invention further provides for an antisense RNA or RNAi or shRNA comprising a nucleotide sequence that is complementary to a portion of SEQ ID NO:5 over a region of between about 15 and 35 or between about 15 and 25 nucleotides, where there can be no more than five or no more than four or no more than three or no more than two or no more than one or zero mismatches in complementarity.

In certain non-limiting embodiments, the present invention provides for an antibody or fragment (e.g., Fab or F(ab')2 thereof, or single chain antibody, or diabody, that specifically binds to human Mirta22 protein, for example a protein having SEQ ID NO:4. Antibody or the source of antibody fragment may be polyclonal or monoclonal antibody. In a specific, non-limiting embodiment of the invention, the antibody may be directed to the subfragment of human Mirta22 sharing the sequence with the murine protein, EQAQKAKNPQEQKSFFAKY (SEQ ID NO:20).

5.3 Methods of Treatment

In certain non-limiting embodiments, the present invention provides for a method for increasing connectivity between neurons comprising administering to said neurons an effective amount of an agent that inhibits Mirta22 activity.

"Increasing connectivity between neurons" includes increasing the number of primary dendrites and/or increasing the spine density and/or increasing the width of mushroom spines on neurons and/or increasing the number of synapses.

The method for increasing connectivity between neurons may be practiced in vitro or in vivo.

The neurons in said methods may be human or non-human neurons.

"Inhibits Mirta22 activity" includes reducing and/or antagonizing Mirta22 activity. Agents that inhibit Mirta22 activity may act, for example, by reducing transcription or translation or processing of Mirta22 or by antagonizing the function of Mirta22, for example by binding to it such as to reduce or prevent it from performing its natural function.

Agents that inhibit Mirta22 activity include, but are not limited to, mir-185, mir-485, mir-491, antisense RNA comprising a sequence complementary to the Mirta22 mRNA; RNAi comprising a sequence complementary to the Mirta22 mRNA, shRNA comprising a sequence complementary to the Mirta22 mRNA, an anti-Mirta22 antibody or fragment thereof, a single chain antibody that specifically binds to Mirta22, or a diabody that specifically binds to Mirta22.

In certain non-limiting embodiments, the present invention provides for a method for increasing connectivity between neurons comprising administering to said neurons an effective amount of an agent that increases mir-185 activity.

"Increasing mir-185 activity" includes increasing the amount or functionality of mir-185. For example, but not by way of limitation, agents that increase mir-185 activity include a mir-185 nucleic acid, as well as agents that promote mir-185 functionality, for example agents that increase the activity of Dgcr8 including Dgcr8 protein or a nucleic acid encoding Dgcr8 protein. Agents that directly increase mir-185 activity include mir-185 nucleic acid. Agents that indirectly increase mir-185 include agents that increase the activity of Dgcr8.

In certain non-limiting embodiments, the present invention provides for a method for increasing connectivity between neurons comprising administering to said neurons an effective amount of an agent that increases mir-485 activity.

"Increasing mir-485 activity" includes increasing the amount or functionality of mir-485. For example, but not by way of limitation, agents that increase mir-485 activity include a mir-485 nucleic acid, as well as agents that promote mir-485 functionality, for example agents that increase the activity of Dgcr8 including Dgcr8 protein or a nucleic acid encoding Dgcr8 protein. Agents that directly increase mir-485 activity include mir-485 nucleic acid. Agents that indirectly increase mir-485 include agents that increase the activity of Dgcr8.

In certain non-limiting embodiments, the present invention provides for a method for increasing connectivity between neurons comprising administering to said neurons an effective amount of an agent that increases mir-491 activity.

"Increasing mir-491 activity" includes increasing the amount or functionality of mir-491. For example, but not by way of limitation, agents that increase mir-491 activity include a mir-491 nucleic acid, as well as agents that promote mir-491 functionality, for example agents that increase the activity of Dgcr8 including Dgcr8 protein or a nucleic acid encoding Dgcr8 protein. Agents that directly increase mir-491 activity include mir-491 nucleic acid. Agents that indirectly increase mir-491 include agents that increase the activity of Dgcr8.

In related non-limiting embodiments, the present invention provides for a method for increasing connectivity between neurons in a subject in need of such treatment comprising administering to said subject an effective amount of an agent that inhibits Mirta22 activity.

A subject in need of such treatment is a subject who suffers from schizophrenia or a related disorder or a subject who has a disorder of memory or learning or a subject who would benefit from enhancement of neural connectivity or memory or learning capabilities. A subject may be a human or non-human subject.

Schizophrenia-related disorders include but are not limited to brief psychotic disorder, schizophreniform disorder, schizoaffective disorder, and delusional disorder.

Disorders of memory include, but are not limited to, Alzheimer's disease, Lewy body dementia, vascular dementia, corticobasal degeneration, Creuzfeld-Jacob disease, frontotemporal dementia, Huntington's disease, mild cognitive impairment, progressive supranuclear palsy, and Picks disease.

Disorders of learning include, but are not limited to, attention deficit hyperactivity disorder, dyslexia, dyscalcula, nonverbal learning disorder and mental retardation.

Additional subjects that may benefit from treatment according to the invention include, but are not limited to, subjects suffering from autism, Asperger's syndrome, depression, bipolar disorder, obsessive compulsive disorder, and subjects suffering from memory or learning deficits secondary to cerebral infarction, surgical, radiologic, or chemotherapeutic treatment of the brain, or trauma. The present invention provides for a method for increasing connectivity between neurons in such subjects comprising administering to said subject an effective amount of an agent that inhibits increases mir-185, mir-485 and/or mir-491 activity and/or inhibits Mirta22 activity.

In certain non-limiting embodiments, the present invention provides for a method of treating schizophrenia or a related disorder in a subject, comprising administering to said subject an effective amount of an agent that inhibits Mirta22 activity.

In certain non-limiting embodiments, the present invention provides for a method of treating schizophrenia or a related disorder in a subject, comprising administering to said subject an effective amount of an agent that increases mir-185, mir-485 and/or mir-491 activity.

In certain non-limiting embodiments, the present invention provides for a method of enhancing memory in a subject, comprising administering to said subject an effective amount of an agent that inhibits Mirta22 activity.

In certain non-limiting embodiments, the present invention provides for a method of enhancing memory in a subject, comprising administering to said subject an effective amount of an agent that increases mir-185, mir-485 and/or mir-491 activity.

Enhancement of memory may be determined using standard tests. In non-human animals, for example, memory may be tested using performance in a passing through a maze. In humans, memory may be tested, for example but not by way of limitation, using the Mini-Mental State Exam or the Wechsler Memory Scale.

In any of the foregoing, the species of origin of nucleic acids or antibodies or related molecules being utilized is preferably the same as or closely related to the species of the neurons or subject being treated.

According to the invention, the agent may be administered by any route, including but not limited to intrathecal, intravenous, nasal, intraarterial, oral, intramuscular, subcutaneous, pulmonary, intraperitoneal, etc.

The present invention provides for pharmaceutical compositions comprising an agent for use according to the invention in a suitable carrier, such as, but not limited to, normal saline or sterile water.

The present invention is exemplified but not limited by the following working example, which sets for additional specific non-limiting embodiments of the present invention. The contents of the working example are hereby incorporated by reference into the detailed description of the invention.

6. WORKING EXAMPLE

6.1 Materials and Methods

Mice, qRT-PCR and Expression Profiling.

Generation of Df(16)A$^{+/-}$ and Dgcr8$^{+/-}$ mice is described in (8). Total RNA was isolated by miRNeasy mini kit. qRT-PCR was performed as described in (8). For expression profiling, cDNA was generated and exposed to the Affymetrix Mouse genome 430 2.0 array, which includes 45,000 probe sets from 34,000 well characterized mouse genes. Data were obtained using GeneChip Analysis Software Microarray Suite version 5 and analyzed with limma package in the bioconductor project (www.bioconductor.org)_.

Analysis of Dendritic Complexity and Spine Morphology.

Dissected E17 hippocampal neurons were plated at 2×10$^5$ cells/ml in 6-well plates and cultured for 9-19 days, depending on the experiments. Images of basal dendrites and dendritic spines were acquired as described previously (9). An experimenter blind to the genotype performed imaging and analysis. Semi-automatic tracing and quantification was performed using ImageJ and NeuroStudio (30,31). The number of primary dendrites and total branch points for each treatment condition were calculated by L-measure [version 4.0](32). Statistics were conducted using Student's t-test (number of primary dendrites and branch points, as well as spine density) and Kolmogorov-Smirnov test (width of mushroom spines).

Luciferase Assay.

Mirta22 3'UTR was cloned into psiCHECK2. Binding site mutant clones were generated by PCR-based mutagenesis. N18 neuroblastoma cells were transfected with various psiCHECK2 reporter constructs together with pre-mir-185 mimic or pre-scramble control unless mentioned otherwise and luciferase assays were performed using the Promega Dual-Luciferase Reporter Assay System. All experiments were performed at least 2 times and all data presented is the average of 3 technical repeats.

Antibodies.

A 20 amino acid peptide ([H]-CEQAQKAKNPQEQKSF-FAKY-[NH2]) (SEQ ID NO:21) was used to generate a rabbit polyclonal antibody. The specificity of the antibody was determined as described in FIG. 11. Western blot, immunohistochemistry and immunocytochemistry assays were conducted as previously described (8,9).

In Situ Hybridization.

Digoxigenin tail labeled anti-mir-185 locked nucleic acid (LNA) and scramble LNA oligonucleotides were obtained from Exiqon. In situ hybridization was conducted as described previously (33).

qRT-PCR and Primers.

Total RNA was isolated from brain or culture cells using the miRNeasy mini kit (QIAGEN) according to manufacturer's instructions. qRT-PCR was performed as described in detail previously (8). The sequences of primers used are as follows:

```
                                     (SEQ ID NO:22),
   Mirta22:    F: CTGCTGTCAATGGCCTCTAC
                                     (SEQ ID NO:23)
               R: GTCCGAAAGGTGCGACTC
                                     (SEQ ID NO:24)
   Hybridization probe: CATGGCCGCCAGCTTCTGA
   mmu-miR-185: ABI Taqman assay ID 002271
```

Neuronal Culture and Transfection.

Dissociated neurons were isolated from E17 mouse embryos and plated at 2×10$^5$ cells/ml in 6-well plates containing glass coverslips coated with poly-D-lysine. Neurons were cultured for 9-19 days, depending on the experiments. A pRFP-C-2310044H10Rik shRNA and pRFP-C-scramble shRNA control (Origene), a Mirta22 (2310044H10Rik) cDNA clone (Origene), as well as pre-mir-185 mimic and a pre-scramble control (Ambion) were used for high efficiency calcium-phosphate mediated transfections as described previously (34). For all experiments, 5 µg of total plasmids and/or 100 pmol of pre-miRNA mimics were used per well.

Analysis of Dendritic Complexity.

Images of basal dendrites were acquired as described previously (9). An experimenter blind to the genotype performed all imaging and analysis. The basal dendrite branches were semi-automatically traced from the somata of neurons using NeuronStudio (31). The .swc files were imported into L-measure (32). The number of primary dendrites and total branch points for each treatment condition were calculated by L-measure (version 4.0). Statistical analysis was conducted using the Student's t-test as implemented in L-measure. Sholl analysis was conducted in ImageJ (http://rsbweb.nih.gov/ij/) using the "Sholl analysis" plugin (http://biology.ucsd.edu/labs/ghosh/software/Sholl-Analysis.pdf). The results were combined in the MS-Excel and a student t-test was conducted to determine the intersection number and significance at each step size between the experimental group and the controls.

Analysis of Spine Morphology.

Images of dendritic spines were acquired as described previously (9). For each experiment. images across all genotypes were acquired with similar optimal settings for laser power, detector gain, and amplifier offset. An experimenter blind to the genotype performed all imaging and analysis. Quantification of spine density, length, and width was performed using ImageJ and NeuroStudio30. One basal dendrite, each at least 75 µm in length from the first branch point. was analyzed per neuron. We analyzed at least 4 neurons from each animal. Spine width was measured as the distance of a straight line drawn across the widest part of the spine head. Changes in spine density between groups were assessed by Student's t-test. The distribution of width of mushroom spines was compared using the Kolmogorov-Smirnov test.

Expression Profiling.

A total of 48 PFC and 48 HPC from 12 Df(16)A$^{+/-}$ mutants and 12 WT littermate control mice at E17 and P6 were dissected and processed using standard protocols recommended by Affymetrix. RNA quality was assessed with Bioanalyzer (Agilent Technologies) and all RNAs had a RIN>7.0. For hybridization, cRNA was exposed to the Affymetrix Mouse genome 430 2.0 array, which includes 45,000 probe sets from 34,000 well characterized mouse genes, and then scanned (Agilent). Sequence clusters were created and refined from the UniGene and the Whitehead Institute Center for Genome Research databases.

Microarray Data Analysis.

Initial intensity files (CEL files) were obtained from microarray images using GeneChip (Affymetrix) Analysis Software Microarray Suite version 5 (Affymetrix) and analyzed with limma package in the bioconductor project (www.bioconductor.org). Data analysis of Df(16)A$^{+/-}$ and Wt littermate expression profiling at E17 and P6 was performed as previously described (8). Briefly, the raw intensity data were first normalized by the Robust Multichip Average (RMA) method, linear models were applied and differential expression was determined by limma package. The gene list was ranked according to their nominal P values and the significance level was estimated by adjusting P values using Benjamini and Hochberg FDR35 to control false positive rate due to multiple testing.

Functional and Geneset Enrichment Analysis of Predicted miR-185 Targets.

miR-185 target predictions were obtained using TargetScan Mouse v5.2. The gene list was imported into DAVID gene functional annotation database. 92% (2708 out of 2932) predicted targets genes were mapped into the DAVID database. Functional annotation was conducted using the program's functional annotation clustering analysis with default settings. The gene list from the top cluster ("Golgi apparatus") was converted into Affymetrix IDs using the DAVID ID conversion tool and further mapped to the corresponding IDs of the Affymetrix mouse 430 2.0 chip. This final probeset list was used as a user-defined geneset for downstream analysis. Geneset enrichment analysis was conducted using the ErmineJ software (38). Analysis was conducted using the receiver operator characteristic (ROC) analysis based on p value rankings.

Luciferase Assays.

Mirta22 3'UTR was cloned into XhoI and NotI sites of psiCHECK2 (Promega). Binding site mutant clones were generated by PCR-based mutagenesis. Site Mut1 sequence (starting from position 289 in 3'UTR): GGAgtTTGC-CAAGCTCggTaaA (SEQ ID NO:25; lower case letters denote altered nucleotide). Site Mut2 sequence (starting from position 350): AtTGTCACgCTaaA (SEQ ID NO:26). Mutations are predicted by RNAhybrid36 to disrupt the binding of mir-185 at the seeds and secondary binding sites. N18 neuroblastoma cells were transfected with various psiCHECK2 reporter constructs (100 ng per well of a 24-well plate) together with pre-mir-185 mimic or pre-scramble control (1 nM=0.5 pmol), unless mentioned otherwise, and luciferase assays were performed 24 hrs post-transfection using the Dual-Luciferase Reporter Assay System (Promega) under the manufacturer's instructions. All experiments were performed at least 2 times and all data presented is the average of 3 technical repeats.

Antibody Production.

A 20 amino acid peptide ([H]-CEQAQKAKNPQEQKSF-FAKY-[NH2]) (SEQ ID NO:21) was designed, synthesized and conjugated to KLH (Keyhole Limpet Hemocyanin) and then injected into rabbits using Covance custom antibody production service (Covance). Antibody serum was then purified using Melon Gel IgG purification Kit (Thermo Scientific) and the purified antibody was used for western blot (1:50), immunohistochemistry and immunocytochemistry assays (1:25).

Figures 13A, 13B:
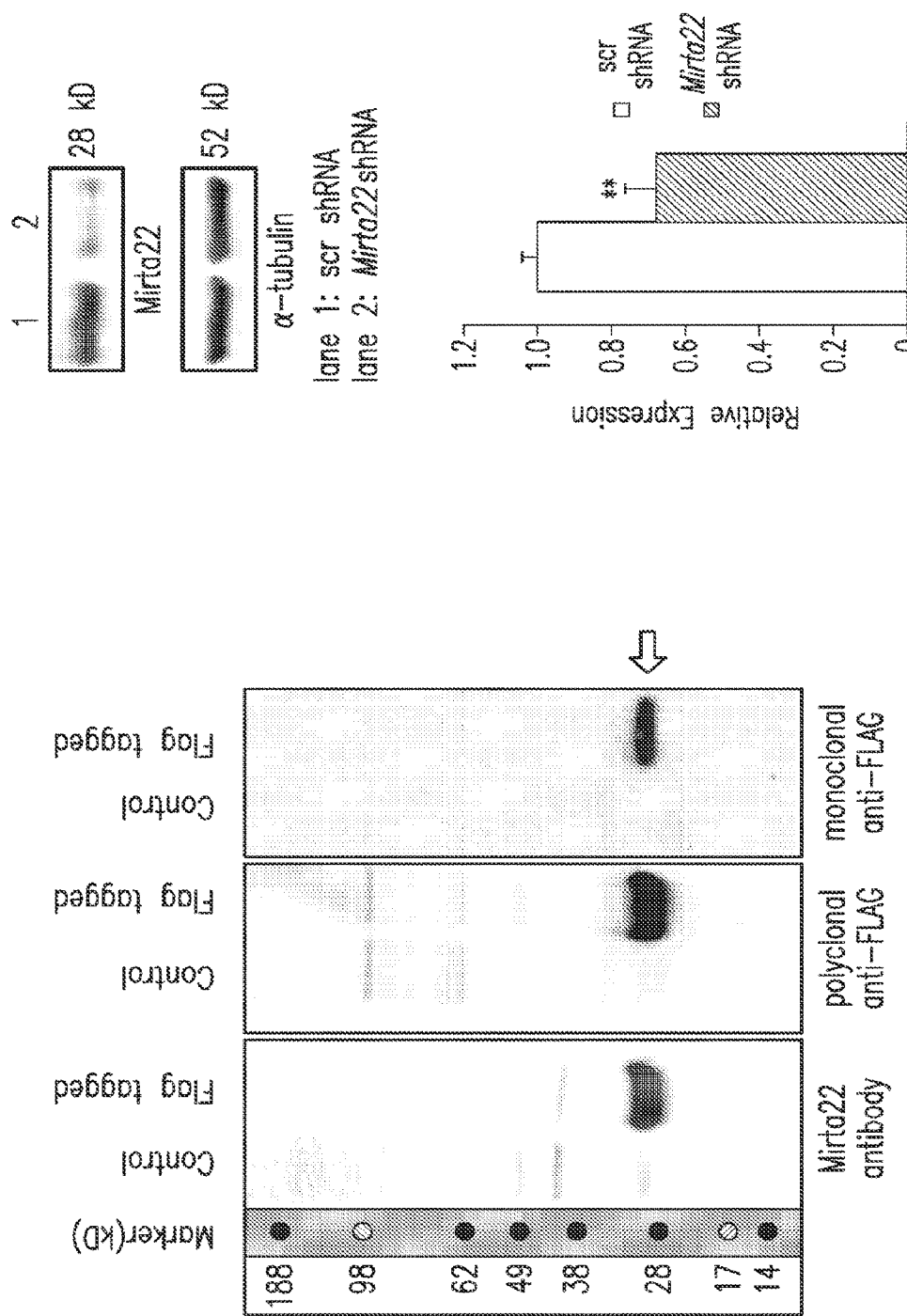
Figure 13D:
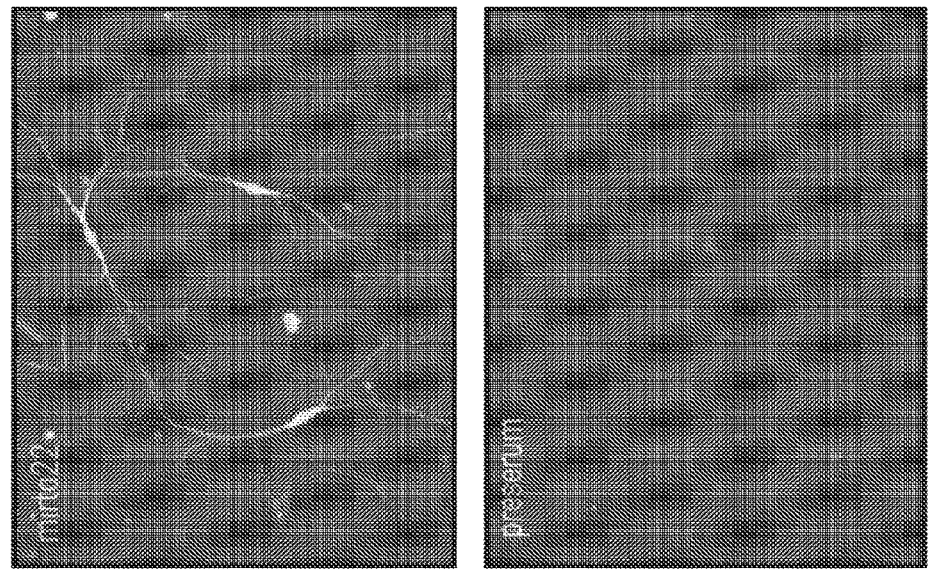

In western blot assays of 293T cell lysates, the purified antibody specifically recognized overexpressed full length Mirta22 tagged with C-terminal FLAG (28 kD), which was independently verified using both polyclonal and monoclonal anti-FLAG antibodies (FIG. 13A). The specificity of the antibody was tested in western blot assays of protein extracts from N18 cells transfected with a 2310044H10Rik shRNA or a full length 2310044H10Rik cDNA plasmid. The intensity of the band at ~28 kD, changed as predicted for each manipulation (FIG. 13B, C). Finally, when used to stain cultured neurons the antibody generated a specific staining pattern whereas the pre-immune serum failed to show signal (FIG. 13D).

Western Blot Assays.

The western blot procedure has been described previously (8). Briefly, equal amounts of protein were separated and then transferred onto an ECF plus membrane. The membrane was probed with 1:50 purified Mirta22 antibody and then with 1:5000 horseradish peroxidase conjugated secondary antibody. The washed membrane was incubated with HRP substrate and chemiluminence images were obtained using Alpha imaging system.

Immunohistochemistry Assays.

Immunohistochemistry assays were conducted according to (37). Briefly, fresh brains were dissected and immediately frozen in OCT. Brains were then sliced at a thickness of 15-20 μm and brain sections were dried at room temperature and then fixed. Sections were incubated overnight with one or two primary antibodies and subsequently incubated for 1 hr with secondary antibody coupled to the Alexa Fluor fluorochromes (1:1,000, Invitrogen). Images were examined under a fluorescence microscope (Nikon).

Immunocytochemistry Assays.

Cells were cultured on coverslips, fixed, permeabilized, and then exposed to primary antibodies and secondary antibodies as described previously (9). Images were examined under a fluorescence microscope (Nikon). For quantification of Mirta22 signals, images were acquired as described previously (9). The raw LSM images were projected and exported using ImageJ. Mirta22 immunocytochemical signal from cell body of each individual neuron was calculated as total integrated density minus background of the cell body area.

6.2 Results

Using chromosomal engineering, we generated a mouse model carrying a hemizygous 1.3-Mb chromosomal deficiency on mouse chromosome 16 [Df(16)A], which is syntenic to the 22q11.2 1.5-Mb microdeletion (FIG. 1A-D) (8). Analysis of Df(16)A$^{+/-}$ mice provided evidence for abnormalities in dendritic morphogenesis and formation of dendritic spines of hippocampal pyramidal neurons both in culture and in vivo (8,9). Such changes may account, at least in part, for the regional decreases in grey matter volumes observed in some 22q11.2 deletion carriers (10). Even modest alterations in dendritic and spine formation may result in a suboptimal number of synaptic connections, formation of inappropriate connections or changes in the integration of synaptic inputs, and may ultimately lead to considerable changes in information processing (11,12).

The Df(16)A$^{+/-}$ strain also provided compelling evidence that the 22q11.2 deletion results in abnormal processing of brain microRNAs (miRNAs), a class of small, noncoding RNAs that regulate the stability and translation of mRNAs (13-16). One gene disrupted by the 22q11.2 microdeletion is Dgcr8, a component of the 'microprocessor' complex that is essential for miRNA production (17). Dgcr8$^{+/-}$ mice were generated (FIG. 2A-E). Dgcr8 haploinsufficiency results in the downregulation of a specific subset of mature miRNAs and contributes to a number of cellular, synaptic and behavioral alterations found in Df(16)A$^{+/-}$ mice (8,18). miRNA dysregulation likely accounts for a fraction of the transcript misexpression observed in the brains of Df(16)A$^{+/-}$ mice but direct targets of the affected miRNAs have hitherto not been reported. The present experiments highlight an important component of this dysregulation and identify a previously uncharacterized gene as a major miRNA transcriptional target mediating the effects of the 22q11.2 microdeletions on neuronal maturation and connectivity.

A Drastic Reduction of miR-185 Levels in Df(16)A$^{+/-}$ Mice.

Figure 3A:
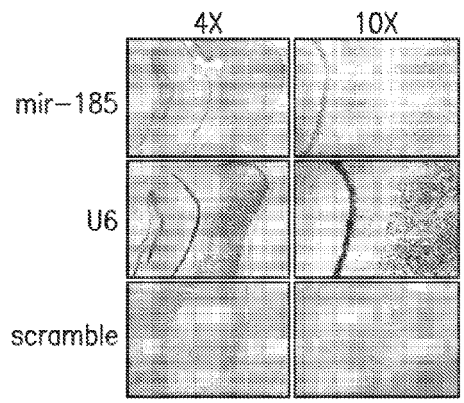
Figure 3B:
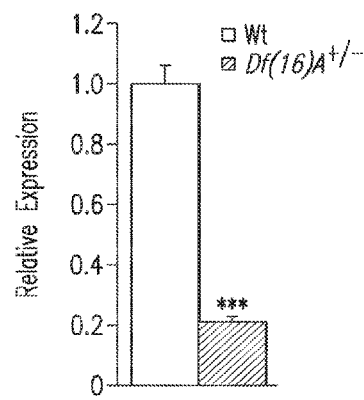
Figure 3C:
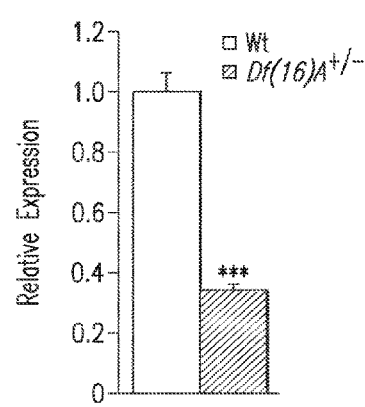
Figure 3D:
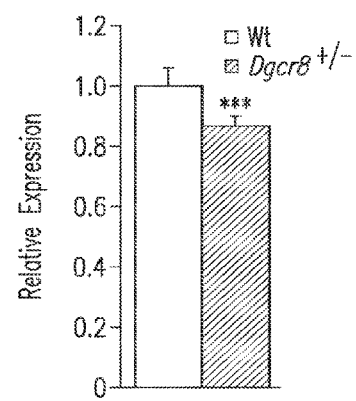
Figure 3E:
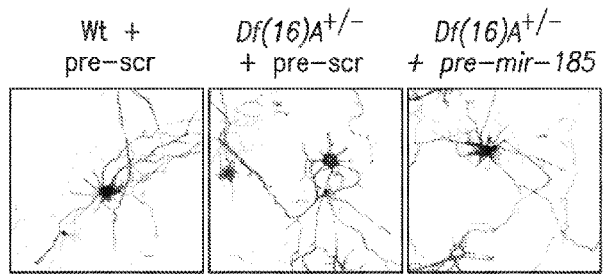

Studies in the Df(16)A$^{+/-}$ mouse strain have shown that the 22q11.2 microdeletion results in abnormal processing of a specific subset of brain miRNAs due to the removal of one copy of the Dgcr8 gene and decrease in its expression in the adult brain (8) as well as earlier in the development (FIG. 8). It is noteworthy that, in addition to Dgcr8, the 22q11.2 microdeletion and the equivalent mouse deficiency remove one miRNA gene (mir-185) located within the minimal 1.5-Mb 22q11.2 critical region (FIG. 1A). In situ hybridization assays indicated that mir-185 is expressed in several brain regions such as hippocampus (HPC) and cortex (FIG. 3A), including frontal cortex. Quantitative real-time PCR (qRT-PCR) analysis showed that expression of mature mir-185 is dramatically reduced by ~70-80% in both HPC ($P<10-6$) and prefrontal cortex (PFC, $P<10-11$) of adult Df(16)A$^{+/-}$ mice (FIG. 3B, C). This reduction was also observed at earlier developmental stages (E17 and P6) (FIG. 9A, B). mir-185 showed a more modest decrease in Dgcr8$^{+/-}$ mice (~20% in HPC, $P<0.05$; FIG. 3D) suggesting that the severe reduction of mature mir-185 expression in Df(16)A$^{+/-}$ mice is due to a combined effect of hemizygosity of mir-185 gene and impaired maturation of the pri-mir-185 transcript produced from the remaining copy, due to the reduction in the Dgcr8 levels. This represents a genuine gene X gene interaction within a pathogenic CNV that results in reduction of the expression of a resident gene considerably greater than expected by the 50% decrease in gene dosage. Such large reduction in relative expression is unique among genes affected by the microdeletion and may represent an important and previously unappreciated component of the 22q11.2-associated miRNA dysregulation. As such, drastically diminished mir-185 activity may lead, either on its own or in combination with other miRNAs affected due to the Dgcr8 deficiency, to altered developmental regulation of one or more target genes and impact a number of neural processes.

Altered miR-185 Levels Contribute to Structural Alterations of Df(16)A$^{+/-}$ Neurons.

miRNAs have been shown to affect structural indices of neuronal connectivity, such as dendritic tree and dendritic spine development (19-21). 22q11.2 microdeletion results in impaired dendritic tree and dendritic spine development in the brain and these deficits are recapitulated in primary neuronal cultures. Impaired dendritic tree and dendritic spine development could be partially accounted for by the 50% decrease in the levels of Dgcr8 but it remained unknown whether reduction in the levels of mir-185 also contributes (8,9,18). Localization of Mirta22 within the Golgi apparatus and dendritic shafts suggests that diminishment of the repressive influence of miR-185 on Mirta22 levels may also contribute to these deficits.

Figure 5A:
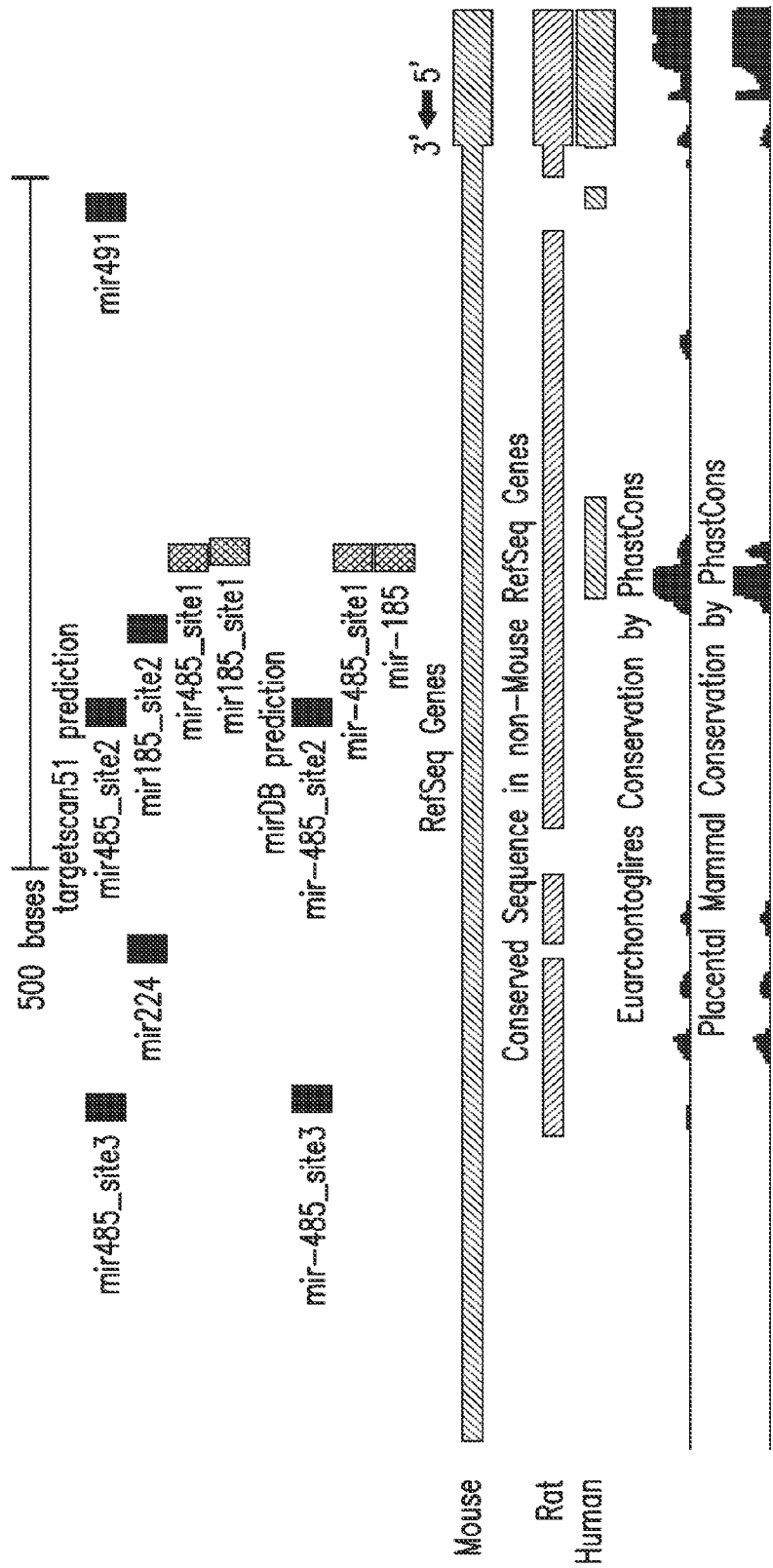
Figure 5B:
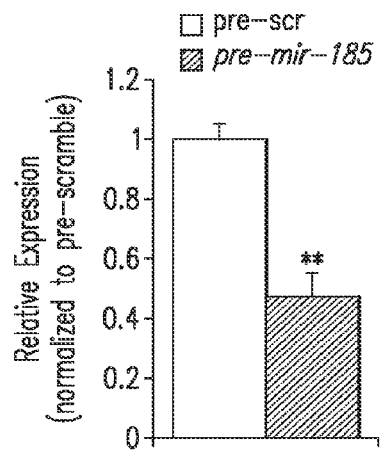
Figure 5C:
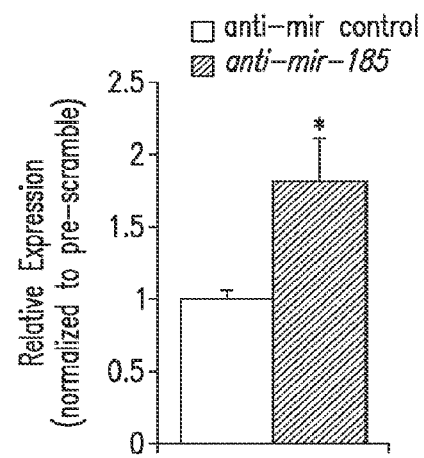
Figure 17A:
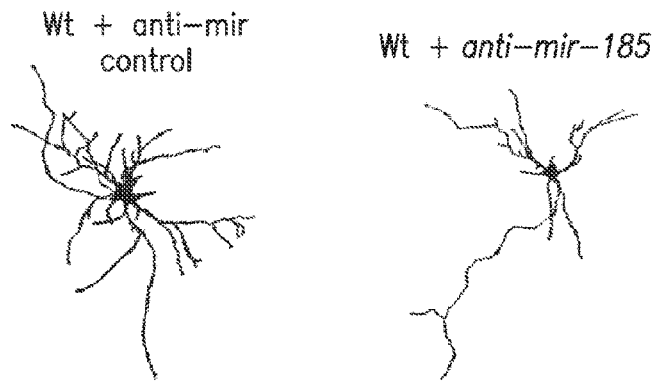
Figure 17B:
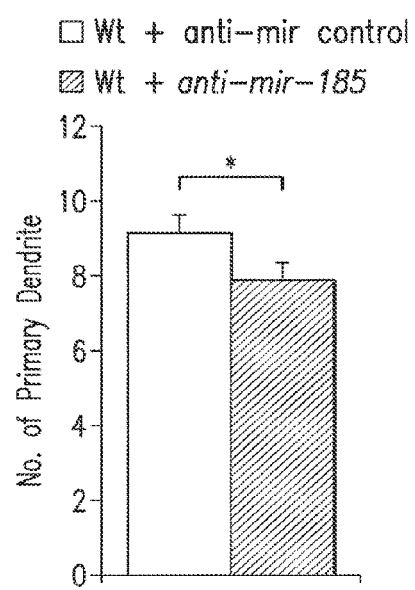
Figure 17C:
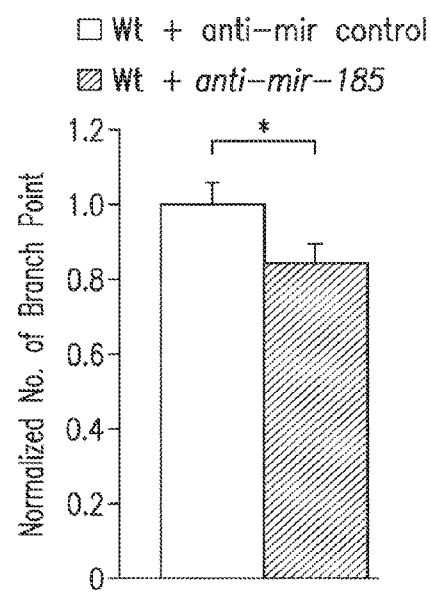
Figure 17D:
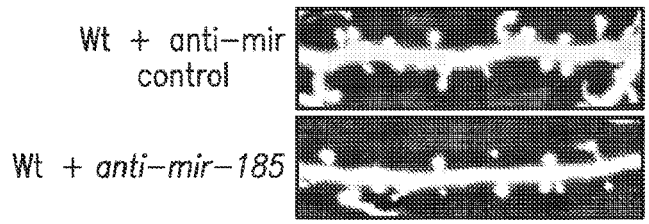
Figure 17E:
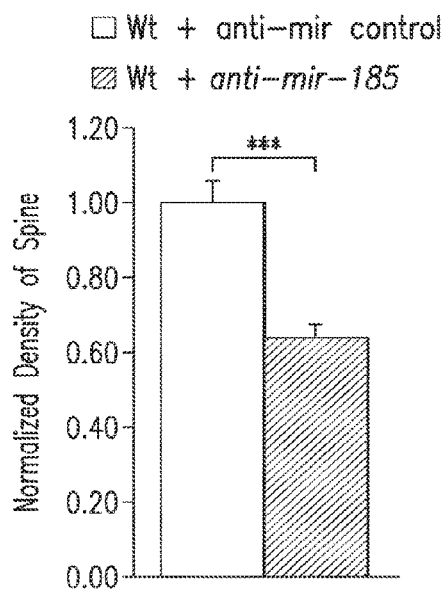
Figure 17F:
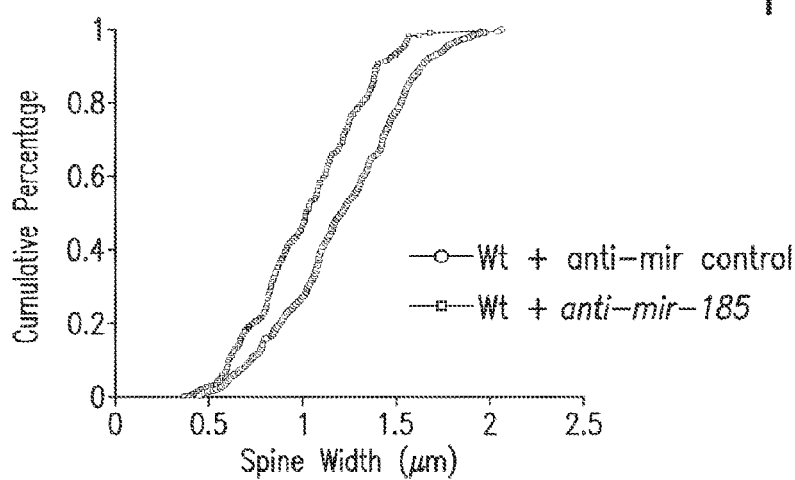
Figure 18A:
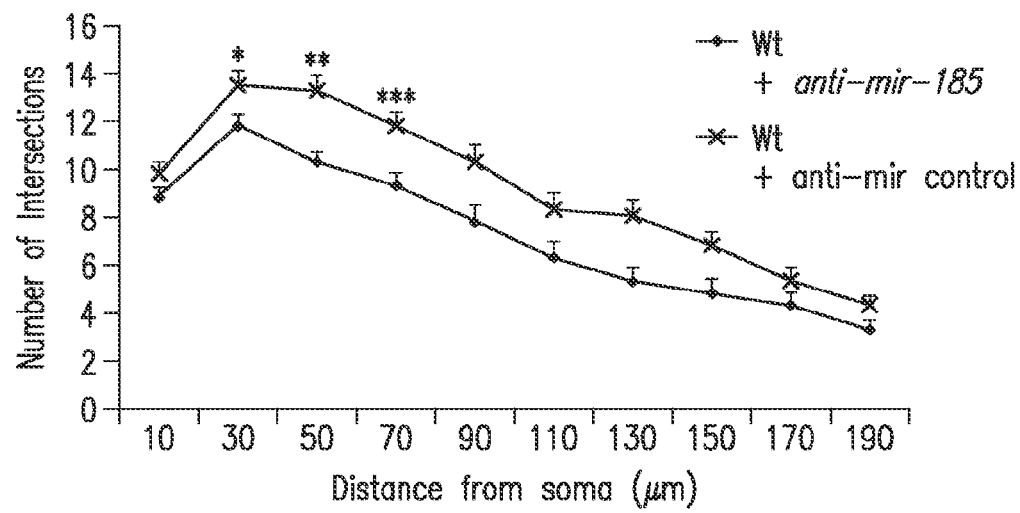
Figure 18B:
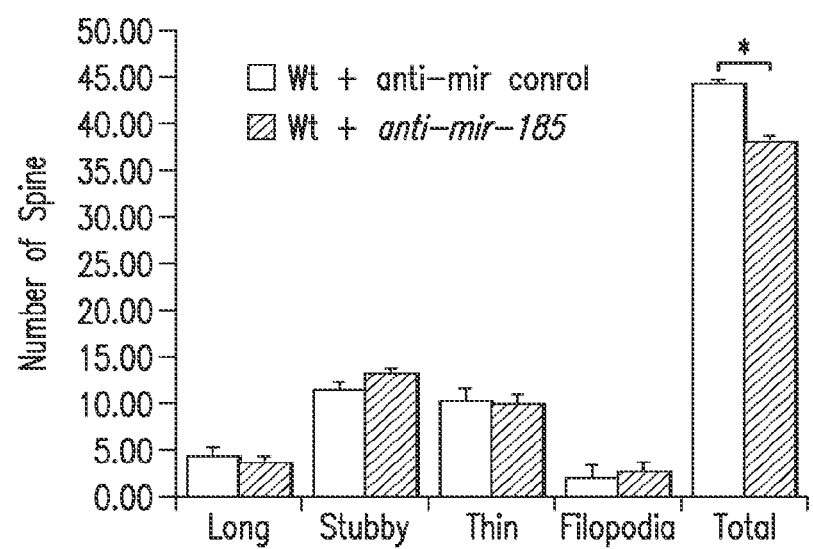
Figure 18C:
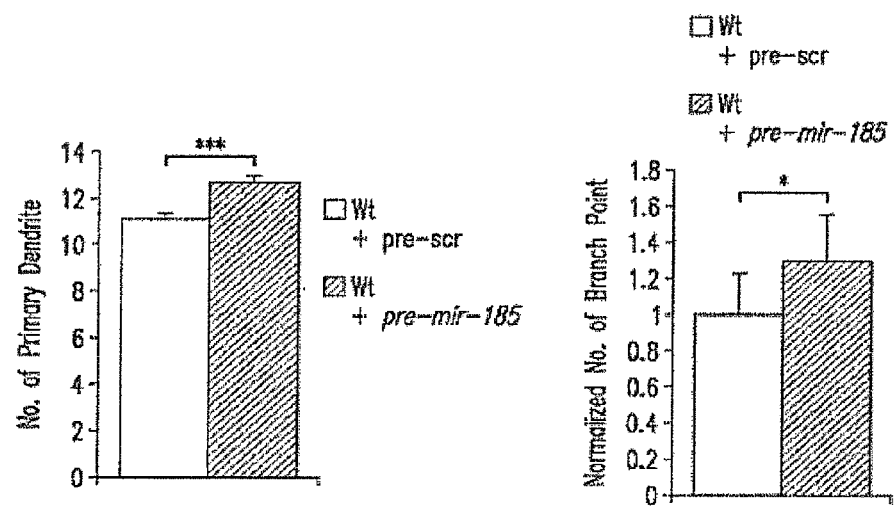
Figure 18D:
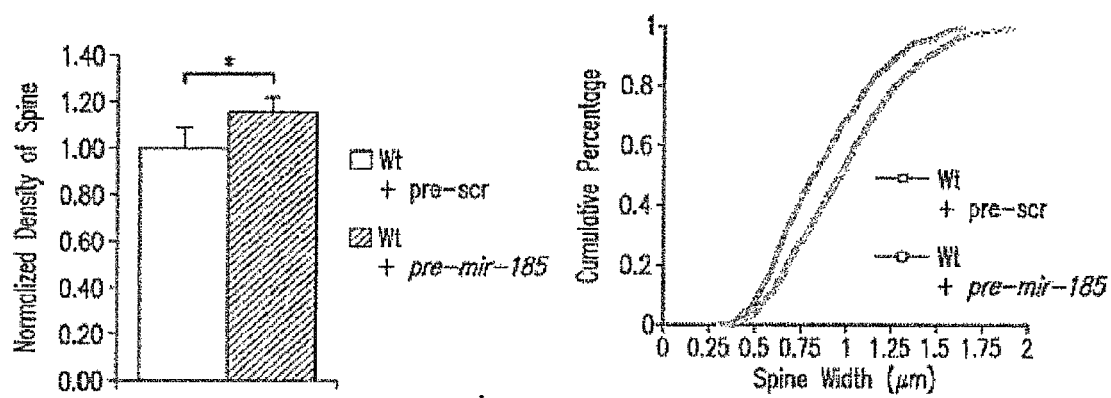
Figure 18E:
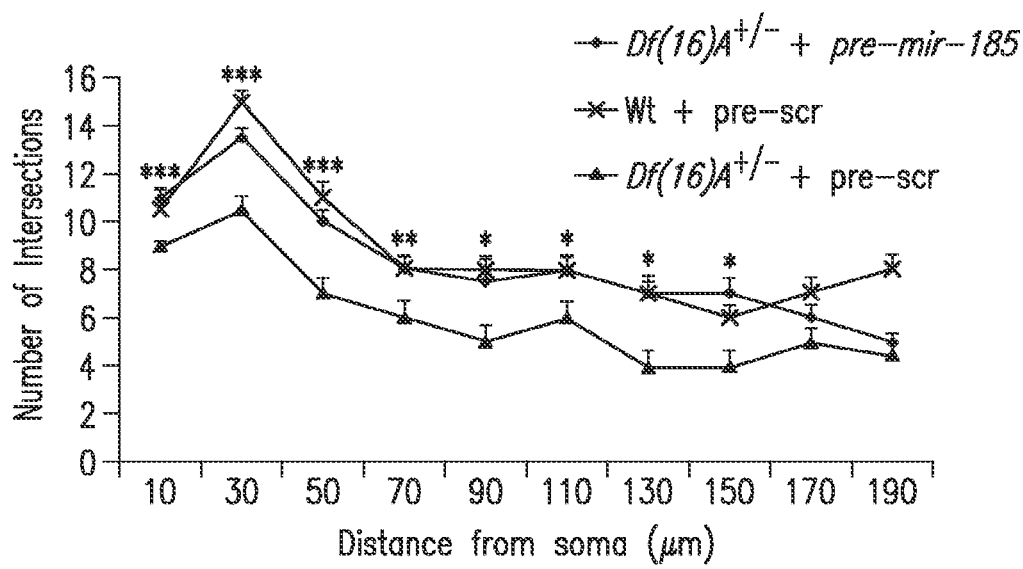
Figure 18F:
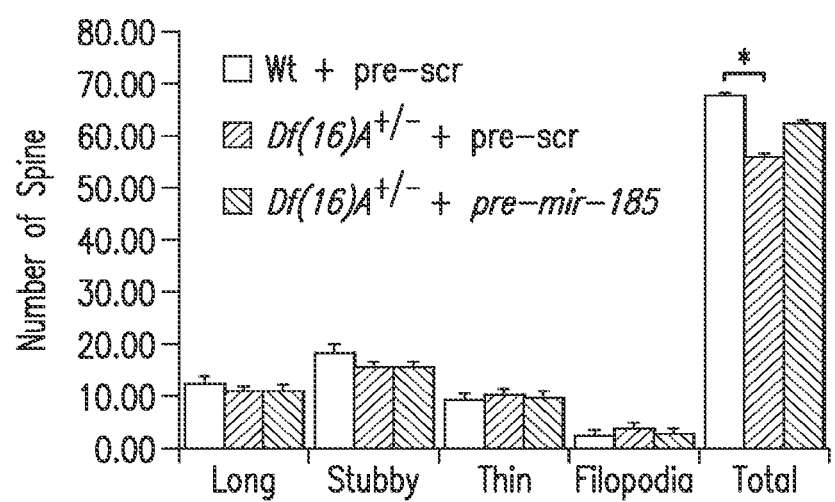
Figure 19A:
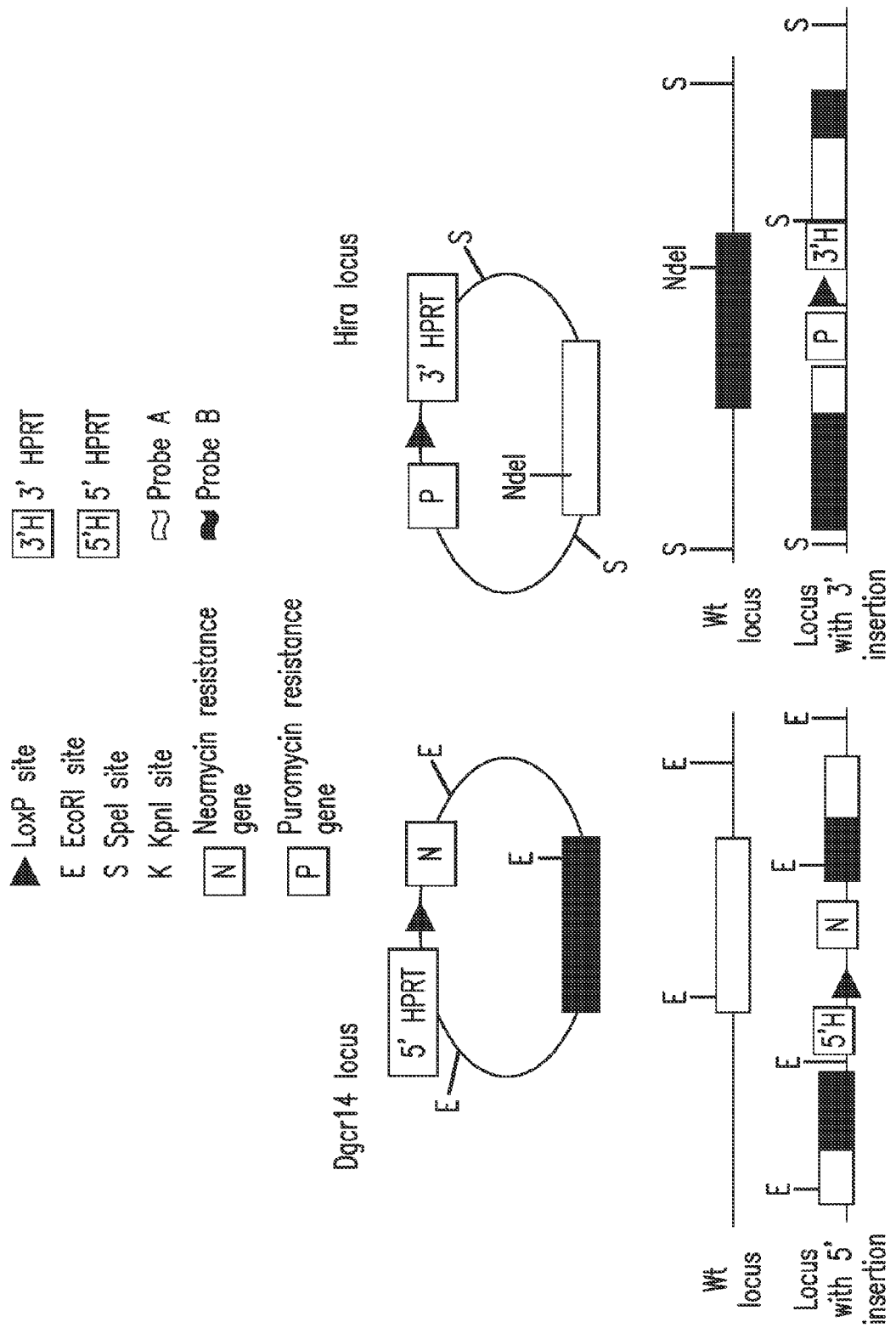
Figure 19B:
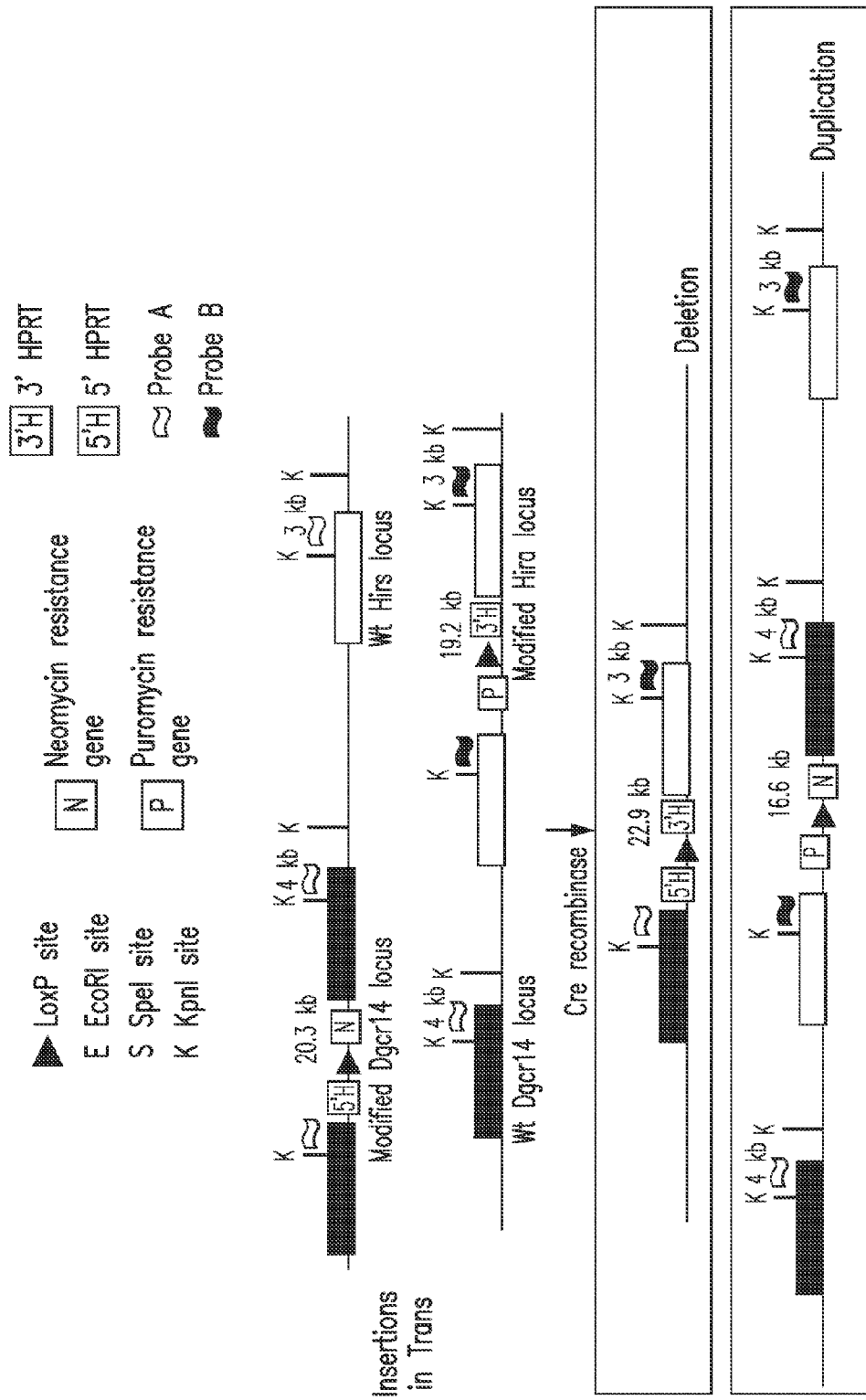
Figure 19C:
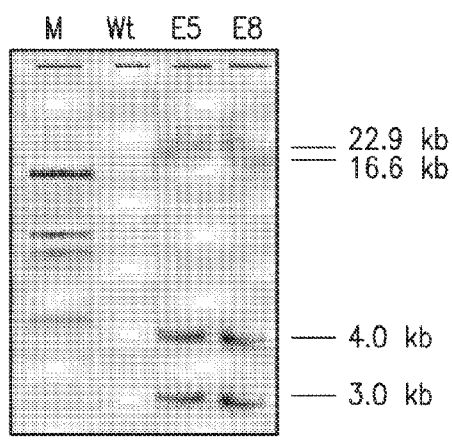
Figure 19D:
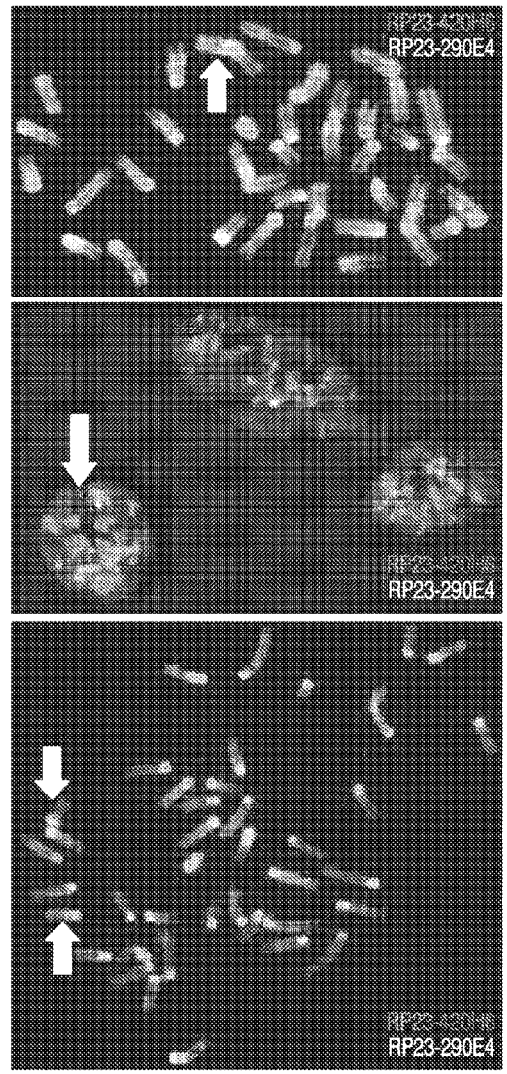

To investigate this, we first asked whether reduction of miR-185 levels results in deficits in dendritic and spine development similar to those observed in Df(16)A$^{+/-}$ neurons (9). We introduced an anti-miR-185 and a scramble control LNA oligonucleotide into Wt primary hippocampal neurons and measured dendritic and spine morphology two days post-transfection at DIV9 and DIV19, respectively. As mentioned above, we confirmed that introduction anti-miR-185 LNA oligo resulted in a significant increase of Mirta22 mRNA levels when compared to anti-miR control transfected primary neurons (FIG. 5C). Analysis of dendritic architecture indicated that reduction of miR-185 levels leads to deficits in dendritic complexity (FIG. 17A), including a significant reduction in the number of primary dendrites (21%, $P<0.05$; FIG. 17B) and a significant reduction in total branch points in transfected neurons (16%, $P<0.05$; FIG. 17C). This finding was confirmed by a Sholl analysis, which compares branch point numbers at varying distances from the soma (FIG. 18A). Moreover, reduction of miR-185 levels in DIV19 neurons results in decreased mushroom spine density (21%, $P<0.05$; FIGS. 17D and 17E and FIG. 18B) and a significant reduction in their median width (15% decrease, $P<0.001$, Kolmogorov-Smirnov test; FIG. 17F). These structural deficits recapitulate those observed in Df(16)A$^{+/-}$ neurons. Thus the neuronal deficits in Df(16)A$^{+/-}$ mice are, at least in part, due to the aberrantly low level of miR-185. Consistently, introduction pre-miR-185 mimic into Wt neurons increased the number of primary dendrites, the number of branch points, the density and head width of mushroom spines (FIGS. 18C and 18D).

Figure 3F:
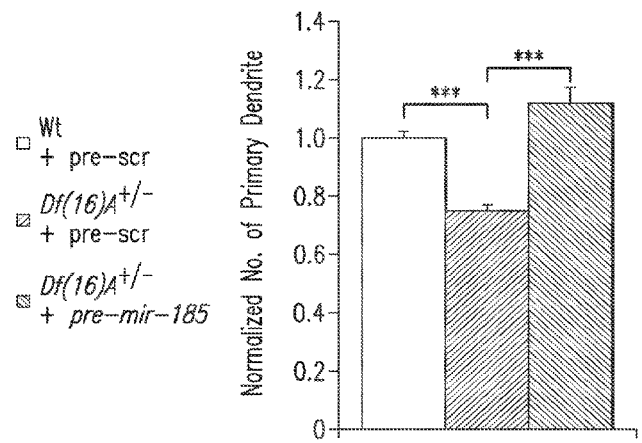
Figure 3G:
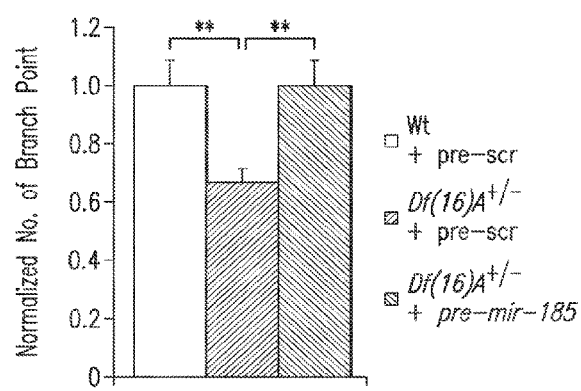
Figure 3H:
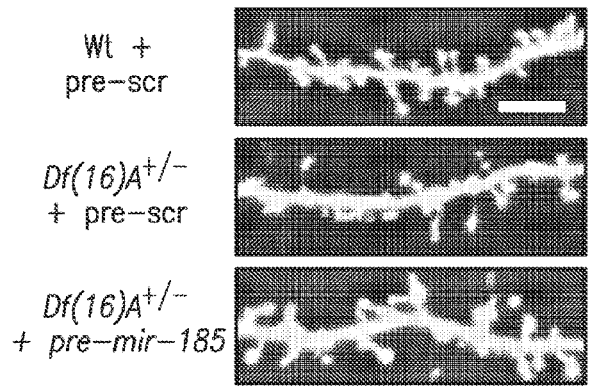
Figure 3I:
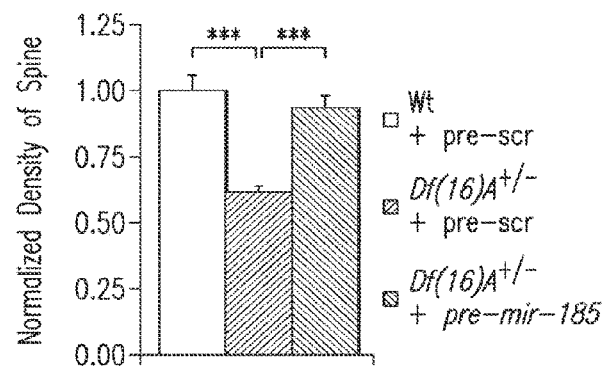
Figure 3J:
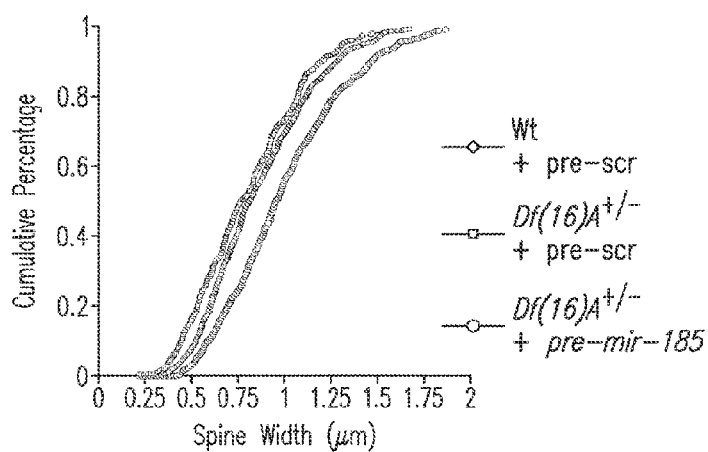

We also examined whether elevation of miR-185 levels could, at least partially, reverse cytoarchitectural alterations observed in Df(16)A$^{+/-}$ neurons (9). We transfected primary hippocampal neurons from Df(16)A$^{+/-}$ mice and their Wt littermates with a miRNA precursor mimic ("pre-miR-185," Ambion), which is processed into mature miRNA or a scramble precursor oligonucleotide ("pre-scramble") with no homology to the mouse genome, which serves as a control for nonspecific effects of small RNA expression. A co-transfected GFP reporter plasmid allowed us to analyze the dendritic architecture (FIG. 3E) and spine morphology (FIG. 3H) of GFP-positive pyramidal neurons at DIV9 (2 days following transfection) and DIV19 (2 days following transfection), respectively. In control experiments we confirmed that introduction of pre-miR-185 resulted in significant decrease in the levels of Mirta22 when compared to pre-scramble transfected neurons ($P<0.01$; FIG. 4B). Consistent with previous results, compared to WT neurons, Df(16)A$^{+/-}$ neurons transfected with pre-scramble showed reduced dendritic complexity as manifested by a decrease in the number of primary dendrites (25%, $P<10-10$; FIG. 3F) and the number of dendritic branchpoints (38%, $P<10-4$; FIG. 3G). They also showed reduced spine density (38%, $P<10^{-6}$, FIG. 3I) as well as a small, but statistically significant decrease in the head-width (8% in median width, P<0.01; FIG. 3J) of mushroom spines. Increase in mir-185 activity largely reversed the deficits in dendritic complexity (FIG. 3F, G, and FIG. 18E) and the reduction in spine density (FIG. 3I) and significantly increased the spine head-width of mushroom spines in Df(16)A$^{+/-}$ hippocampal neurons (18% increase in median width, P<0.001, Kolmogorov-Smirnov test; FIG. 3J). Thus, introduction of pre-mir-185 into hippocampal neurons from Df(16)A$^{+/-}$ mice reversed some key structural connectivity deficits.

A Primary Transcriptional Consequence of 22q11.2 Genomic Losses.

Figure 4A:
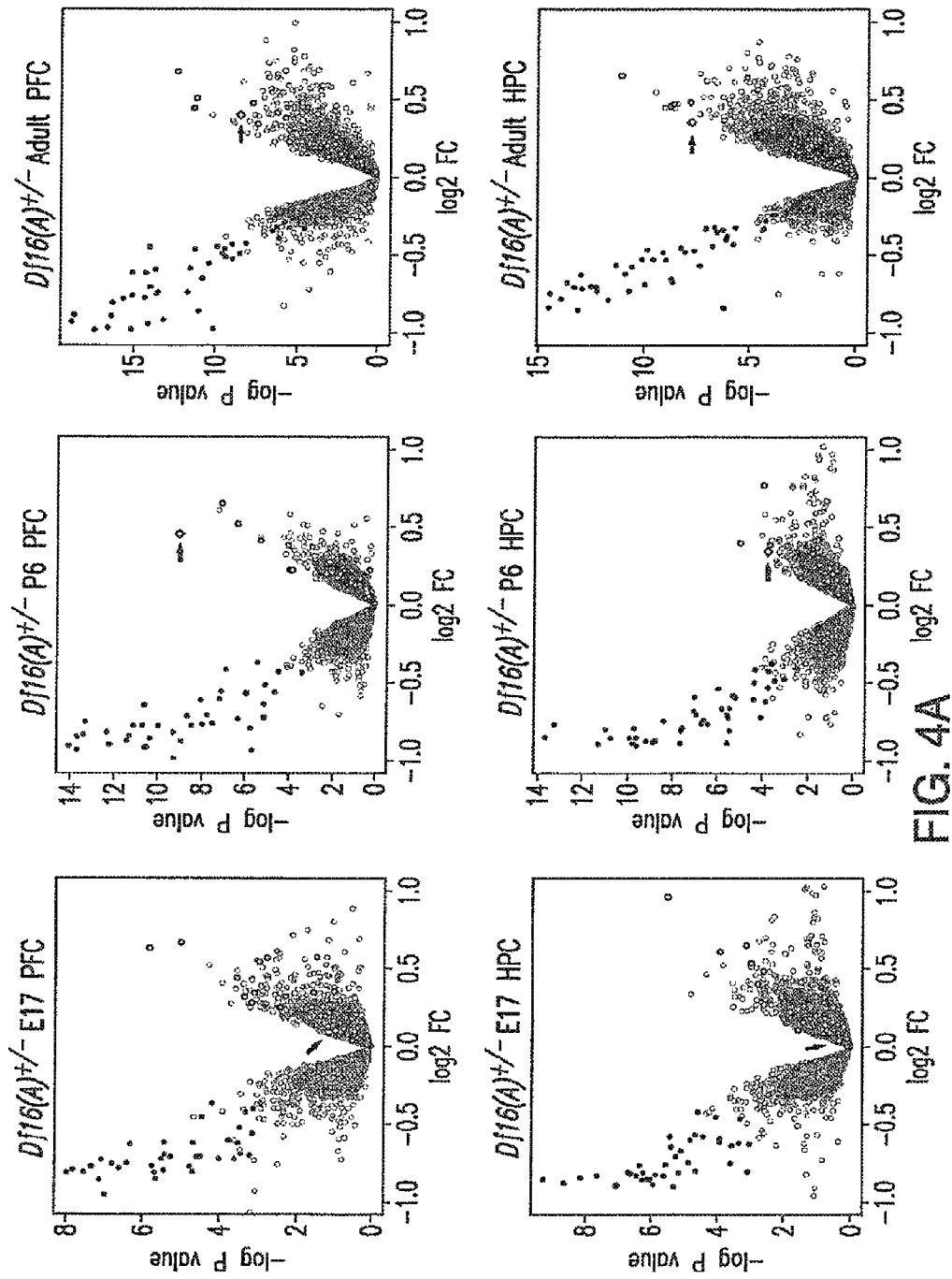

Impaired production of miRNAs may have considerable impact on target transcript stability. Previous microarray analysis of adult Df(16)A+/− mice revealed that reduction in dosage of genes in the 22q11.2 region results in genome-wide alterations of transcriptional programs in the HPC and PFC (8). We extended analysis of these two brain regions to two earlier developmental stages, embryonic day 17 (E17) and postnatal day 6 (P6), when mir-185 and possibly other miRNAs are already decreased in Df(16)A$^{+/-}$ mice. Only one gene, 2310044H10Rik, was consistently found to be significantly upregulated in at least two of the three developmental stages examined and in at least one of the two brain areas tested. Indeed, 2310044H10Rik was among the top upregulated genes in both postnatal stages examined (adult and P6) and the top upregulated transcript in the frontal cortex of P6 mutant mice (FIG. 4A, B). Notably, no significant difference in 2310044H10Rik expression was found in either frontal cortex or hippocampus at E17 (FIG. 4A, B).

In independent experiments, we attempted to distinguish primary versus secondary gene targets of the 22q11.2 microdeletion by looking for genes whose expression changes in opposite direction as a result of genomic losses or gains in this locus. Such genes are likely to represent primary targets and direct transcriptional readouts of the underlying copy number imbalances. By contrast, expression changes specific to genomic losses or in the same direction independently of genomic dosage are more likely to be secondary reflections of affected physiological process or malfunctioning brain regions (39). We compared the PFC and HPC gene expression profiles in mice carrying a deletion or duplication at the syntenic mouse locus using as reference compound heterozygous mice balanced for copy number (FIG. 19). We identified a number of inversely altered transcripts in either PFC or HPC (P-value<0.001, FIG. 27), in addition to the transcripts from the 22q11.2 region. The majority of the identified transcripts are pri-miRNA forms. Twelve transcripts were significantly misregulated in a reciprocal manner in both PFC and HPC (FIG. 20). Among them, 2310044H10Rik is the only gene with protein coding potential.

Figure 4C:
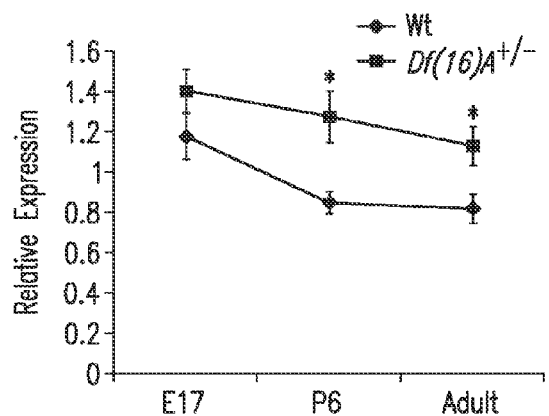
Figure 4D:
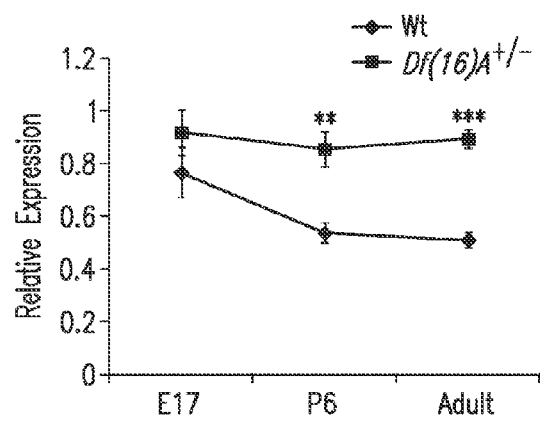
Figure 4E:
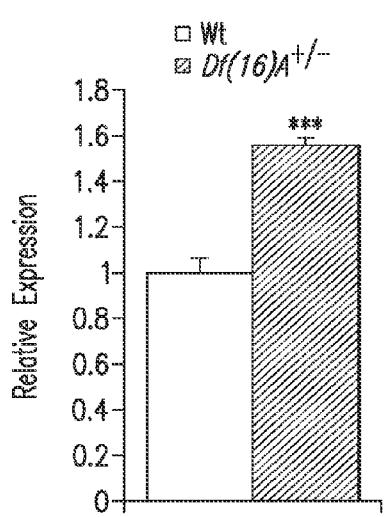

The pattern of upregulation in both PFC and HPC was confirmed by TaqMan qRT-PCR (PFC: E17, 20% P=0.24; P6, 59%, P<0.01; Adult, 76%, P<10$^{-6}$; HPC: E17, 20%, P=0.16; P6, 50%, P<0.05; Adult, 38%, P<0.05; FIG. 4C, D). This analysis revealed a profile of temporal regulation where levels of 2310044H10Rik rapidly decline during the first week after birth (between E17 and P6) and remain constantly low thereafter, as well as a corresponding pattern of expression misregulation in Df(16)A$^{+/-}$ mice where elevated expression of 2310044H10Rik persists throughout postnatal and adult life. Increased brain expression of 2310044H10Rik is recapitulated in primary hippocampal neurons from Df(16)A$^{+/-}$ mice (FIG. 4E). Importantly, there is not any known miRNA within or surrounding the 2310044H10Rik genomic locus suggesting that the observed upregulation is not due to impaired processing of overlapping pri-miRNA transcripts.

2310044H10Rik is major downstream effector of miRNA dysregulation. The gene expression profiling described above highlighted the impaired developmental regulation of 2310044H10Rik levels as a major consequence of the 22q11.2 deletion at the transcriptomic level. Notably, 2310044H10Rik mRNA levels were also elevated in Dgcr8$^{+/-}$ mice (HPC: 30%, P<0.05; PFC: 24%, P<0.05; FIG. 10), strongly suggesting that upregulation may be due to miRNA dysregulation. Indeed, two miRNA target site prediction programs, TargetScan (22) and mirDB (23), report that the 3"UTR of 2310044H10Rik contains binding sites of miRNAs shown both by microarray profiling (8) or qRT-PCR (FIG. 11) to be affected in Df(16)A$^{+/-}$ mice. Specifically, mirDB predicted 5 such miRNAs with binding sites in the 3'UTR of 2310044H10Rik including mir-185 and mir-485, whereas TargetScan predicted 13 miRNA sites, including sites for mir-185, mir-485, mir-491 and mir-224. Notably, both programs predicted that the 3'UTR of 2310044H10Rik contains sites for mir-185 and mir-485 (FIG. 5A).

Figure 5D:
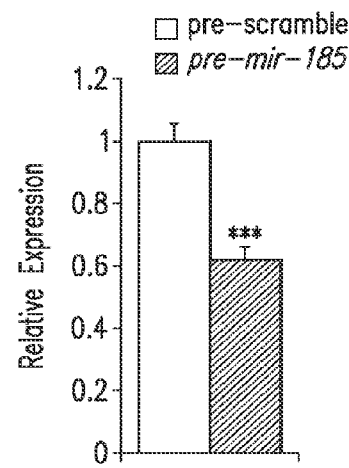
Figure 5E:
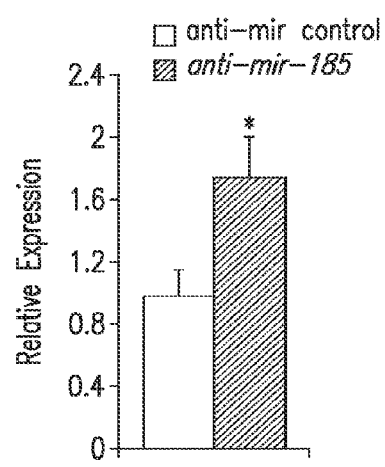

Because increased brain expression of 2310044H10Rik is recapitulated in primary neurons from Df(16)A$^{+/-}$ mice (FIG. 4E), we first used primary neurons to determine if endogenous 2310044H10Rik expression is actually under the control of miR-185. To examine the effect of miR-185 overexpression on 2310044H10Rik level, we introduced into primary neuronal cultures a miRNA precursor mimic ("pre-miR-185"), which is processed into mature miRNA, or a scramble precursor ("pre-scramble") with no homology to the mouse genome, which serves as a control for nonspecific effects of small RNA expression. 24 hours post-transfection, there was a 54% decrease in the levels of 2310044H10Rik in pre-mir-185 transfected neurons when compared to pre-scramble transfected neurons (P<0.01; FIG. 5B). In a complementary experiment, introduction of an anti-miR-185 LNA oligo or a scramble control oligo resulted in an increase of 2310044H10Rik mRNA levels in anti-miR-185 transfected cells when compared to scramble transfected cells (P<0.05; FIG. 5C). Taken together, these results confirm that 2310044H10Rik expression in primary neurons is under the repressive control of miR-185. Essentially identical results were obtained when 2310044H10Rik expression was assayed in N18 cells (FIGS. 5D and 5E).

Figure 5F:
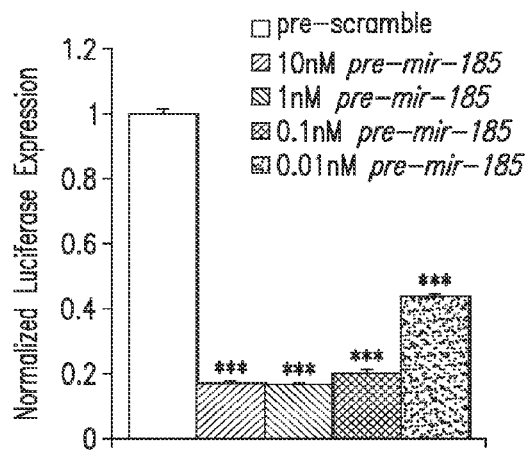

To further characterize the nature of the inhibition of mir-185 on 2310044H10Rik expression and test if it is 2310044H10Rik 3'UTR-dependent as predicted by TargetScan and mirDB (see above), 2310044H10Rik 3'UTR fused luciferase reporter genes (see Methods and Figure legend for details) were cotransfected with either "pre-mir-185" mimic or a scramble precursor ("pre-scramble"), into N18 cells, a mouse neuroblastoma cell line. Pre-scramble did not affect the reporter activity. Introduction of pre-mir-185 mimic led to a dramatic decrease of luciferase activity as compared to the pre-scramble control (P<0.001 for all pre-mir-185 concentrations used, compared to pre-scramble control; FIG. 5F). Repression by mir-185 occurs over a 10$^3$-fold range and more than 55% repression was still observed at a pre-mir-185 mimic concentration of 0.01 nM (FIG. 5F).

Figure 5G:
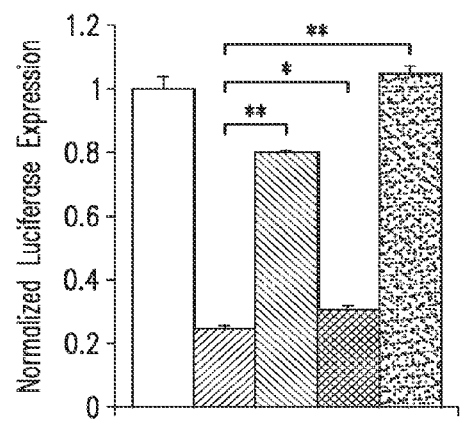
Figure 5H:
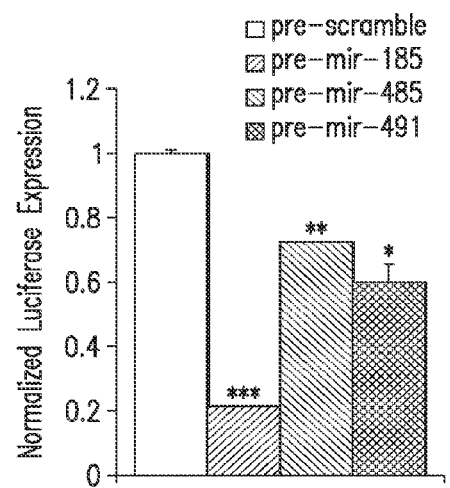

To investigate if mir-185-mediated repression is specific and operates directly via the two binding sites predicted by TargetScan (FIG. 5A), we engineered luciferase reporters carrying mutated versions of 2310044H10Rik 3'UTR with either individual or both mir-185 binding sites mutated (Mut1/Site 1 mutant; Mut2/Site 2 mutant; Mut1& 2/Site 1 and 2 mutants). The pre-mir-185 mimic significantly reduced the luciferase activity of the WT reporter to ~25% relative to a control reporter without 3'UTR, while it reduced the luciferase activities of the Mut1 and Mut2 reporters to 80% (P<0.01) and 33% (P<0.05) respectively, compared to WT 2310044H10Rik 3'UTR fused reporter (FIG. 5G). Notably, the pre-mir-185 mimic could not repress luciferase activity driven from a mutant reporter where both binding sites are simultaneously disrupted (FIG. 5G). Both mir-185 cognate binding sites have an impact on the 3'UTR-mediated regulation of Mirta22 expression, although the site disrupted in the Mut1 reporter (Site 1) seems to be the major target site via which mir-185 directly exerts its repressive effect.

We further addressed the dependence of 2310044H10Rik 3'UTR reporter repression on the levels of mir-485 or mir-491, which are also predicted to target binding sites in the 3'UTR of 2310044H10Rik gene. None of these miRNAs is located within the 22q11.2 microdeletion, but both are modestly down-regulated in HPC of Df(16)A$^{+/-}$ mice due to the Dgcr8 hemizygosity (FIG. 11). The pre-miRNA mimics of either miRNA modestly but significantly reduced the luciferase activity of the 3'UTR fused reporter compared to the pre-scramble control (pre-mir-485: 27%, P<0.05; pre-mir-491: 35%, P<0.05; FIG. 5G). A three factor ANOVA analysis indicated that all three miRNAs (miR-185, miR-485 and miR-491) and their interactions have significant impact on the luciferase activity with the exception of the interaction between miR-485 and miR-491 (FIG. 21). Taken together, these findings suggest that the persistent elevation of 2310044H10Rik levels observed in Df(16)A$^{+/-}$ mice is likely the result of the combined hemizygosity at mir-185 and Dgcr8 loci. Although more than one miRNA contributes, the major effect is due to the dramatic downregulation of mir-185. Consistent with this notion and the less profound reduction of mir-185 in Dgcr8$^{+/-}$ mice (FIG. 3D), 2310044H10Rik is only modestly upregulated in this strain (FIG. 10). Due to confirmed miRNA-mediated regulation, we renamed the gene Mirta22 (miRNA target of the 22q11.2 deletion).

Interestingly, a comparison between the 3'UTR of human and mouse Mirta22 orthologues as implemented by the "30-way multiz alignment and conservation analysis" in the USCS browser (FIG. 5A) reveals that mir-185 cognate Site 1, as well as one mir-485 binding site are located within a highly conserved region, suggesting that these sites may also play a critical role in regulating the levels of the human orthologue (C19orf63). Consistent with this expectation, introduction of pre-miR-185 into human 293T cells resulted in a significant decrease of endogenous C19orf63 levels (FIG. 22). In addition, similar to the pattern observed in the mouse brain, expression of C19orf63 decreases in infant brain (40). It is also noteworthy that, inspection of our gene expression database as well as qRT-PCR analysis of a sample of eight high-likelihood miR-185 targets identified by more than one prediction programs did not reveal any additional significant changes of transcript levels in the brains of Df(16)A$^{+/-}$ mice (FIG. 12). Furthermore, unlike 2310044H10Rik no other of the top upregulated protein coding genes (shown in FIG. 4B) are consistently altered in the both HPC and frontal cortex of E17, P6 and adult Df(16)A$^{+/-}$ mice and only one of them (B3gat1, see below) was predicted to contain miR-185 seed sites in its 3'UTR. Overall, although additional downstream targets of miR-185 may exist, especially at the level of translation, our analysis suggests that Mirta22 represents a major downstream effector of miR-185 and a major hub target of the miRNA dysregulation due to the 22q11.2 microdeletion.

Mirta22 Encodes a Novel Neuronal Protein Residing in the Golgi Apparatus.

Mirta22 encodes a 28 kD protein without any known sequence homology or functional domain. The murine orthologue is located on mouse chromosome 7 and contains seven coding exons. The human orthologue (C19orf63) is located on chromosome 19q13.33 and encodes a protein with 92.3% identity to the murine Mirta22 protein (FIG. 6A). One mouse reference sequence (isoform 1) is reported in GeneBank, while two C19orf63 isoforms (isoform 1 and 2) are reported in GeneBank and in the literature (24). The protein encoded by isoform 1 is predicted to contain an N-terminal signal peptide, as well as a putative transmembrane segment (FIG. 6A), which separates a long N-terminal region from a short C-terminal segment that contains a characteristic polyglycine tail with unknown function. Isoform 2 is generated by alternative splicing and differs from isoform 1 by an alternatively spliced exon located after exon 6. The protein encoded by isoform 2 is shorter by only 8 amino acids. contains the N-terminal signal peptide but not the transmembrane segment and it is predicted to be secreted (FIG. 6A).

Figure 6B:
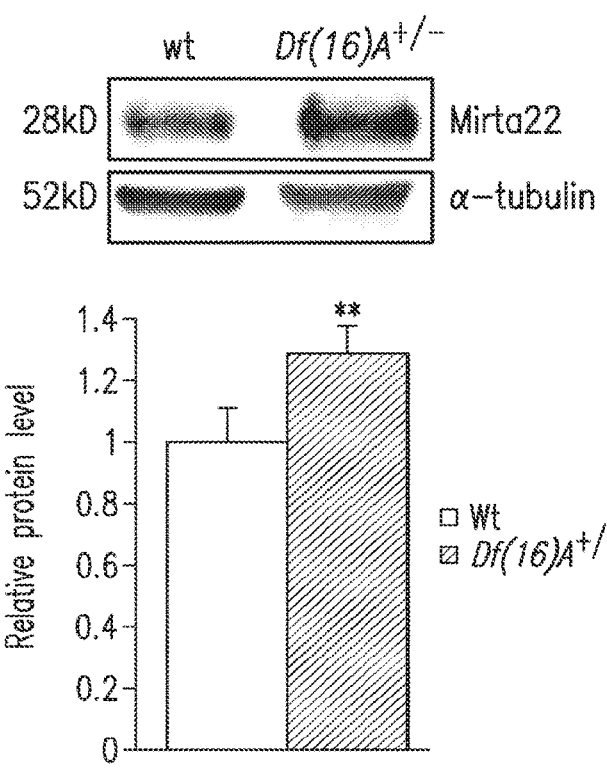
Figure 6C:
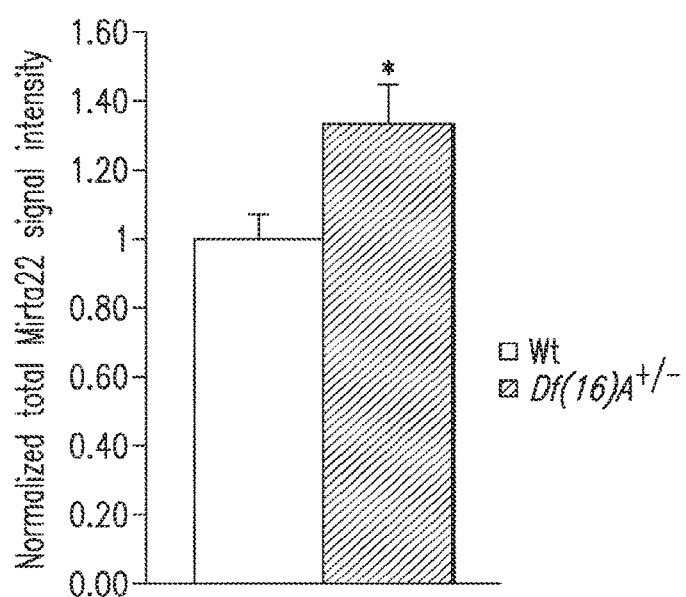
Figure 6D:
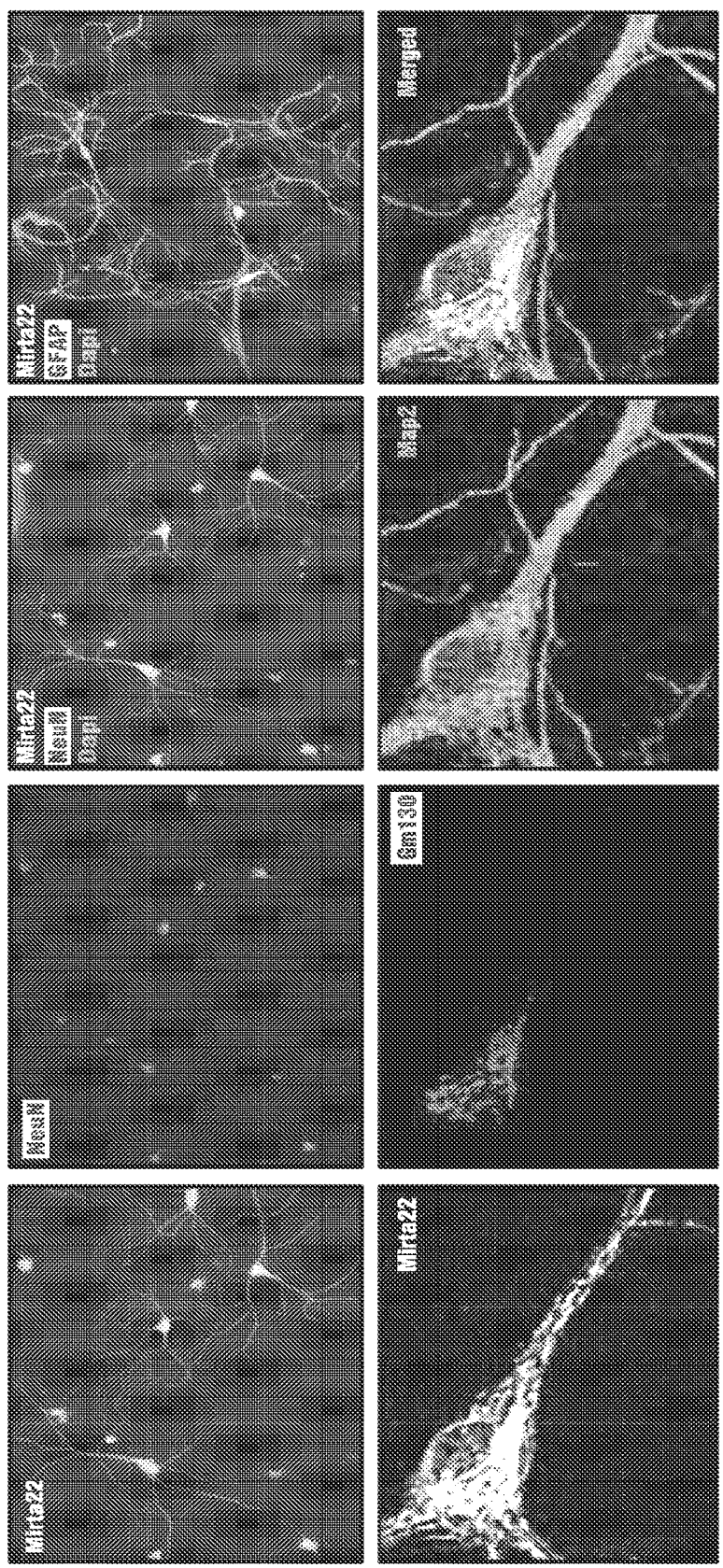
Figure 13C:
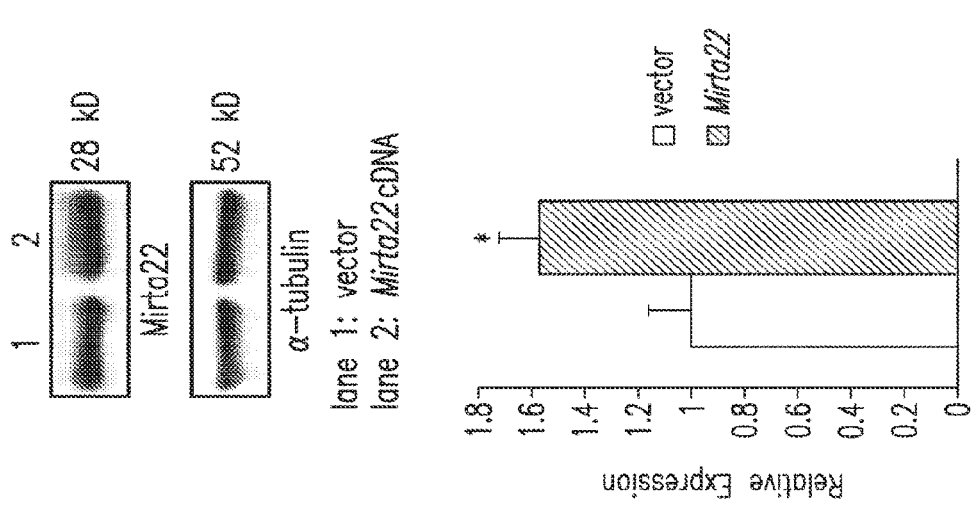
Figure 13E:
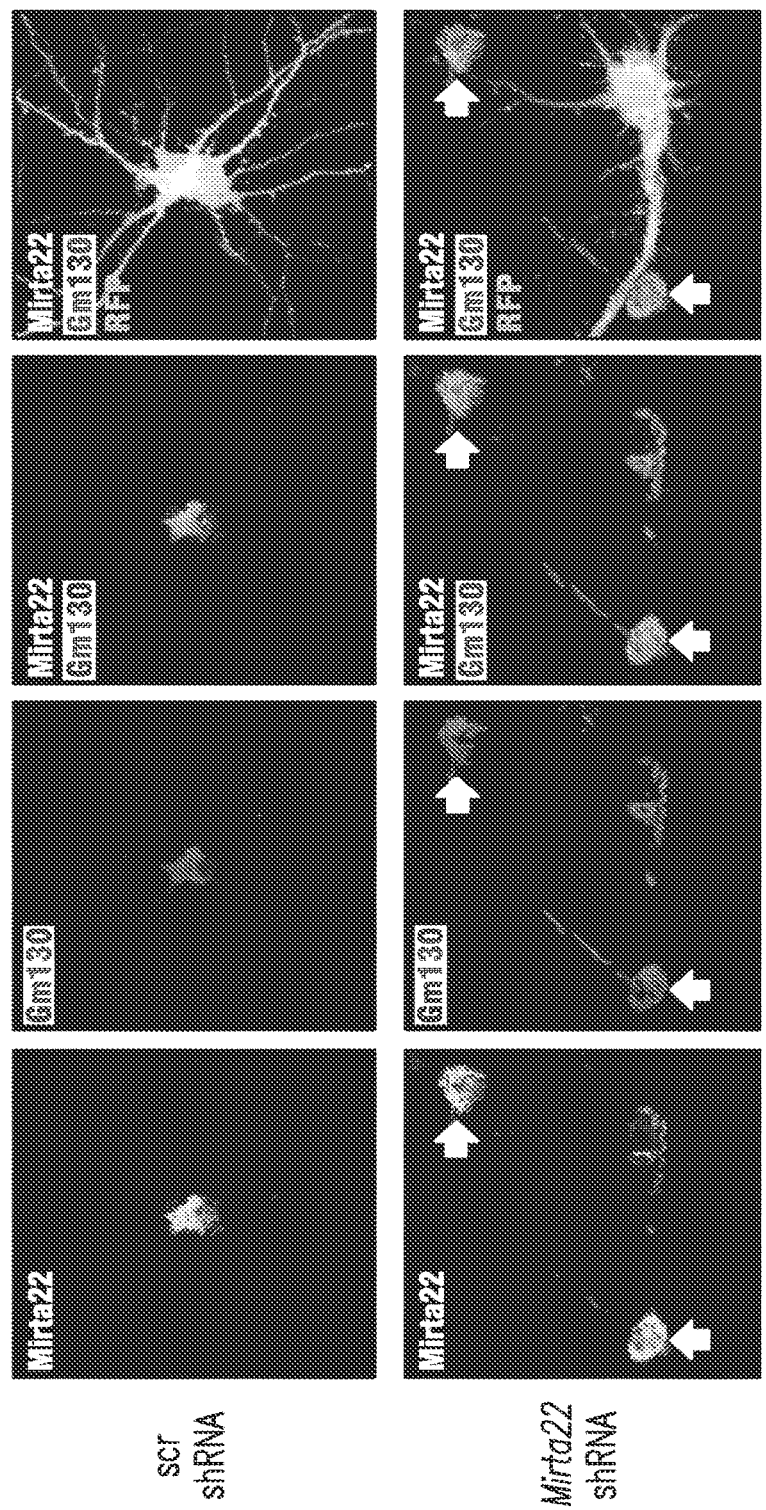
Figure 13F:
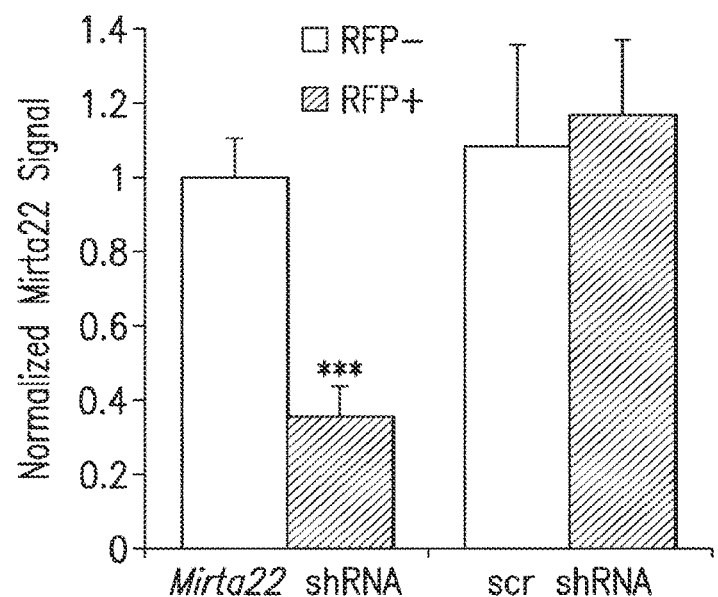
Figure 13G:
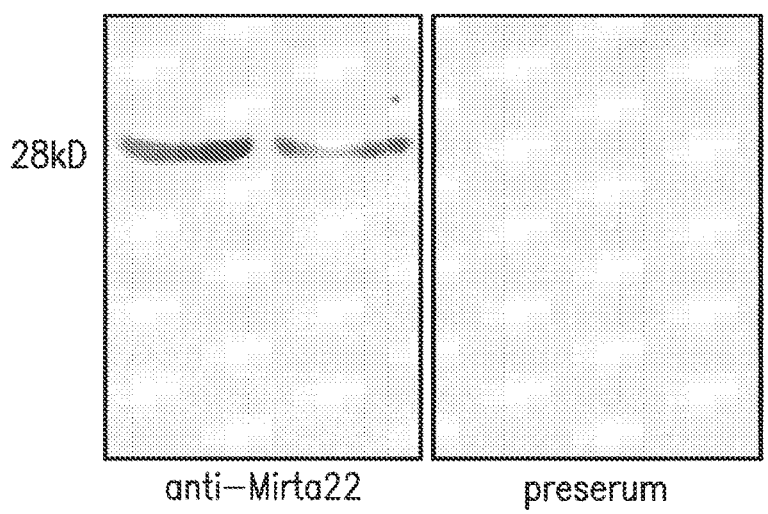

To investigate the distribution in the brain, as well as the subcellular localization of Mirta22, we raised a polyclonal antibody against a protein segment spanning both isoforms (amino acids 207-226, FIG. 6A; see Materials and Methods and FIGS. 13A, B and G for antibody generation and specificity). Immunohistochemical analysis demonstrated that Mirta22 is widely distributed in the brain (FIG. 14). The specificity of the antibody was validated by Western blot analysis on protein extracts from 293T cells transfected with a plasmid expressing full length Mirta22 cDNA with a C-terminal FLAG tag (FIG. 13A) or a mouse neuroblastoma cell line (N18), transfected with either a Mirta22 shRNA (FIG. 13B) or a lull length cDNA plasmid (FIG. 13C). Western blot assays of protein extracts from the brain or Df(16)A$^{+/-}$ mice and their Wt littermates showed the expected increase (25%) in the levels of Mirta22 in mutant mice (FIG. 6B). A similar in magnitude increase of the Mirta22 immunocytochemical signal was observed in Df(16)A$^{+/-}$ cultured neurons, as compared to Wt neurons (FIG. 6C). Analysis of cultured hippocampal neurons revealed that Mirta22 immunoreactivity is colocalized with neuron-specific marker NeuN, but not astrocyte-specific marker GFAP, indicating that Mirta22 is a neuronal protein (FIG. 6D, upper panel). Mirta22 immunoreactivity is found both in the soma, where it colocalizes with the Golgi apparatus marker GM13025, as well as in vesicle-like clusters and tubular-like clusters within the dendritic shafts (FIG. 6D, lower panel). Mirta22 immunoreactivity was not detected in cultures stained with preimmune serum (FIG. 13D) and was diminished by 64% in Mirta22 shRNA-transfected neurons (RFP+ neuron, FIG. 13E, lower panel).

miR-185 Reduction Results in Coordinated Mild Dysregulation of Golgi-Related Genes.

Accumulating evidence suggests that miRNAs may target functionally connected genes, often in a developmental stage-specific manner (41, 42). Consistent with this notion, functional annotation clustering analysis of 2708 predicted miR-185 targets (TargetScan Mouse v5.2) included in the DAVID Mus musculus gene functional annotation database identified as the top enriched gene cluster (gene count=159, Enrichment Score=8.56, FDR-corrected P=$2\times10^{-9}$) the Gene Ontology (cellular component) term "Golgi apparatus" (FIG. 23A). Gene set enrichment analysis (GSEA) on the 2708 predicted miR-185 targets ranked based on the gene expression profile of Df(16)A mice also indicated that the Gene Ontology terms "Golgi apparatus part" and "Golgi apparatus" were among the top 20 genesets in the adult HPC (FIG. 23A). A global perspective on the enrichment of this miR-185 target gene set among the differentially expressed genes in the Df(16)A$^{+/-}$ mice[29] showed a significant enrichment in the adult HPC expression profile (P=5×10$^{-4}$) where, as expected, most of top genes were upregulated (42 genes were upregulated and only 4 genes were downregulated at P<0.005, FIG. 23B and FIG. 28). A considerably more modest enrichment was suggested for the E17 (P=0.02) and P6 HPC (P=0.016) profiles (FIG. 24). Interestingly, there was no significant enrichment within the PFC profiles in all three ages tested (E17: P=0.6311; P6: P=0.1326; Adult: P=0.244). Expression changes were modest, with only 4 out of 159 Golgi-related probe sets included among the top 100 probe sets in the adult HPC. Overall, in addition to the robust and pervasive upregulation of Mirta22, reduction in miR-185 levels appears to affect expression of a group of Golgi apparatus-related genes in a milder, age and region-specific manner.

Elevation of Mirta22 Levels Inhibits Dendritic and Spine Development in Df(16)A$^{+/-}$ Neurons.

Figure 7A:
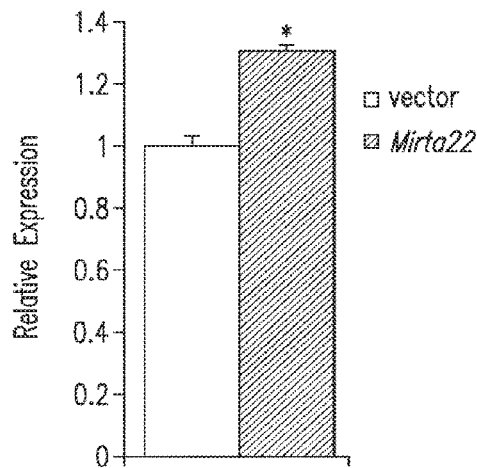
Figure 7B:
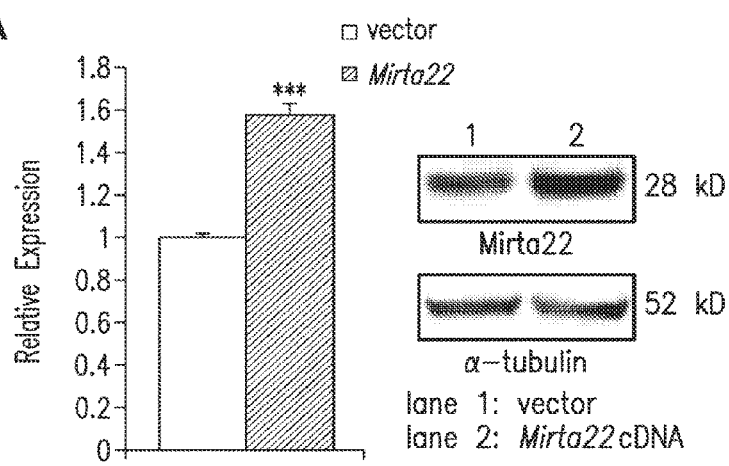
Figure 7C:
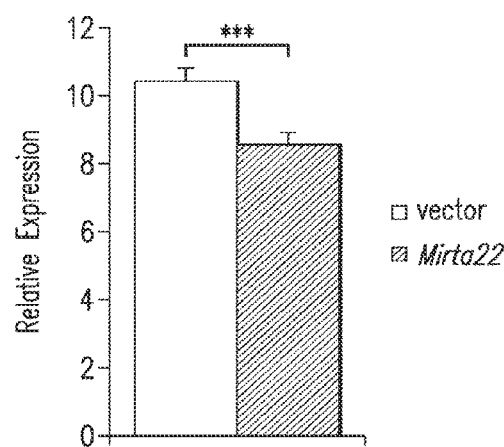
Figure 7D:
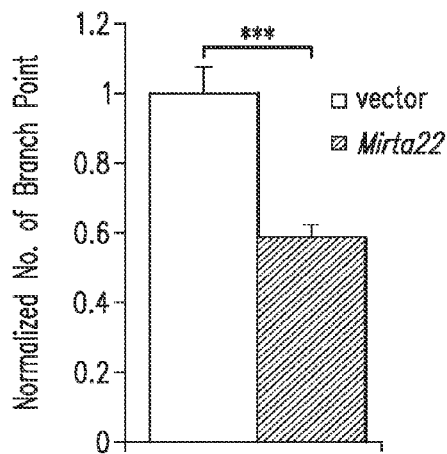
Figure 7E:
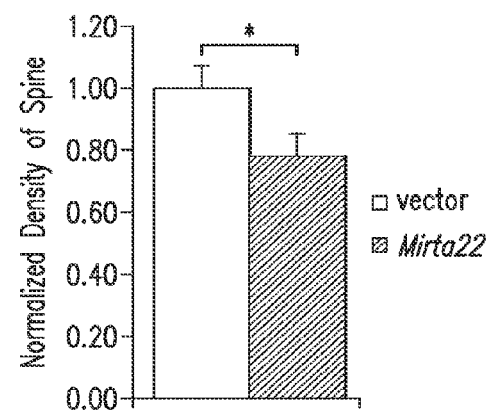
Figure 7F:
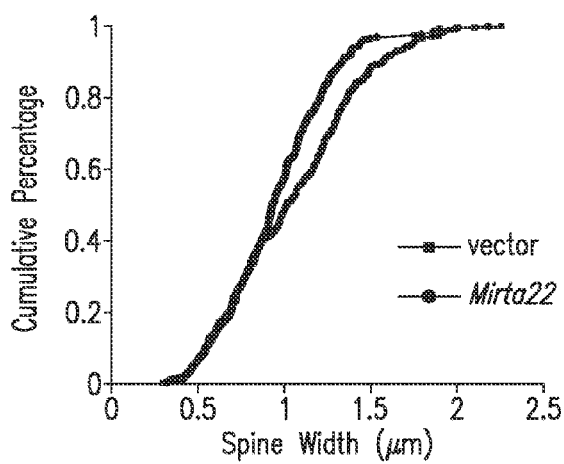
Figure 26A:
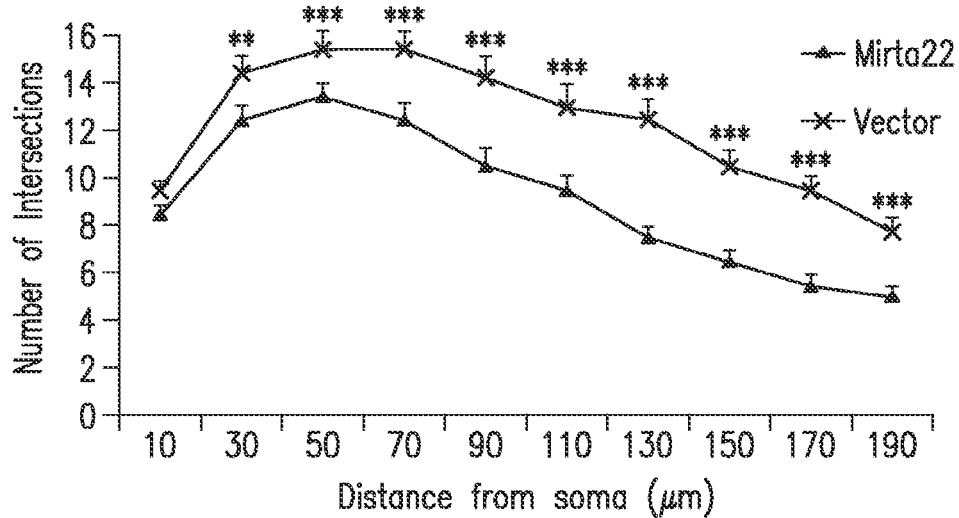

The observation that reduction of Mirta22 levels partially reverses the deficits in neuronal connectivity observed in Df(16)A$^{+/-}$ mice strongly suggests that Mirta22 may be an inhibitor of dendritic and spine development. To test this possibility and determine whether elevation of Mirta22 levels phenocopies aspects of the Df(16)A, we introduced a Mirta22 cDNA into WT primary hippocampal neurons and measured dendritic and spine morphology two days post-transfection at DIV9 and DIV19, respectively. Control experiments using qRT-PCR and western blot confirmed that the Mirta22-encoding plasmid drives increased expression of Mirta22 at both mRNA and protein levels (FIG. 7A, B). Analysis of dendritic architecture indicated that elevation of Mirta22 levels results in a significant reduction in the number of primary dendrites (18%, P<0.001; FIG. 7C) and total branch points in transfected neurons (41%, P<10$^{-5}$; FIG. 7D). This finding was confirmed by Sholl analysis (FIG. 26A). Moreover, elevation of Mirta22 levels in DIV19 neurons results in decreased spine density (22%, P<0.05; FIG. 7E) and a small but significant reduction in the mushroom spine width (8% decrease in median width, P<0.001, Kolmogorov-Smirnov test; FIG. 7F). These structural deficits recapitulate those observed in Df(16)A$^{+/-}$ neurons, suggesting the neuronal deficits in Df(16)A$^{+/-}$ mice are, at least in part, due to the aberrantly high level of Mirta22.

Figure 7G:
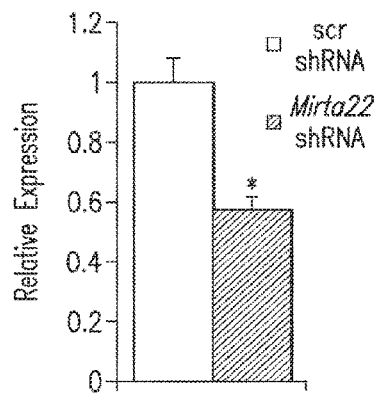
Figure 7H:
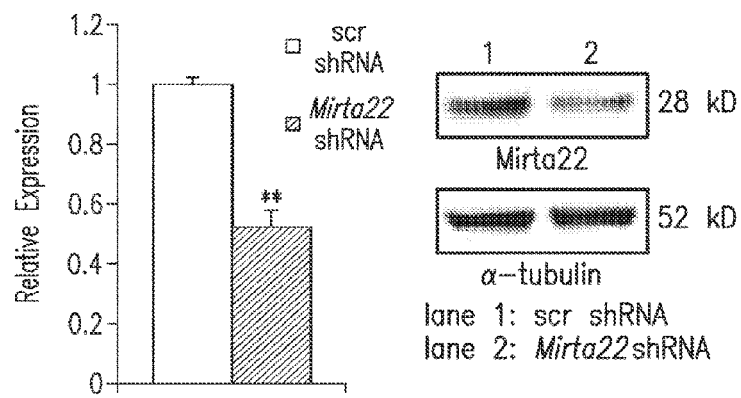
Figure 7I:
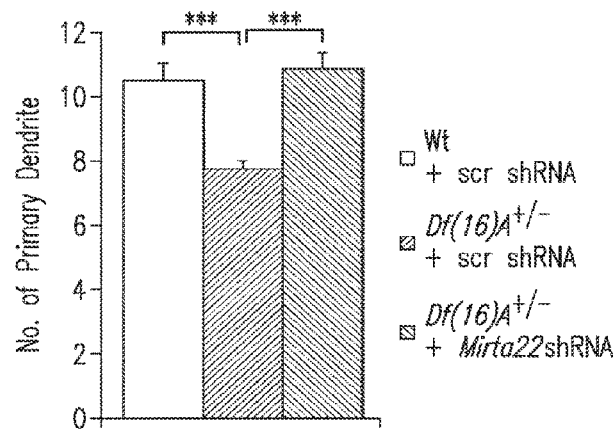
Figure 7J:
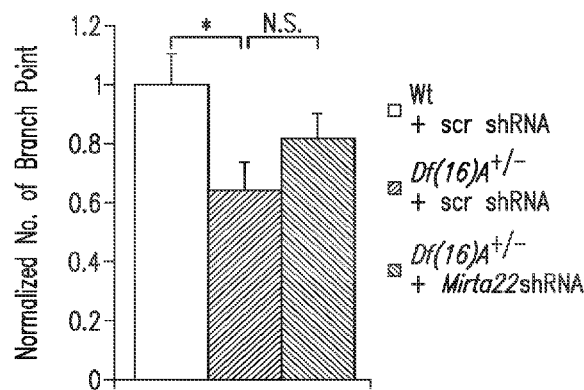
Figure 7K:
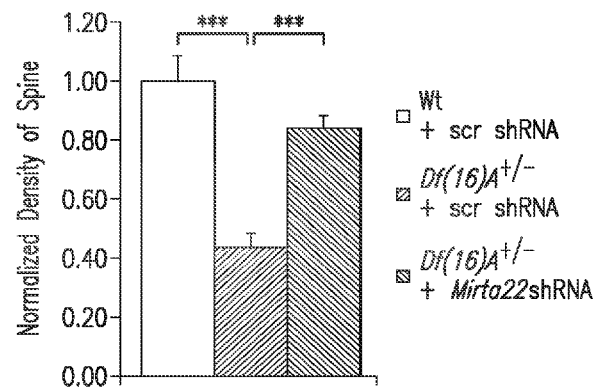
Figure 7L:
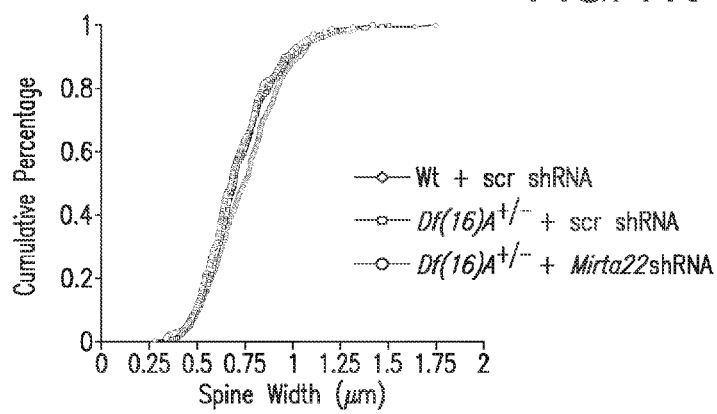
Figure 26B:
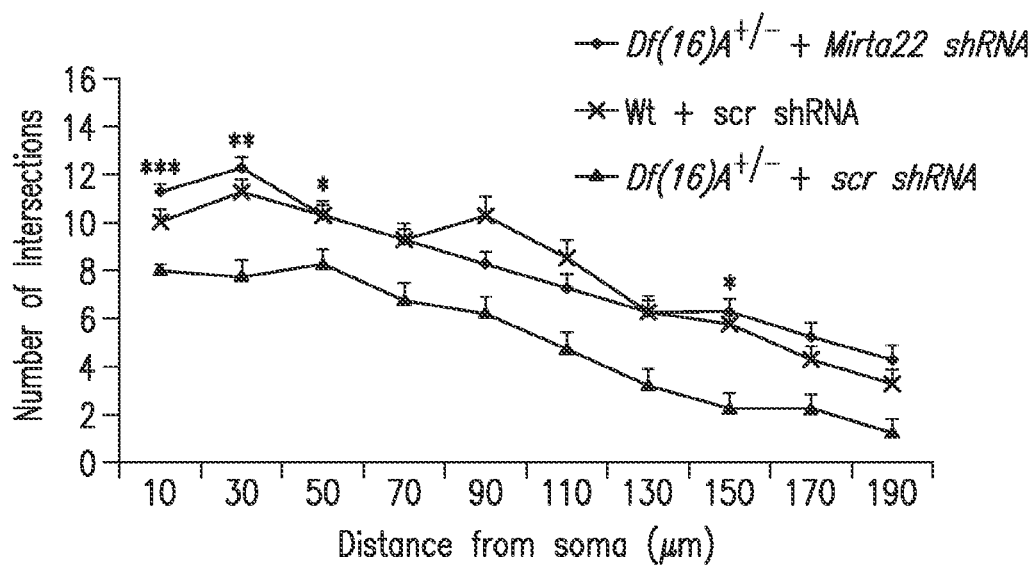
Figure 26C:
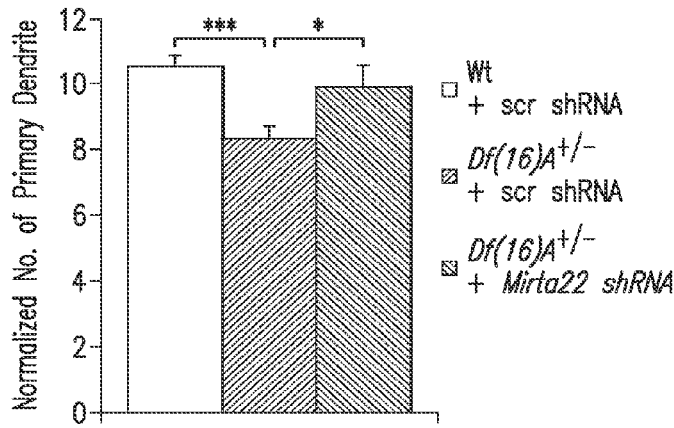
Figure 26D:
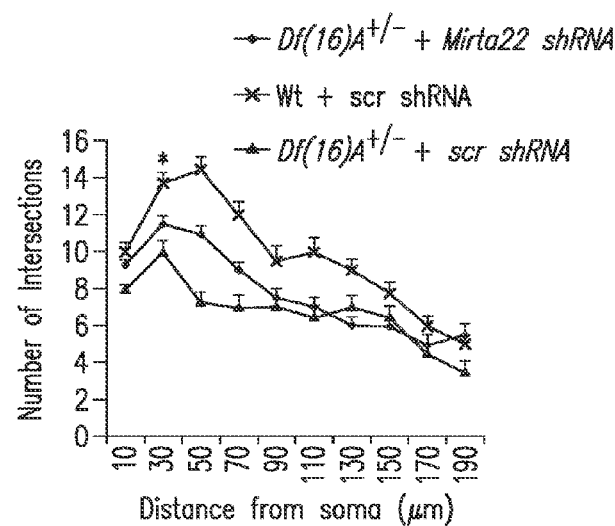
Figure 26E:
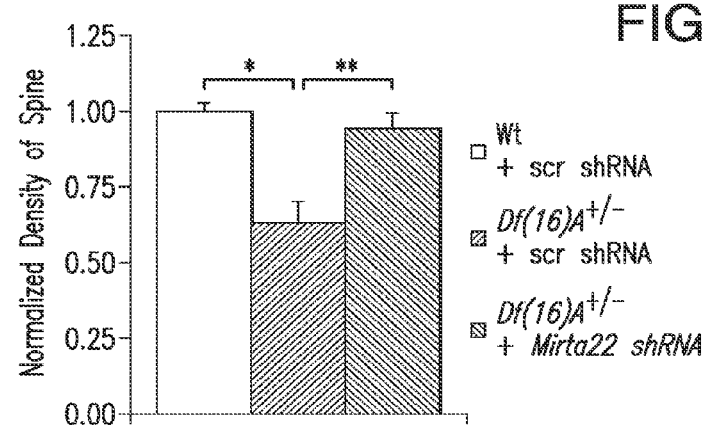

We showed that the elevation of mir-185 levels in primary hippocampal neurons from Df(16)A+/− mice reverses some key structural connectivity deficits that emerge as a result of the microdeletion. We also showed that Mirta22 is a major target of mir-185. Therefore, we considered the possibility that elevation of Mirta22 levels may contribute to at least some of the effects of the mir-185 deficiency on the neuronal morphology in Df(16)A$^{+/-}$ mice. To test this hypothesis, we asked first whether reduction of Mirta22 levels could partially reverse the neuronal abnormalities observed in Df(16)A$^{+/-}$ mice (9). We transfected primary hippocampal neurons isolated from Df(16)A$^{+/-}$ embryos and their WT littermates with constructs that coexpress turbo RFP (tRFP) and either a shRNA engineered to knock down expression of endogenous mouse Mirta22 or a scramble control shRNA (scr shRNA). We confirmed that the Mirta22 shRNAs can effectively knockdown the expression of Mirta22 at both mRNA and protein levels (FIGS. 7G, 7H and 15A). We analyzed dendritic architecture and spine morphology two days following transfection, at DIV9 and DIV19 respectively. Consistent with previous reports, we observed significantly reduced dendritic complexity in Df(16)A$^{+/-}$ neurons transfected with the control shRNA (FIG. 7I, J). Introduction of Mirta22 shRNA restored to WT levels the number of primary dendrites of Df(16)A$^{+/-}$ neurons at DIV9 (Mirta22 shRNA versus scr shRNA, 40% increase, P<10-5; FIG. 7I). An increase in the total number of branch points in Df(16)A$^{+/-}$ neurons was also observed but did not reach significance (25% increase, P=0.16; FIG. 7J). Sholl analysis confirmed that introduction of Mirta22 shRNA in Df(16)A$^{+/-}$ neurons increased branch point numbers mainly in the proximal dendritic segments from the soma (FIG. 26B). Furthermore, while DIV19 Df(16)A$^{+/-}$ neurons transfected with the control shRNA had fewer and thinner mushroom spines than WT neurons, introduction of Mirta22 shRNA into Df(16)A$^{+/-}$ neurons reversed the deficit in spine density (Mirta22 shRNA versus scr shRNA, 91% increase P<10$^{-6}$; FIG. 7K) while it had no impact on spine width (FIG. 7L). The observation that reduction of Mirta22 levels partially reverses the structural deficits observed in Df(16)A$^{+/-}$ mice was confirmed by using an independent Mirta22 shRNA (FIGS. 26C-E) and strongly suggests that Mirta22 acts as an inhibitor mediating the effects of the structural mutation of dendritic and spine growth.

6.3 Discussion

Elucidation of the biological processes affected by pathogenic CNVs may offer novel insights into the pathogenesis of psychiatric disorders as well as disorders of cognitive development (2). However, the transcriptional networks and signaling cascades that mediate the effects of CNVs on neuronal structure and function remain to a large extent uncharacterized. This study was designed to identify such downstream targets and processes disrupted by a bona fide pathogenic mutation that predisposes to schizophrenia and cognitive dysfunction. By applying an array of morphological, molecular and cellular assays to a mouse model of this mutation we provide a number of novel mechanistic insights.

First, taken together with previous results on the effects of Dgcr8 hemizygosity (18, 8) we provide a comprehensive view of the pattern of miRNA dysregulation emerging due to 22q11.2 deletions, which is shaped by the combined (synergistic and additive) effect of miR-185 and Dgcr8 hemizygosity (see graphic summary). In this context, our results shows how a genuine gene X gene interaction within a pathogenic CNV can result in a considerably greater reduction of the expression of a resident gene than expected by the 50% decrease in gene dosage indicating that mechanisms other than simple haploinsufficiency could represent an important and previously unappreciated component of CNV pathogenicity. Along these lines, our results also raise the more general and intriguing possibility that 22q11.2 microdeletions, by partially disabling the miRNA machinery, create a sensitized genetic background, which promotes the effects of deleterious mutations that affect the expression or activity of a subset of miRNAs (43, 44).

Second, by comparing gene expression profiles over three developmental stages and variable levels of genomic dosage at the 22q11.2 locus we identified elevated levels of a previously uncharacterized gene, Mirta22 as the most robust change in gene expression resulting from the 22q11.2 microdeletion, as well as the major downstream transcriptional effects of the 22q11.2-associated miRNA dysregulation.

Third, using physiologically relevant cellular models we provide unequivocal evidence that Mirta22 as well as its primary miRNA regulator (miR-185) mediate, at least in part, the effects of the 22q11.2 microdeletions on dendrite and spine formation. Although results from acute manipulations of gene expression via transient transfections of primary neurons cannot be over-interpreted quantitatively, the observed convergence and remarkable consistency of data from a multitude of experimental manipulations and approaches convincingly identified Mirta22 as a miRNA-regulated inhibitory factor of neuronal maturation that does not belong to any previously described class of developmental modulators.

Localization of Mirta22 in the Golgi apparatus and in vesicle and tubular-like extensions in dendrites is consistent with a role in membrane and protein trafficking and secretion, which is necessary for establishment and maintenance of neuronal connections (28). Mirta22 is likely to act in concert with other genes within the 22q11.2 deletion (2), including the Zdhhc8 palmitoyl-transferase, which is also located in the Golgi apparatus and has been shown to modulate dendritic and spine development (9). A potential interaction between miRNA dysregulation and altered neuronal palmitoylation is supported by previous findings (45, 21) and contributions from more than one gene to the morphological phenotypes described in this study are consistent with an oligogenic basis for the psychiatric and cognitive symptoms associated with 22q11.2 microdeletions (2). Moreover, although Mirta22 represents a major downstream effector of miR-185 dysregulation, our finding of a coordinated miR-185 targeting of Golgi apparatus-related genes suggests that Mirta22 upregulation may act, in an age and brain region specific manner, in concert with other modestly altered miR-185 targets to interfere with the Golgi-related processes required for neuronal maturation. Thus, our findings highlight a link between the Gogli apparatus and neuronal phenotypes associated with 22q11.2 micodeletions.

The reduction in the levels of Mirta22 soon after birth during periods of active neuronal maturation and synaptogenesis suggests that repression of this gene may play an important role in promoting neural circuit formation, especially in the postnatal brain, after embryonically generated neurons have migrated to their final destinations. Consistent with the notion that miRNAs function predominantly as fine-tuning regulators of the expression levels of their targets (26, 27), miR-185 and to a lesser extent other miRNAs affected by the 22q11.2 deletion appear to restrict and optimize Mirta22 expression, presumably to avoid excessive inhibition during this critical stage of synapse formation. Accordingly, sustained derepression of the gene due to genomic loss at the 22q11.2 locus may have an impact on the formation of neural circuits in early development, as well on their maintenance during adulthood. Such structural changes may result in local and long-distance disruptions of neuronal communication that may contribute to the cognitive dysfunction, psychiatric phenotypes or both (18, 46). In agreement with this prediction expression of the human orthologue of Mirta22 (C19orf63) declines in infant brains (40) and displays a spatio-temporal pattern that significantly overlaps with the one of Neuroligin-3, consistent with participation in processes related to synapse and circuit formation and maturation (47). Moreover, it has been shown that during the transition between human fetal and early postnatal development a large number of the genes reverse their direction of expression from an increase in utero to a decrease in the months after birth and that ~40% of them are predicted miRNA targets (40). In that respect, Mirta22 is one of the first examples of a disease-related gene representative of this prominent type of transcriptional trajectory indicative of a miRNA-imposed inhibitory control over postnatal brain development.

Accumulating evidence suggests that miRNAs play an important role in the pathogenesis and pathophysiology of psychiatric disorders and cognitive dysfunction (29,14). Our work represents one of the first examples where a major downstream target of a disease-related miRNA dysregulation has been unequivocally identified and its function has been characterized. It will be of interest to determine whether elevation in Mirta22 levels affect additional aspects of neuronal structure and function. Future studies, entailing normalization of Mirta22 levels in mice compound heterozygous for Df(16)A and Mirta22 loss of function alleles should also establish which of the various behavioral (8), cognitive (48, 8) and circuit alterations (18, 46) observed in Df(16)A$^{+/-}$ mice can be attributed to the inhibitory influence of Mirta22 upregulation. In addition, since inhibition of Mirta22 function is predicted to promote formation of neuronal connections in the 22q11.2 deletion carriers, drugs that target this molecule may be used to ameliorate associated cognitive and psychiatric phenotypes.

7. REFERENCES

1 Karayiorgou, M. et al. Schizophrenia susceptibility associated with interstitial deletions of chromosome 22q11. Proceedings of the National Academy of Sciences of the United States of America 92, 7612-7616, (1995).

2 Karayiorgou, M., Simon, T. J. & Gogos, J. A. 22q11.2 microdeletions: linking DNA structural variation to brain dysfunction and schizophrenia. Nat Rev Neurosci 11, 402-416, (2010).

3 Stefansson, H. et al. Large recurrent microdeletions associated with schizophrenia. Nature 455, 232-236, (2008).

4 ISC. Rare chromosomal deletions and duplications increase risk of schizophrenia. Nature 455, 237-241, (2008).

5. Xu, B. et al. Strong association of de novo copy number mutations with sporadic schizophrenia. Nat Genet 40, 880-885, (2008).

6 Arguello, P. A. & Gogos, J. A. Modeling madness in mice: one piece at a time. Neuron 52, 179-196, (2006).

7 Arguello, P. A. & Gogos, J. A. Cognition in mouse models of schizophrenia susceptibility genes. Schizophr Bull 36, 289-300, (2010).

8 Stark, K. L. et al. Altered brain microRNA biogenesis contributes to phenotypic deficits in a 22q11-deletion mouse model. Nat Genet 40, 751-760, (2008).

9 Mukai, J. et al. Palmitoylation-dependent neurodevelopmental deficits in a mouse model of 22q11 microdeletion. Nat Neurosci 11, 1302-1310, (2008).

10. Chow, E. W., Zipursky, R. B., Mikulis, D. J. & Bassett, A. S. Structural brain abnormalities in patients with schizophrenia and 22q11 deletion syndrome. Biol Psychiatry 51, 208-215, (2002).

11 Yuste, R. & Tank, D. W. Dendritic integration in mammalian neurons, a century after Cajal. Neuron 16, 701-716, (1996).

12 Mainen, Z. F. & Sejnowski, T. J. Influence of dendritic structure on firing pattern in model neocortical neurons. Nature 382, 363-366, (1996).

13 Kosik, K. S. The neuronal microRNA system. Nat Rev Neurosci 7, 911-920, (2006).

14 Xu, B., Karayiorgou, M. & Gogos, J. A. MicroRNAs in psychiatric and neurodevelopmental disorders. Brain Res 1338, 78-88, (2010).

15 Schratt, G. microRNAs at the synapse. Nat Rev Neurosci 10, 842-849, (2009).

16 Fineberg, S. K., Kosik, K. S. & Davidson, B. L. MicroRNAs potentiate neural development. Neuron 64, 303-309, (2009).

17 Tomari, Y. & Zamore, P. D. Perspective: machines for RNAi. Genes & development 19, 517-529, (2005).

18 Fenelon, K. et al. Deficiency of Dgcr8, a gene disrupted by the 22q11.2 microdeletion, results in altered short-term plasticity in the prefrontal cortex. Proceedings of the National Academy of Sciences of the United States of America 108, 4447-4452, (2011).

19 Fiore, R. et al. Mef2-mediated transcription of the miR379-410 cluster regulates activity-dependent dendritogenesis by fine-tuning Pumilio2 protein levels. EMBO J 28, 697-710, (2009).

20 Schratt, G. M. et al. A brain-specific microRNA regulates dendritic spine development. Nature 439, 283-289, (2006).

21 Siegel, G. et al. A functional screen implicates microRNA-138-dependent regulation of the depalmitoylation enzyme APT1 in dendritic spine morphogenesis. Nat Cell Biol 11, 705-716, (2009).

22 Grimson, A. et al. MicroRNA targeting specificity in mammals: determinants beyond seed pairing. Molecular cell 27, 91-105, (2007).

23 Wang, X. miRDB: a microRNA target prediction and functional annotation database with a wiki interface. RNA (New York, N.Y. 14, 1012-1017, (2008).

24 Junes-Gill, K. S. et al. hHSS1: a novel secreted factor and suppressor of glioma growth located at chromosome 19q13.33. J Neurooncol 102, 197-211, (2011).

25 Nakamura, N. et al. Characterization of a cis-Golgi matrix protein, GM130. J Cell Biol 131, 1715-1726, (1995).

26 Baek, D. et al. The impact of microRNAs on protein output. Nature 455, 64-71, (2008).

27 Selbach, M. et al. Widespread changes in protein synthesis induced by microRNAs. Nature 455, 58-63, (2008).

28 Horton, A. C. et al. Polarized secretory trafficking directs cargo for asymmetric dendrite growth and morphogenesis. Neuron 48, 757-771, (2005).

29 Moreau, M. P., Bruse, S. E., David-Rus, R., Buyske, S. & Brzustowicz, L. M. Altered microRNA expression profiles in postmortem brain samples from individuals with schizophrenia and bipolar disorder. Biol Psychiatry 69, 188-193, (2011).

30. Rodriguez, A., Ehlenberger, D. B., Dickstein, D. L., H of, P. R. & Wearne, S. L. Automated three-dimensional detection and shape classification of dendritic spines from fluorescence microscopy images. PLoS ONE 3, e1997, (2008).

31 Wearne, S. L. et al. New techniques for imaging, digitization and analysis of three-dimensional neural morphology on multiple scales. Neuroscience 136, 661-680, (2005).

32 Scorcioni, R., Polavaram, S, & Ascoli, G. A. L-Measure: a web-accessible tool for the analysis, comparison and search of digital reconstructions of neuronal morphologies. Nat Protoc 3, 866-876, (2008).

33 Nuovo, G. J. et al. A methodology for the combined in situ analyses of the precursor and mature forms of microRNAs and correlation with their putative targets. Nat Protoc 4, 107-115, (2009).

34 Jiang, M. & Chen, G. High Ca2+-phosphate transfection efficiency in low-density neuronal cultures. Nat Protoc 1, 695-700, (2006), 35 Benjamini, Y. & Hochberg, Y. CONTROLLING THE FALSE DISCOVERY RATE—A PRACTICAL AND POWERFUL APPROACH TO MULTIPLE TESTING. J. R. Stat. Soc. Ser. B-Methodol. 57, 289-300, (1995).

36 Rehmsmeier, M., Steffen, P., Hochsmann, M. & Giegerich, R. Fast and effective prediction of microRNA/target duplexes. RNA (New York, N.Y. 10, 1507-1517, (2004).

37 Schneider Gasser, E. M. et al. Immunofluorescence in brain sections: simultaneous detection of presynaptic and postsynaptic proteins in identified neurons. Nat Protoc 1, 1887-1897, (2006).

38 Lee, H. K., Braynen, W., Keshav, K., and Pavlidis, P. (2005). ErmineJ: tool for functional analysis of gene expression data sets. BMC Bioinformatics 6, 269.

39 Chahrour, M., Jung, S. Y., Shaw, C, Zhou, X., Wong, S. T., Qin, J., and Zoghbi, H. Y. (2008). MeCP2, a key contributor to neurological disease, activates and represses transcription. Science 320, 1224-1229.

40 Colantuoni, C, Lipska, B. K., Ye, T., Hyde, T. M., Tao, R., Leek, J. T., Colantuoni, E. A., Elkahloun, A. G., Herman, M. M., Weinberger, D. R., et al. (2011). Temporal dynamics and genetic control of transcription in the human prefrontal cortex. Nature 478, 519-523.

41 Tsang, J. S., Ebert, M. S., and van Oudenaarden, A. (2010). Genome-wide dissection of microRNA functions and cotargeting networks using gene set signatures. Mol Cell 38, 140-153.

42 Zhang, L., Hammell, M., Kudlow, B. A., Ambros, V., and Han, M. (2009). Systematic analysis of dynamic miRNA-target interactions during *C. elegans* development. Development 136, 3043-3055.

43 Ambros, V. (2010). MicroRNAs: genetically sensitized worms reveal new secrets. Curr Biol 20, R598-600.

44 Brenner, J. L., Jasiewicz, K. L., Fahley, A. F., Kemp, B. J., and Abbott, A. L. (2010). Loss of individual microRNAs causes mutant phenotypes in sensitized genetic backgrounds in *C. elegans*. Curr Biol 20, 1321-1325.

45 Banerjee, S., Neveu, P., and Kosik, K. S. (2009). A coordinated local translational control point at the synapse involving relief from silencing and MOV10 degradation. Neuron 64, 871-884.

46 Sigurdsson, T., Stark, K. L., Karayiorgou, M., Gogos, J. A., and Gordon, J. A. (2010). Impaired hippocampal-prefrontal synchrony in a genetic mouse model of schizophrenia. Nature 464, 763-767.

47 Kang, H. J., Kawasawa, Y. I., Cheng, F., Zhu, Y., Xu, X., Li, M., Sousa, A. M., Pletikos, M., Meyer, K. A., Sedmak, G., et al, (2011). Spatio-temporal transcriptome of the human brain. Nature 478, 483-489.

48 Drew, L. J., Stark, K. L., Fenelon, K., Karayiorgou, M., Macdermott, A. B., and Gogos, J. A. (2011). Evidence for altered hippocampal function in a mouse model of the human 22q11.2 microdeletion. Mol Cell Neurosci 47, 293-305.

Various references are cited herein, the contents of which are hereby incorporated by reference in their entireties.

What is claimed is:

1. A method of increasing neuronal connectivity in a human subject with schizophrenia, comprising administering to said subject a therapeutic amount of an agent that inhibits Mirta22 activity, wherein Mirta22 is encoded by a nucleic acid comprising a sequence of SEQ ID NO:3, and where said amount increases connectivity between neurons in an in vitro assay, as determined by an increase in the number of primary dendrites, an increase in dendrite spine density, or a combination thereof.

2. The method of claim 1, where the agent is selected from the group consisting of antisense RNA comprising a sequence complementary to the Mirta22 mRNA; and RNAi comprising a sequence complementary to the Mirta22 mRNA.

3. The method of claim 2, wherein the RNAi comprises shRNA comprising a sequence complementary to the Mirta22 mRNA.

* * * * *